US012594283B2

(12) United States Patent
Kalyanaraman et al.

(10) Patent No.: US 12,594,283 B2
(45) Date of Patent: Apr. 7, 2026

(54) MITOCHONDRIA-TARGETED ATOVAGONE: A MORE POTENT AND MORE EFFECTIVE ANTITUMOR, ANTIMICROBIAL, AND ANTIMALARIAL DRUG

(71) Applicants: The Medical College of Wisconsin, Inc., Milwaukee, WI (US); Aix-Marseille Université, Marseilles (FR)

(72) Inventors: Balaraman Kalyanaraman, Milwaukee, WI (US); Gang Cheng, Milwaukee, WI (US); Micael Joël Hardy, Nimes (FR)

(73) Assignees: The Medical College of Wisconsin, Inc., Milwaukee, WI (US); Aix-Marseille Universite, Marseilles (FR)

( * ) Notice: Subject to any disclaimer, the term of this patent is extended or adjusted under 35 U.S.C. 154(b) by 951 days.

(21) Appl. No.: 17/770,924

(22) PCT Filed: Oct. 26, 2020

(86) PCT No.: PCT/US2020/057363

§ 371 (c)(1),
(2) Date: Apr. 21, 2022

(87) PCT Pub. No.: WO2021/081500

PCT Pub. Date: Apr. 29, 2021

(65) Prior Publication Data

US 2023/0017373 A1 Jan. 19, 2023

Related U.S. Application Data

(60) Provisional application No. 62/925,619, filed on Oct. 24, 2019.

(51) Int. Cl.

| | |
|---|---|
| ***A61K 31/66*** | (2006.01) |
| ***A61K 31/122*** | (2006.01) |
| ***A61K 45/06*** | (2006.01) |
| ***A61P 35/00*** | (2006.01) |
| ***C07C 49/84*** | (2006.01) |
| ***C07F 9/535*** | (2006.01) |
| ***C07F 9/54*** | (2006.01) |

(52) U.S. Cl.

CPC ............ *A61K 31/66* (2013.01); *A61K 31/122* (2013.01); *A61K 45/06* (2013.01); *A61P 35/00* (2018.01); *C07C 49/84* (2013.01); *C07F 9/535* (2013.01); *C07F 9/5435* (2013.01)

(58) Field of Classification Search

CPC ...... A61K 31/66; A61K 31/122; A61K 45/06; A61K 31/662; A61P 35/00; C07C 49/84; C07F 9/535; C07F 9/5435; C07F 9/5456

See application file for complete search history.

(56) References Cited

U.S. PATENT DOCUMENTS

| | | | | |
|---|---|---|---|---|
| 4,981,874 A * | 1/1991 | Latter | .................. C07C 229/60 514/682 |
| 2009/0221715 A1 | 9/2009 | Kumar et al. | |
| 2011/0004024 A1* | 1/2011 | Saralya | .................. C07C 50/32 568/328 |

FOREIGN PATENT DOCUMENTS

| | | |
|---|---|---|
| WO | 2018213751 A1 | 11/2018 |
| WO | 2019104115 A1 | 5/2019 |
| WO | 2019108729 A1 | 6/2019 |

OTHER PUBLICATIONS

Ansó et al., The Mitochondrial Respiratory Chain is Essential for Haematopoietic Stem Cell Function, Nature Cell Biology, 2017, 19(6):614-625.
Araujo et al., Remarkable In Vitro and In Vivo Activities of the Hydroxynaphthoquinone 566C80 Against Tachyzoites and Tissue Cysts of Toxoplasma Gondi, Antimicrobial Agents and Chemotherapy, 1991, 35(2):293-299.
Ashton et al., The Anti-Malarial Atovaquone Increases Radiosensitivity by Alleviating Tumour Hypoxia, Nature Communications, 2016, 7(1):12308, pp. 1-13.
Barton et al., Inhibiting Plasmodium Cytochrome bc1: A Complex Issue, Current Opinion in Chemical Biology, 2010, 14:440-446.
Birth et al., Structural Analysis of Atovaquone-Inhibited Cytochrome bc1 Complex Reveals the Molecular Basis of Antimalarial Drug Action, Nature Communications, 2014, 5(1):4029, pp. 1-11.
Boyle et al., Mitochondria-Targeted Drugs Stimulate Mitophagy and Abrogate Colon Cancer Cell Proliferation, Journal of Biological Chemistry, 2018, 293(38):14891-14904.
Capper et al., Antimalarial 4 (1H)-Pyridones Bind to the Qi Site of Cytochrome bc 1, Proceedings of the National Academy of Sciences, 2015, 112(3):755-760.
Chaudhary et al., Regulatory T Cells in the Tumor Microenvironment and Cancer Progression: Role and Therapeutic Targeting, Vaccines, 2016, 4(3):28, pp. 1-25.
Chen et al., Targeting Mitochondria by Anthelmintic Drug Atovaquone Sensitizes Renal Cell Carcinoma to Chemotherapy and Immunotherapy, Journal of Biochemical and Molecular Toxicology, 2018, 32(9):e22195.
Cheng et al., Mitochondria-Targeted Vitamin E Analogs Inhibit Breast Cancer Cell Energy Metabolism and Promote Cell Death, BMC Cancer, 2013, 13(1):1-14.
Cheng et al., Mitochondria-Targeted Analogues of Metformin Exhibit Enhanced Antiproliferative and Radiosensitizing Effects in Pancreatic Cancer Cells, Cancer Research, 2016, 76(13):3904-3915.
Cheng et al., Targeting lonidamine to Mitochondria Mitigates Lung Tumorigenesis and Brain Metastasis, Nature Communications, 2019, 10(1):2205, pp. 1-14.
Cheng et al., Potent Inhibition of Tumour Cell Proliferation and Immunoregulatory Function by Mitochondria-Targeted Atovaquone, Scientific Reports, 2020, 10(1):17872, pp. 1-26.

(Continued)

*Primary Examiner* — Danah Al-Awadi
*Assistant Examiner* — Chantal Adlam
(74) *Attorney, Agent, or Firm* — Quarles & Brady LLP

(57) ABSTRACT

The present invention provides novel mitochondria-targeted Atovaquone compounds (Mito-ATO), a mitochondria-targeted derivative of Atovaquone, and methods of using such compounds. Methods of treating cancer using mito-ATO are also provided. Methods of enhancing an anti-tumor immune response by administering mito-ATO are further provided.

22 Claims, 28 Drawing Sheets

(56) References Cited

OTHER PUBLICATIONS

Cifuentes Kottkamp et al., Atovaquone Inhibits Arbovirus Replication through the Depletion of Intracellular Nucleotides, Journal of Virology, 2019, 93(11):e00389-19, pp. 1-15.
Das et al., Regulatory T Cells under the Mercy of Mitochondria, Cell Metabolism, 2019, 29(2):243-245.
Fiorillo et al., Repurposing Atovaquone: Targeting Mitochondrial Complex III and OXPHOS to Eradicate Cancer Stem Cells, Oncotarget, 2016, 7(23):34084, pp. 1-16.
Fry et al., Site of Action of the Antimalarial Hydroxynaphthoquinone, 2-[trans-4-(4'-chlorophenyl) cyclohexyl]-3-hydroxy-1, 4-naphthoquinone (566C80), Biochemical Pharmacology, 1992, 43(7):1545-1553.
Goodman et al., Is the Mitochondrion a Good Malaria Drug Target?, Trends in Parasitology, 2017, 33(3):185-193.
Ino et al., Immune Cell Infiltration as an Indicator of the Immune Microenvironment of Pancreatic Cancer, British Journal of Cancer, 2013, 108(4):914-923.
Kessl et al., Molecular Basis for Atovaquone Binding to the Cytochrome bc 1 Complex, Journal of Biological Chemistry, 2003, 278(33):31312-31318.
Klopman et al., Computer Automated log P Calculations based on an Extended Group Contribution Approach, Journal of Chemical Information and Computer Sciences, 1994, 34(4):752-781.
Lane et al., Selection of Plasmodium Falciparum Cytochrome B Mutants by Putative PfNDH2 Inhibitors, Proceedings of the National Academy of Sciences, 2018, 115(24):6285-6290.
Najafi et al., Cancer Stem Cells (CSCs) in Cancer Progression and Therapy, Journal of Cellular Physiology, 2019, 234(6):8381-8395.
Nayak et al., Oxidative Phosphorylation: A Target for Novel Therapeutic Strategies Against Ovarian Cancer, Cancers, 2018, 10(9):337, pp. 1-15.
Ohue et al., Regulatory T (Treg) Cells in Cancer: Can Treg Cells be a New Therapeutic Target?, Cancer Science, 2019, 110(7):2080-2089.
Oxenius et al., Virus-Specific Major MHC Class II-Restricted TCR-Transgenic Mice: Effects on Humoral and Cellular Immune Responses After Viral Infection, European Journal of Immunology, 1998, 28(1):390-400.
Reinhardt et al., Cytokine-Secreting Follicular T Cells Shape the Antibody Repertoire, Nature Immunology, 2009, 10(4):385-393.
Salabei et al., Comprehensive Measurement of Respiratory Activity in Permeabilized Cells using Extracellular Flux Analysis, Nature Protocols, 2014, 9(2):421-438.
Shitara et al., Regulatory T Cells: A Potential Target in Cancer Immunotherapy, Annals of the New York Academy of Sciences, 2018, 1417(1):104-115.
Sodero et al., Insights into Cytochrome bc 1 Complex Binding Mode of Antimalarial 2-hydroxy-1, 4-naphthoquinones through Molecular Modelling, Memórias do Instituto Oswaldo Cruz, 2017, 112:299-308.
Stickles et al., Atovaquone and ELQ-300 Combination Therapy as a Novel Dual-Site Cytochrome bc 1 Inhibition Strategy for Malaria, Antimicrobial Agents and Chemotherapy, 2016, 60(8):4853-4859.
Sun et al., Inhibition of Mitochondrial Respiration Overcomes Hepatocellular Carcinoma Chemoresistance, Biochemical and Biophysical Research Communications, 2019, 508(2):626-632.
Takabe et al., A Repurposed Drug for Brain Cancer: Enhanced Atovaquone Amorphous Solid Dispersion by Combining a Spontaneously Emulsifying Component with a Polymer Carrier, Pharmaceutics, 2018, 10(2):60, pp. 1-20.
Togashi et al., Regulatory T Cells in Cancer Immunosuppression—Implications for Anticancer Therapy, Nature Reviews Clinical Oncology, 2019, 16(6):356-371.
Viswanadhan et al., Atomic Physicochemical Parameters for Three Dimensional Structure Directed Quantitative Structure-Activity Relationships. 4. Additional Parameters for Hydrophobic and Dispersive Interactions and their Application for an Automated Superposition of Certain Naturally Occurring Nucleoside Antibiotics, Journal of Chemical Information and Computer Science, 1989, 29(3):163-172.
Wang et al., Effects of Tumor Metabolic Microenvironment on Regulatory T Cells, Molecular Cancer, 2018, 17(1):1-15.
Weinberg et al., Targeting Mitochondria Metabolism for Cancer Therapy, Nature Chemical Biology, 2015, 11(1):9-15.
Weinberg et al., Mitochondrial Complex III is Essential for Suppressive Function of Regulatory T Cells, Nature, 2019, 565(7740):495-499.
Weinstein et al., TFH Cells Progressively Differentiate to Regulate the Germinal Center Response, Nature Immunology, 2016, 17(10):1197-1205.
Wheaton et al., Metformin Inhibits Mitochondrial Complex I of Cancer Cells to Reduce Tumorigenesis, Elife, 2014, 3: e02242, pp. 1-18.
Xiang et al., Gene Expression-Based Discovery of Atovaquone as a STAT3 Inhibitor and Anticancer Agent, Blood, The Journal of the American Society of Hematology, 2016, 128(14):1845-1853.
Xin et al., A Critical Role of IL-21-Induced BATF in Sustaining CD8-T-Cell-Mediated Chronic Viral Control, Cell Reports, 2015, 13(6):1118-1124.
Xin et al., Single-Cell RNA Sequencing Unveils an IL-10-Producing Helper Subset that Sustains Humoral Immunity during Persistent Infection, Nature Communications, 2018, 9(1):5037.
Zhong et al., Identification of Secreted Proteins that Mediate Cell-Cell Interactions in an In Vitro Model of the Lung Cancer Microenvironment, Cancer Research, 2008, 68(17):7237-7245.
Zhou et al., Prognostic Value of Tumor-Infiltrating Foxp3+ Regulatory T Cells in Patients with Breast Cancer: A Meta-Analysis, Journal of Cancer, 2017, 8(19):4098, pp. 1-8.
Zielonka et al., Mitochondria-Targeted Triphenylphosphonium-Based Compounds: Syntheses, Mechanisms of Action, and Therapeutic and Diagnostic Applications, Chemical Reviews, 2017, 117(15):10043-10120.
European Patent Office, Extended European Search Report, Application No. 20880080.5, Dec. 22, 2022, 9 pages.
PCT International Search Report and Written Opinion, Application No. PCT/US2020/057363, Jan. 14, 2021, 8 pages.

* cited by examiner

A

ATO $Mito_4$-ATO $Mito_{10}$-ATO $Mito_{12}$-ATO $Mito_{16}$-ATO

B
C
% Live CD4 T cells
% IFNγYFP of Live CD4 T cells
% FoxP3+CD25+ of Live CD4 T cells
DMSO control
0.2 μM
0.3 μM
0.4 μM
0.5 μM
0.6 μM
0.7 μM
0.8 μM
0.9 μM
1 μM
1.2 μM
1.5 μM
Mito4-ATO
Mito12-ATO NMR Spectra of $Mito_{10}$-ATO

$^{31}P$ NMR (400.13 MHz, $CDCl_3$)

$Mito_{10}$-ATO

$^{13}$CAPT (75 MHz, $CDCl_3$)

NMR Spectra of Mito$_4$-ATO

$^{31}$P NMR (400.13 MHz, $CDCl_3$)

$^1H$ NMR (400.13 MHz, $CDCl_3$)

$^{13}CAPT$ (75 MHz, $CDCl_3$)

NMR Spectra of Mito$_{12}$-ATO

$^{31}$P NMR (400.13 MHz, $CDCl_3$)

Mito$_{12}$-ATO

$^{1}$H NMR (400.13 MHz, $CDCl_3$)

$^{13}$CAPT (75 MHz, $CDCl_3$)

NMR Spectra of Mito$_{16}$-ATO

$^{31}$P NMR (400.13 MHz, $CDCl_3$)

Mito$_{16}$-Ato

$^{1}$H NMR (400.13 MHz, $CDCl_3$)

$^{13}$CAPT (75 MHz, $CDCl_3$)

Mito$_{16}$-Ato

NMR Spectra of ATO-$C_4$

$^1$H NMR (400.13 MHz, $CDCl_3$)

$^{13}$CAPT (75 MHz, $CDCl_3$)

NMR Spectra of ATO-$C_{10}$

$^1$H NMR (400.13 MHz, $CDCl_3$)

$^{13}$CAPT (75 MHz, $CDCl_3$)

Butyl-ATO (ATO-$C_4$)

Decyl-ATO (ATO-$C_{10}$)

Effects of ATO, Mito-PEG-ATO and Mito-ATO analogs on cell proliferation in brain cancer cells, U87MG

ATO

Mito$_4$-ATO

Mito$_{10}$-ATO

Mito$_{12}$-ATO

Mito$_{16}$-ATO

Decyl-ATO

Butyl-ATO

MITOCHONDRIA-TARGETED ATOVAGONE: A MORE POTENT AND MORE EFFECTIVE ANTITUMOR, ANTIMICROBIAL, AND ANTIMALARIAL DRUG

CROSS-REFERENCE TO RELATED APPLICATIONS

This application represents the national stage entry of PCT/US2020/057363 filed on Oct. 26, 2020 and claims the benefit of U.S. Provisional Patent Application No. 62/925,619, filed on Oct. 24, 2019, the contents of which is incorporated by reference herein in its entirety.

STATEMENT REGARDING FEDERALLY SPONSORED RESEARCH OR DEVELOPMENT

Not Applicable.

FIELD OF THE INVENTION

This invention relates generally to mitochondria-targeting cationic drugs, specifically to mito-ATO compounds, and methods of using the compounds to treat cancer and enhance the immune response in addition to overcoming drug resistance including kinase resistance in cancers.

BACKGROUND

Chemotherapy, drug resistance, and metabolic reprogramming. Most forms of chemotherapy (conventional antitumor agents such as doxorubicin, cis-platin, targeted therapies involving kinase inhibitors such as BRAF inhibitors) and immunotherapy using the check point inhibitors invariably induce drug resistance that renders them eventually ineffective (1). Numerous mechanisms (e.g., activation of drug efflux pumps) for drug resistance have been proposed (2). Recent reports suggest that metabolic reprogramming between a glycolytic phenotype and oxidative phosphorylation (OXPHOS) occurs during tumorigenesis or during oncogenic kinase inhibition in cancer cells (3,4). The critical dependence of cancer cells on OXPHOS or mitochondrial respiration for energy and survival suggests that cancer cell-selective and potent inhibitors of OXPHOS may be therapeutically exploited for inhibiting tumor growth, preventing or delaying resistance to kinase inhibitors (5).

Pancreatic Cancer. FDA approved drugs currently used against pancreatic cancer target DNA metabolism and DNA integrity. Gain-of-function mutations in KRAS at codons 12, 13, and 61 are observed in over 90% of pancreatic ductal adenocarcinoma. Loss-of-function mutations in three specific tumor suppressor genes occur in the majority of PDAs: TP53, CDKN2A, and SMAD4. A preponderance of new evidence shows that pancreatic cancer cells are especially dependent on mitochondrial oxidative phosphorylation under low nutrient conditions, and that mitochondrial metabolism represents a key metabolic vulnerability.

A need exists for compounds that are effective in inhibiting tumor formation (i.e., reducing the severity or slowing the progression of symptoms of cancer) which have increased efficacy at lower doses while also mitigating resistance to chemo and radiotherapies. There is an urgent need to develop a new class of OXPHOS-targeting drugs which can be used for cancer treatment, including pancreatic cancer.

SUMMARY OF THE INVENTION

Other features of the present invention will become apparent after review of the specification, claims and drawings.

The present disclosure provides mito-ATO compounds, compositions comprising mito-ATO compounds, kits and methods of use.

In one aspect, the disclosure provides a mito-ATO compound of formula (I)

(I)

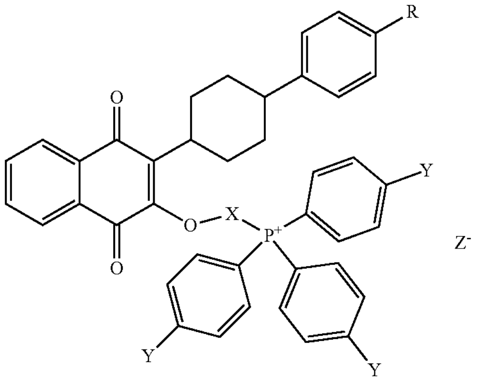

wherein

X is selected from an unsubstituted $C_1$-$C_{20}$ alkyl, substituted $C_1$-$C_{20}$ alkyl, $C_2$-$C_{20}$ alkenyl, phenyl, phenyl substituted $C_1$-$C_{20}$ alkyl, cycloalkyl substituted $C_1$-$C_{20}$ alkyl, an aminoacid, and polyethylene glycol (PEG);

each Y is independently selected from —H, —$CF_3$, methyl (Me), Cl, OMe, $C(O)CH_3$, $NO_2$, $N(Me)_2$;

R is selected from H, F, Cl, Br, and I; and $Z^-$ is selected from halogen, 2,2,2-trifluoroacetic acid (TFA), $HO^-$, $RCOO^-$, and acetic acid.

In one example, the mito-ATO compound is:

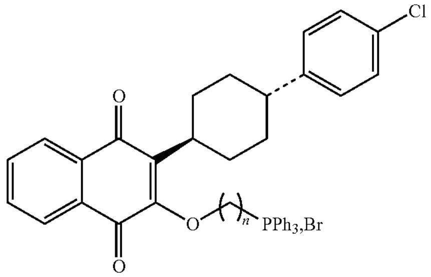

wherein n is an integer between 1 and 20.

In another example, the mito-ATO compound is:

(i)

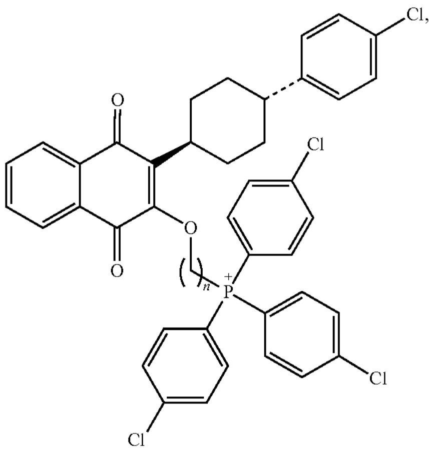

Mito$_{Cl}$-Ato (ii)

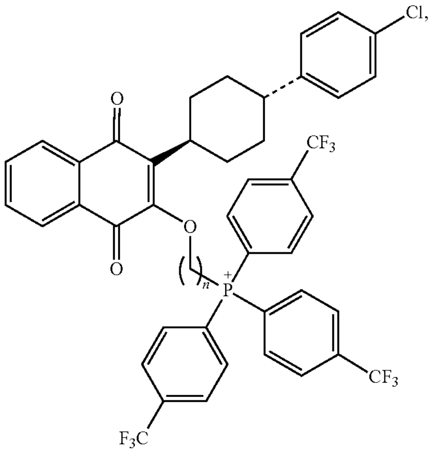

Mito$_{CF3}$-Ato (iii)

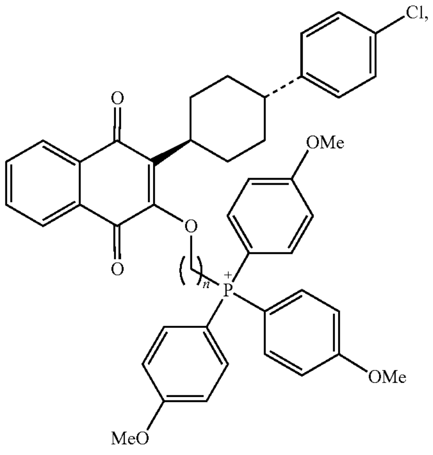

or

Mito$_{OMe}$-Ato

-continued (iv)

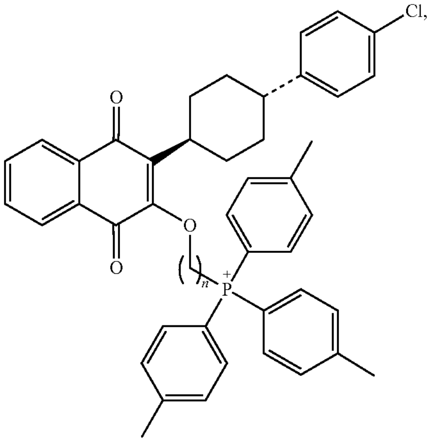

Mito$_{Me}$-Ato wherein n is an integer between 1 and 20.

In another example, the mito-ATO compound is:

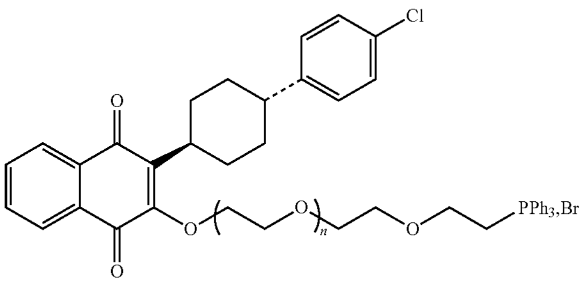

Mito$_{PEG}$-Ato wherein n is an integer between 1 and 20.

In another example, the mito-ATO compound is:

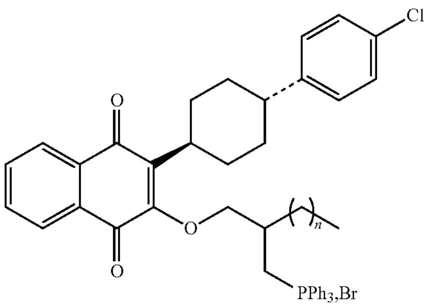

Mito$_{n}$-Ato2 wherein n is an integer between 1 and 20.

In another embodiment, the mito-ATO compound is of formula (II)

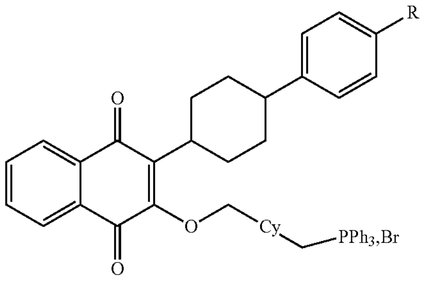

wherein Cy is a cyclic compound selected from cycloalkyl and aryl.

In one example, the mito-ATO compound is:

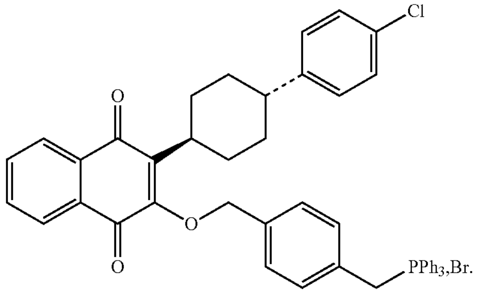

In another example, the mito-ATO compound is:

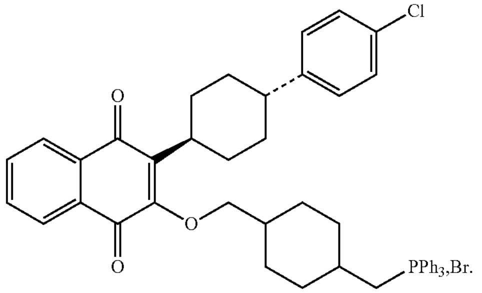

In another aspect, the disclosure provides a composition comprising the mito-ATO compound described herein and a pharmaceutically acceptable carrier.

In another aspect, the disclosure provides a method of reducing or inhibiting cancer cell growth in a subject having cancer, the method comprising: administering the mito-ATO compound described herein in a therapeutically effective amount to reduce or inhibit cancer cell growth.

In another aspect, the disclosure provides a method of reducing or inhibiting cancer cell growth in a subject having cancer, the method comprising: administering the mito-ATO compound of described herein, and administering atovaquone (ATO), wherein the mito-ATO and ATO in combination are administered in a therapeutically effective amount to reduce or inhibit cancer cell growth.

In a further aspect, the disclosure provides a method of increasing an effector T cell response to an anti-cancer therapy in a cancer patient, the method comprising administering the mito-ATO compound described herein in a therapeutically effective amount to increase the effector T cell response to the anti-cancer therapy.

In another aspect, the disclosure provides a kit comprising at least one mito-ATO compound described herein, a pharmaceutically acceptable carrier or diluent, and instructional material.

DETAILED DESCRIPTION OF THE INVENTION

In General. Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms “a”, “an”, and “the” include plural reference unless the context clearly dictates otherwise. As well, the terms “a” (or “an”), “one or more” and “at least one” can be used interchangeably herein. It is also to be noted that the terms “comprising”, “including”, and “having” can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

Compounds, Compositions and Synthesis

Figure 1:
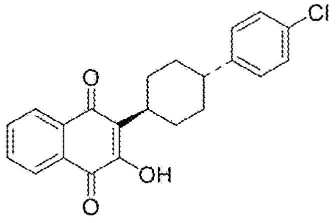
FIG. 1. Effects of ATO, Mito-ATO analogs, and related analogs on proliferation of MiaPaCa-2 cells. (A) Chemical structures of ATO and Mito-ATO analogs. (B) Effect of ATO on the proliferation of human pancreatic cancer cells was compared with that of $Mito_{10}$-ATO in the IncuCyte Live-Cell Imager. MiaPaCa-2 cells were treated with ATO and $Mito_{10}$-ATO. Cell proliferation was monitored in real-time with the continuous presence of indicated treatments until the end of each experiment. (C) Cell confluence (as control groups reach 98% confluency) is plotted against concentrations of ATO and Mito-ATO analogs. Dashed lines represent the fitting curves used to determine their $IC_{50}$ values as indicated.
Figure 1:
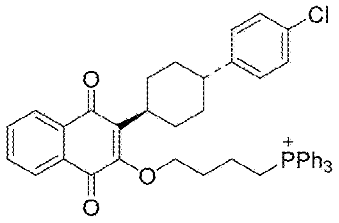
Figure 1:
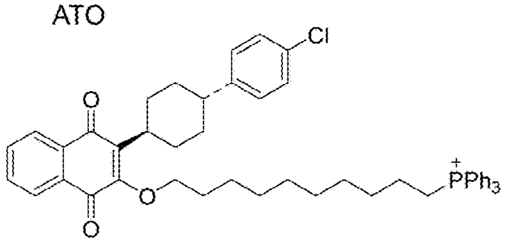
Figure 1:
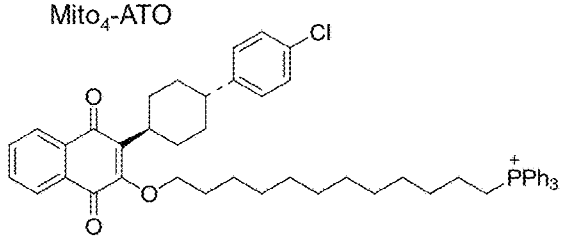
Figure 1:
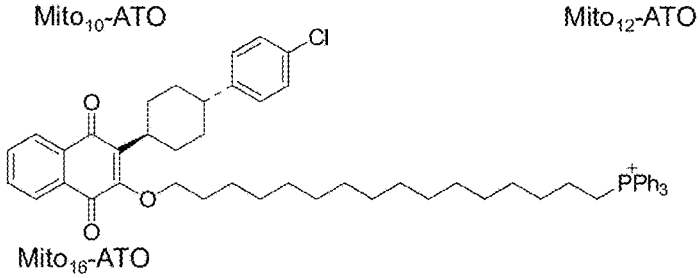
Figure 1:
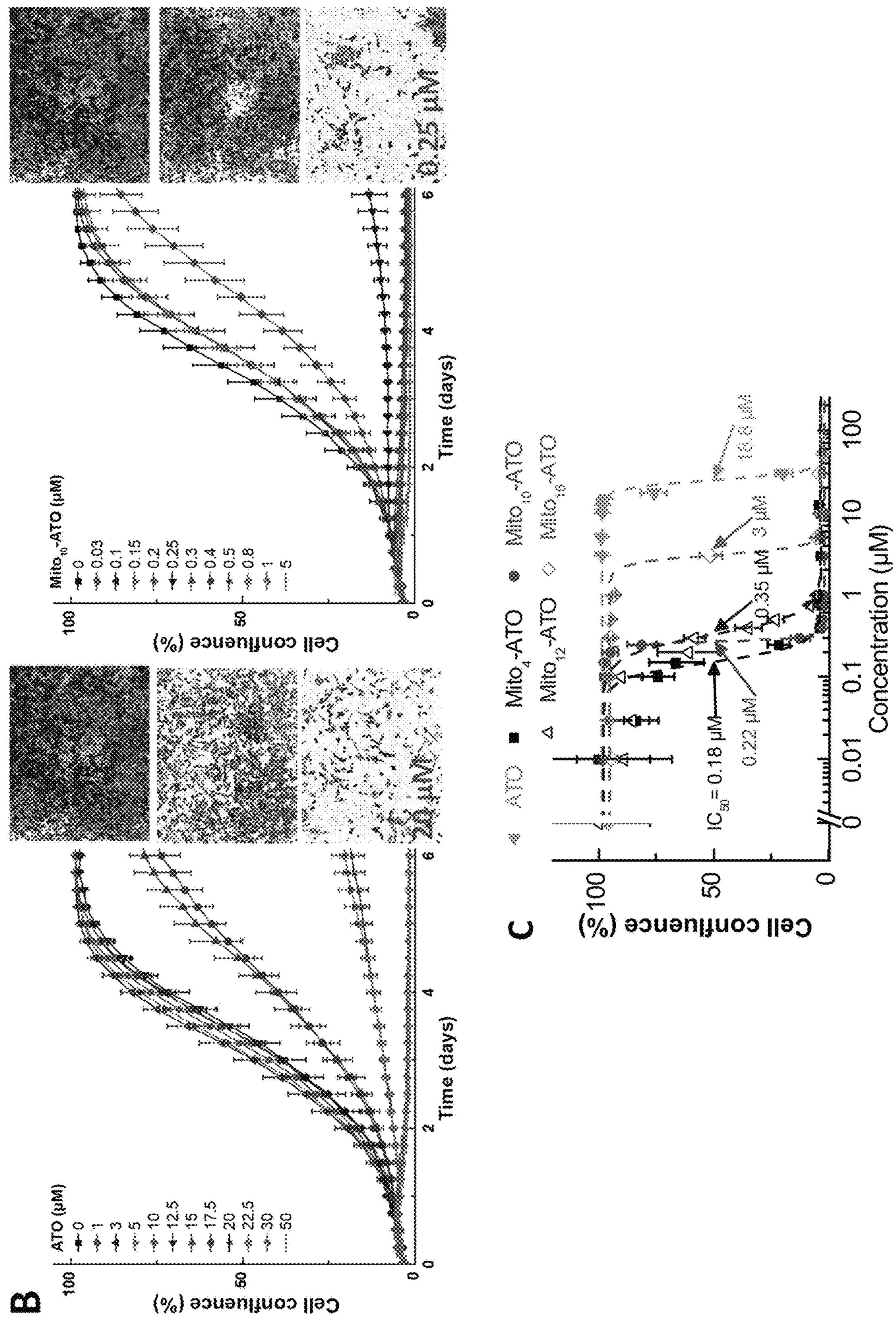

The present disclosure provides the synthesis of a modified form of atovaquone (mito-ATO) (FIG. 1A) that is at least 100-fold more effective than the unmodified atovaquone (ATO) (trans-2-[4-(4-chlorophenyl) cyclohexyl]-3-hydroxy-1,4-naphthalene-dione](FIG. 1A) in inhibiting cancer cell proliferation. The trans form of ATO is significantly more potent than the cis form. ATO, a lipophilic drug, inhibits the electron transport chain and mitochondrial respiration by displacing the ubiquinol at the oxidation site of complex III. The new compound (mito-ATO) reported here selectively inhibits mitochondrial respiration and oxidative phosphorylation (OXPHOS) in cancer cells at concentrations nearly 100-times lower than atovaquone.

Previous studies have shown that ATO binds to mitochondrial cytochrome bc1 complex (ubiquinol cytochrome c oxidoreductase or complex III) and inhibits its activity without significantly affecting the upstream NADH dehydrogenase (complex I) and succinate dehydrogenase (complex II) activities in cancer cells (FIG. 1B). In contrast, this disclosure shows that mito-ATO inhibits both mitochondrial complex I and complex III activities more potently than ATO (FIG. 1B). This shift in molecular targeting of both complex I and complex III possibly accounts for the increased potency of mito-ATO compared to ATO (that targets primarily complex III) in cancer cells.

Atovaquone (ATO), hydroxy-1,4-naphthoquinone analog of co-enzyme $Q_{10}$ or ubiquinone (FIG. 1A) is an FDA-approved antimicrobial drug for treating *pneumocystis* pneumonia and for preventing and treating malaria caused by the parasites *Pnemocystis jirovecii* and *Plasmodium falciparum* and toxoplasmosis infections in immune compromised HIV patients. ATO is the first clinically approved drug that targets *Plasmodium* cytochrome bc1 complex in mitochondria. ATO has a very high safety profile and is readily bioavailable; ATO has been in use in the clinic for many years, and millions of prescriptions are being issued around the world each year. ATO acts as a competitive inhibitor of complex III by displacing ubiquinol at the active site of the *Plasmodium* cytochrome bc1 complex. The catalytic core of the *Plasmodium* complex III consists of following three subunits that participate in the electron transfer pathway: cytochrome b, cytochrome c1, and the Rieske iron-sulfur protein [2Fe-2S]. Ubiquinone is reduced to ubiquinol by complex I and II and oxidized to ubiquinone at the catalytic site. ATO binds to the cytochrome bc1 (cyt bc1) complex and inhibits mitochondrial respiration and mitochondrial membrane potential in parasites and kills them. The $IC_{50}$ for ATO inhibition of cyt bc1 is around 3 nM in malarial parasites, and in mammalian cells is in the micromolar range. The cyt bc1 is inhibited at either the quinol oxidase ($Q_0$) or quinone reductase ($Q_1$) site and ATO selectively inhibits at $Q_0$ site. AQ resistance in *P. falciparum* parasites is associated with Y268S mutations at $Q_0$ site. The Y265S mutations result in nearly a 9,000-fold increase in $IC_{50}$ for ATO. However, drugs that inhibit at the $Q_1$ site of cyt bc1 are active against ATO-resistant *P. falciparum* parasites containing Y268S mutations.

Recently, ATO was repurposed for targeting mitochondrial complex III in breast cancer cells, and results show that ATO potently inhibits proliferation of breast cancer stem cells. Investigators proposed a similar mechanism (inhibition of complex III) of action for ATO in breast cancer cells, although the affinity of ATO to mitochondrial cyt bc1 complex in mammalian cells is suggested to be much lower than in parasites. Targeting AQ to complex III in ovarian cancer cells as a potential therapeutic strategy was proposed. More recent studies showed that ATO or ATO and proquanil (Malarone™) exhibits antitumor activity in both animal models and in patients with acute myelogenous leukemia (AML) and acute lymphocytic leukemia (ALL). It was proposed that ATO inhibits tumor growth by inhibiting phosphorylation of signal transducer and activator of transcription 3 (STAT3). AML treatment has remained unchanged, and cytotoxic chemotherapy has been the mainstay of treatment. ATO was proposed as a novel and clinically viable STAT3 inhibitor, a promising target for glioblastoma multiforme (GBM) therapy. ATO inhibited the proliferation of glioblastoma cells, and studies show its efficacy even in mice brain cancer xenografts. However, ATO concentration in the brain is too low to be chemotherapeutically effective. As Mito-ATO is nearly 100-fold more effective than ATO, Mito-ATO may be more effective than ATO under in vivo conditions, using procedures involving nanosystem and nanoemulsion formulations.

Tri-phenyl-phosphonium ($TPP^+$)-conjugated mitochondria-targeted agents, including mito-ATO described herein are potent and selective inhibitors of OXPHOS in tumor cells. Compared to their untargeted analogs, the $TPP^+$-conjugated analogs are typically more potent, for example about 100 to 1,000 times more potent in inhibiting tumor cell proliferation. In addition, $TPP^+$-containing analogs lack the toxicity associated with usual mitochondrial OXPHOS inhibitors (e.g., rotenone, cyanide), exhibiting a high therapeutic index and limited off-target effects. Conventional inhibitors of mitochondrial electron transport chain complexes such as cyanide, oligomycin, 2,4-dinitrophenol, are not specific for cancer cell mitochondria, and these all have a low therapeutic index. Biguanides (e.g., metformin) exhibit antitumor effects, and a proposed mechanism involves targeting mitochondrial OXPHOS, albeit weakly. Metformin efficacy is further limited by transport requiring the presence of organic cation transporters (OCT).

In contrast, the newly developed mitochondria targeted agents (MTAs) described herein consist of the $TPP^+$ moiety conjugated to an organic molecule (Atovaquone) via an aliphatic side chain. MTAs are targeted to mitochondria, driven by the presence of an increased negative mitochondrial membrane potential in cancer cells.

The present disclosure provides mitochondria-targeted Atovaquone compounds (Mito-ATO), a mitochondria-targeted derivative of Atovaquone.

In one embodiment, the disclosure provides a mito-ATO compound of formula (I)

(I)

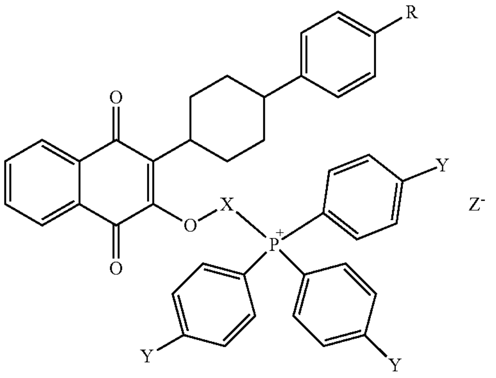

wherein

X is selected from an unsubstituted $C_1$-$C_{20}$ alkyl, substituted $C_1$-$C_{20}$ alkyl, $C_2$-$C_{20}$ alkenyl, phenyl, phenyl substituted $C_1$-$C_{20}$ alkyl, cycloalkyl substituted $C_1$-$C_{20}$ alkyl, an amino acid, and polyethylene glycol (PEG);

each Y is independently selected from —H, —$CF_3$, methyl (Me), Cl, OMe, $C(O)CH_3$, $NO_2$, $N(Me)_2$;

R is selected from H, F, Cl, Br, and I; and $Z^-$ is selected from halogen, 2,2,2-trifluoroacetic acid (TFA), $HO^-$, $RCOO^-$, and acetic acid. For Example, the mito-ATO compound can be

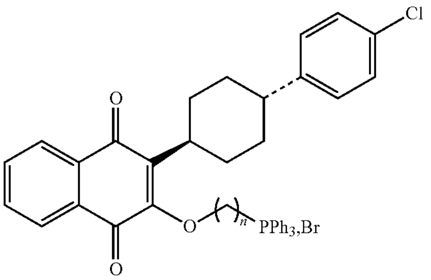

wherein n is an integer between 1 and 20.

In another example, the mito-ATO compound can be

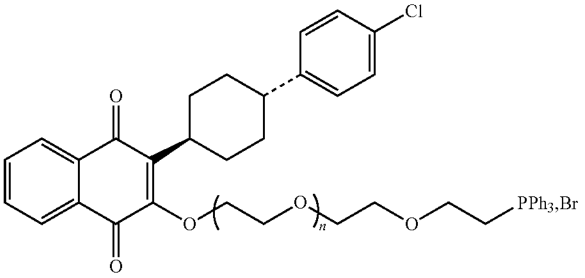

wherein n is an integer between 1 and 20.

In a preferred example, X is $C_1$-$C_{20}$ alkyl, each Y is H, R is Cl, and $Z^-$ is Br.

In one embodiment, the mito-ATO compound can be:
(i)
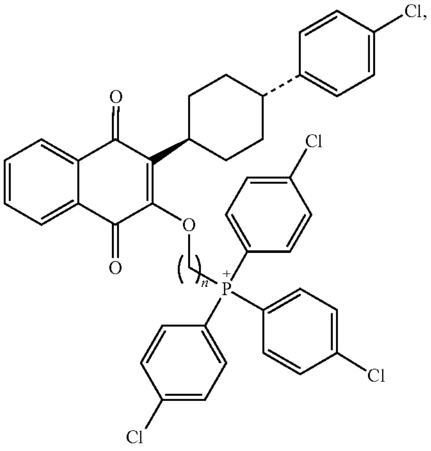
Mito$_{Cl}$-Ato
(ii)
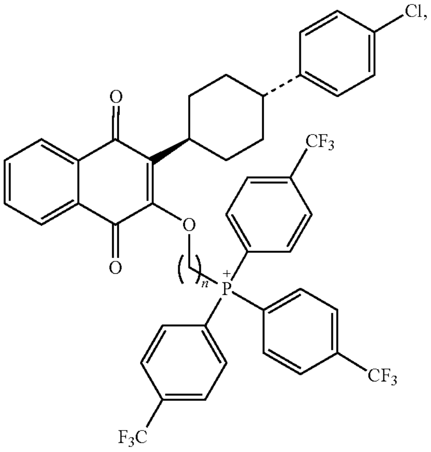
Mito$_{CF3}$-Ato
(iii)
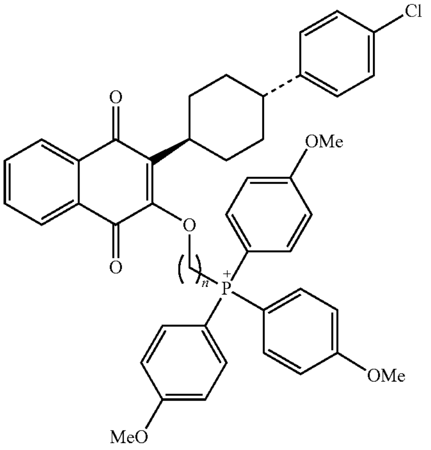
Mito$_{OMe}$-Ato
-continued
(iv)
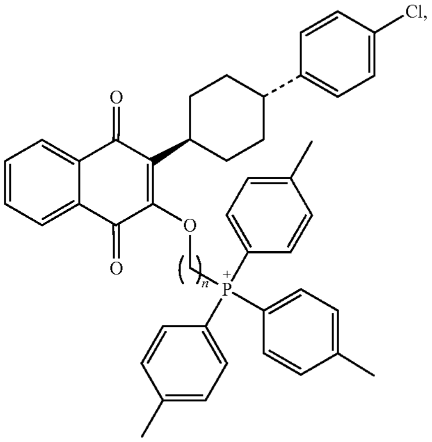
Mito$_{Me}$-Ato
wherein n is an integer between 1 and 20.
In one embodiment, the mito-ATO is:
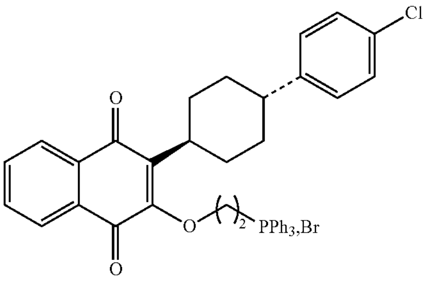
Mito$_2$-Ato
Another embodiment provides a mito-ATO compound of:
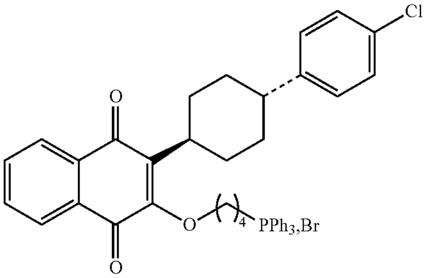
Mito$_4$-Ato Another embodiment provides a mito-ATO compound of:

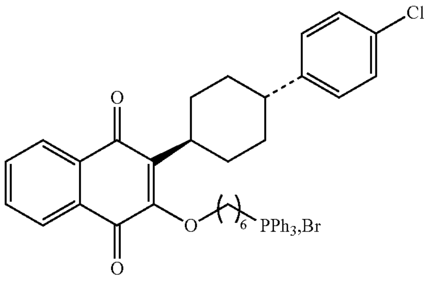

$Mito_6$-Ato

Another embodiment provides a mito-ATO compound of:

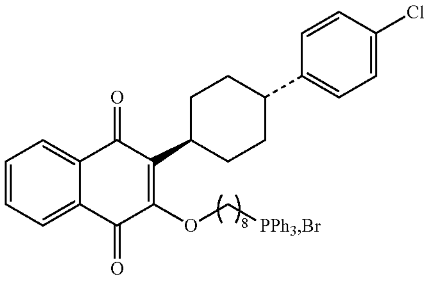

$Mito_8$-Ato

Another embodiment provides a mito-ATO compound of:

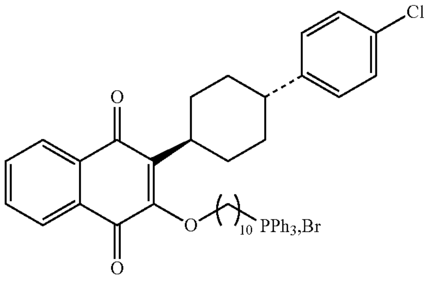

$Mito_{10}$-Ato

Another embodiment provides a mito-ATO compound of:

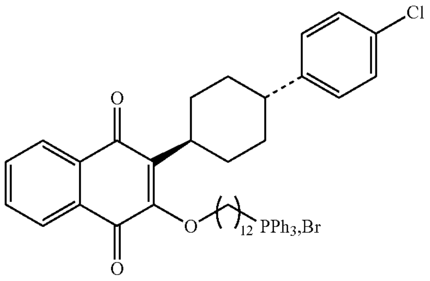

$Mito_{12}$-Ato

Another embodiment provides a mito-ATO compound of:

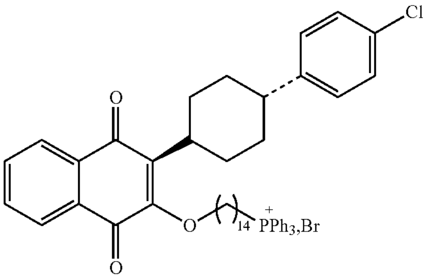

$Mito_{14}$-Ato

Another embodiment provides a mito-ATO compound of:

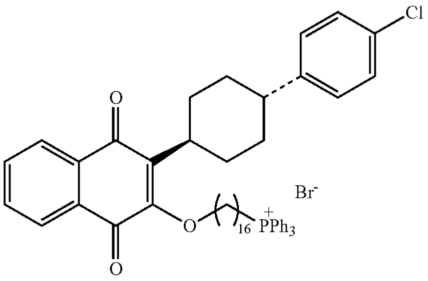

$Mito_{16}$-Ato

A control compound comprises:

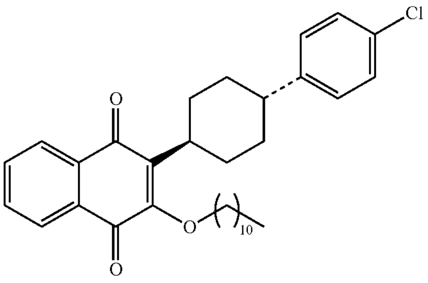

$Alkyl_{10}$-Ato

In another embodiment, the mito-ATO compound is a $mito_{PEG}$-ATO compound of:

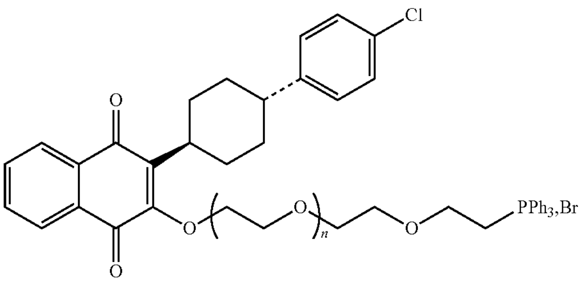

$Mito_{PEG}$-Ato wherein n is an integer between 1 and 20.

In another embodiment, the mito-ATO compound of formula (I), X is a substituted $C_1$-$C_{20}$ alkyl, each Y is H, R is Cl, and $Z^-$ is Br.

For Example, the mito-ATO compound can be

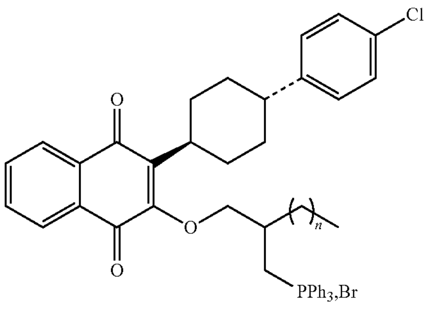

Mito$_n$-Ato wherein n is an integer between 1 and 20.

In another embodiment, the mito-ATO compound is formula (II)

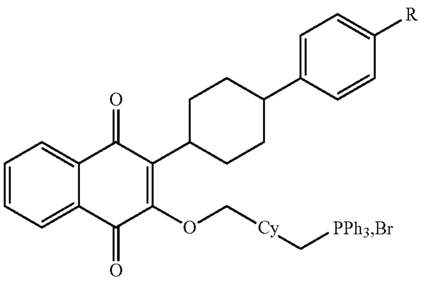

wherein Cy is a cyclic compound selected from cycloalkyl and aryl.

In one embodiment, the mito-ATO compound of formula (II) is

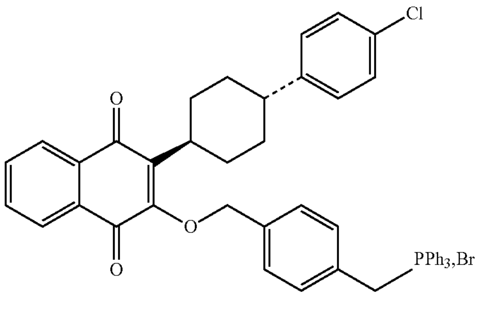

Another embodiment provides a mito-ATO compound of:

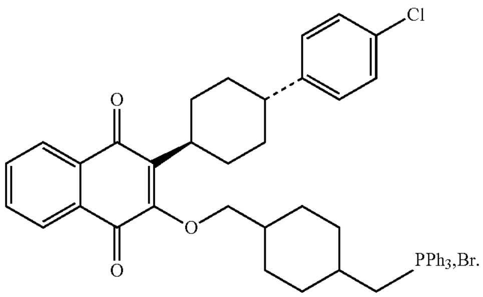

Suitable $C_1$-$C_{20}$ alkyl include, but are not limited to, for example, methyl, ethyl, butyl, propyl, butyl, pentyl, hexyl, heptyl, octyl, nonyl, decyl, undecyl, dodecyl, $C_{13}$alkyl, $C_{14}$alkyl, $C_{15}$alkyl, $C_{16}$alkyl, $C_{17}$alkyl, $C_{18}$alkyl, $C_{19}$alkyl, and $C_{20}$alkyl.

Cycloalkyl are any univalent radical (formed by removal of one hydrogen atom from a cycloalkane. Suitable cycloalkyl, include, but are not limited to, for example $C_3$-$C_6$ cycloalkyl.

An aryl is a functional group or substituent derived from an aromatic carbocyclic group comprising at least five carbon atoms to 15 carbon atoms, such as five to ten carbon atoms, having a single ring or multiple condensed rings, which condensed rings can or may not be aromatic provided that the point of attachment is through an atom of the aromatic carbocyclic group. In one example, the aromatic ring is an aromatic hydrocarbon, such as phenyl, tolyl, xylyl, and naphthyl.

Suitable amino acids to use in the mito-ATO formulations include, but are not limited to, for example, glycine (Gly), leucine (Leu), histidine (His), isoleucine (Ile), lysine (Lys), methionine (Met), phenylalanine (Phe), threonine (Thr), tryptophan (Trp), valine (Val), arginine (Arg), cysteine (Cys), glutamine (Gln), proline (Pro), serine (Ser), Tyrosine (Tyr), alanine (Ala), asparagine (Asn), aspartic acid (Asp), glutamic acid (Glu), and selenocysteine (Sec).

Suitable, in the above mito-ATO, n is an integer from 1-20, alternatively 8-20, alternatively 1-12, preferably 6-10, and including, for example, 1, 2, 3, 4, 5, 6, 7, 8, 9, 10, 11, 12, 13, 14, 15, 16, 17, 18, 19, and 20.

The present disclosure also provides compositions comprising the mito-ATO compounds described herein, and a pharmaceutically acceptable carrier. A "pharmaceutically acceptable carrier" means any conventional pharmaceutically acceptable carrier, vehicle, or excipient that is used in the art for production and administration of compositions to a subject. Pharmaceutically acceptable carriers are typically non-toxic, inert, solid or liquid carriers which are physiologically balanced. Typically, phosphate buffered saline or other saline solutions are physiologically acceptable carriers. A pharmaceutically acceptable carrier can be selected on the basis of the selected route of administration and standard pharmaceutical practice. The compounds may be formulated into dosage forms according to standard practices in the field of pharmaceutical preparations. See Alphonso Gennaro, ed., *Remington's Pharmaceutical Sciences,* 18th Ed., (1990) Mack Publishing Co., Easton, Pa., which is incorporated by reference in its entirety. Suitable dosage forms may comprise, but are not limited to, for example, solutions, parenteral solutions, injectable solutions, troches, suppositories, or suspensions.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents, absorbents or lubricating agents. Additional oral administration forms are contemplated, including, but not limited to, elixirs, liquids, solutions, suspensions, emulsions, multi-layer tablets, soft gelatin capsules, hard gelatin capsules, troches, lozenges, beads, granules, particles, microparticles, dispensible granules, cachets, among others. Formulations of the present technology suitable for oral administration can be presented as discrete units, such as capsules, caplets or tablets. These oral formulations also can comprise a solution or a suspension in an aqueous liquid or a non-aqueous liquid. The formulation can be an emulsion, such as an oil-in-water liquid emulsion or a water-in-oil liquid emulsion. The oils can be administered by adding the purified and sterilized liquids to a prepared enteral formula, which can then be placed in the feeding tube of a patient who is unable to swallow. Another oral administration may be the formation of a liquid or gel suitable for oral dosage. In one embodiment, the compounds may be formulated in water, juice, or other beverage for oral consumption.

For parenteral administration, the active agent may be mixed with a suitable carrier or diluent such as water, an oil (e.g., a vegetable oil), ethanol, saline solution (e.g., phosphate buffer saline or saline), aqueous dextrose (glucose) and related sugar solutions, glycerol, or a glycol such as propylene glycol or polyethylene glycol. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or nonaqueous solution, dispersion, suspension or emulsion.

The pharmaceutical composition is preferably in unit dosage form. In such form the preparation is divided into unit doses containing appropriate quantities of the active component. The unit dosage form can be a packaged preparation, the package containing discrete quantities of preparation, such as packeted tablets, capsules, and powders in vials, or ampoules. Also, the unit dosage form can be a capsule, tablet, cachet, or lozenge itself, or it can be the appropriate number of any of these in packaged form.

Figure 7:
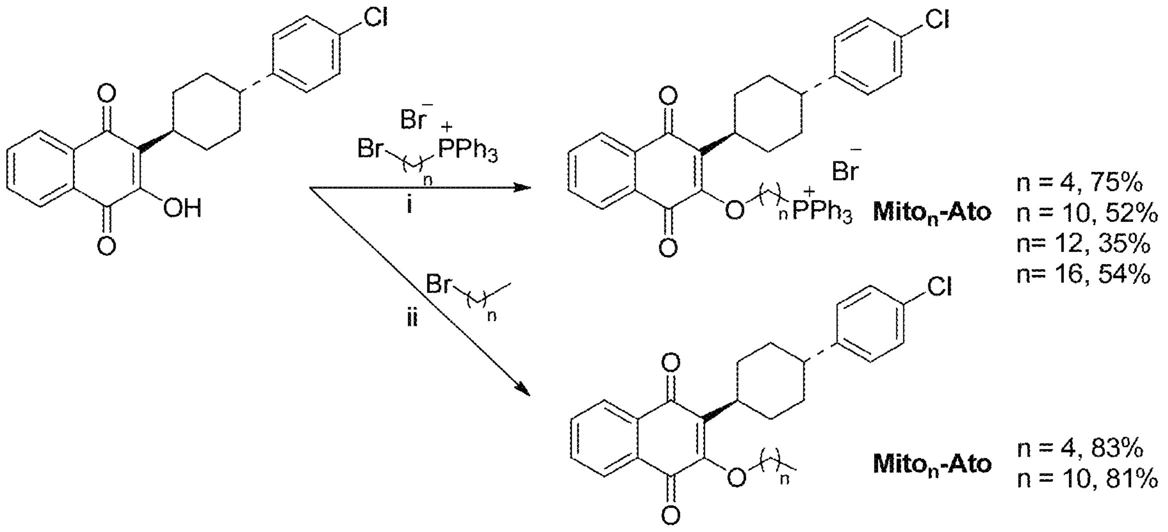
FIG. 7. Synthetic scheme of the mitochondria-targeted analogs of ATO ($Mito_n$-ATO) of the present disclosure. The Mito-ATO compounds were prepared by reacting the appropriates bromoalkyl-triphenylphosphonium bromides with ATO in the presence of potassium carbonate in dimethylformamide (DMF).

Methods of synthesizing the mito-ATOs of the present disclosure are shown in FIG. 7, and described in the Examples below. Briefly, to a mixture of ATO (0.73 g, 1.9 mmol) and potassium carbonate (0.3 g, 2.1 mmol) in DMF (4 ml) was added (10-bromodecyl)-triphenylphosphonium bromide (1.1 g, 1.9 mmol). The mixture was stirred at 70° C. for 9 h. Methylene chloride ($CH_2Cl_2$) was added to the mixture followed by adding water (20 ml). The organic layer was washed twice with water and dried over anhydrous sodium sulfate. The excess solvent was removed under reduced pressure. Diethylether was subsequently added to the mixture to precipitate the compound. Purification by flash chromatography ($CH_2Cl_2$/EtOH, 9:1) yielded the desired compound $Mito_{10}$-Ato (0.95 g, 59% yield).

To a mixture of ATO (0.3 g, 0.82 mmol) and potassium carbonate (0.15 g, 0.82 mmol) in DMF (3 ml) was added (4-bromobutyl)-triphenylphosphonium bromide (0.39 g, 0.81 mmol). The mixture was stirred at 70° C. for 9 h. Methylene chloride ($CH_2Cl_2$) was added to the mixture followed by adding water (20 ml). The organic layer was washed twice with water and dried over anhydrous sodium sulfate. The excess solvent was removed under reduced pressure. Diethylether was subsequently added to the mixture to precipitate the compound. Purification by flash chromatography ($CH_2Cl_2$/EtOH, 9:1) yielded the desired compound $Mito_4$-Ato (0.47 g, 75% yield)

To a mixture of ATO (0.45 g, 1.2 mmol) and potassium carbonate (0.17 g, 1.2 mmol) in DMF (3 ml) was added (12-bromododecyl)-triphenylphosphonium bromide (0.6 g, 1.0 mmol). The mixture was stirred at 70° C. for 7 h. Methylene chloride ($CH_2Cl_2$) was added to the mixture followed by adding water (20 ml). The organic layer was washed twice with water and dried over anhydrous sodium sulfate. The excess solvent was removed under reduced pressure. Diethylether was subsequently added to the mixture to precipitate the compound. Purification by flash chromatography ($CH_2Cl_2$/EtOH, 9:1) yielded the desired compound $Mito_{12}$-Ato (0.31 g, 35% yield).

To a mixture of ATO (0.4 g, 1.1 mmol) and potassium carbonate (0.15 g, 1.1 mmol) in DMF (3 ml) was added bromobutane (0.15 g, 1.1 mmol). The mixture was stirred at 70° C. for 7 h. Diethylether ($Et_2O$) was added to the mixture followed by adding water (20 ml). The organic layer was washed twice with water and dried over anhydrous sodium sulfate. The excess solvent was removed under reduced pressure. Purification by flash chromatography (Pentane/EtOAc, 98:02) yielded the desired compound Ato-$C_4$ (0.38 g, 83% yield)

To a mixture of ATO (0.4 g, 1.1 mmol) and potassium carbonate (0.15 g, 1.1 mmol) in DMF (4 ml) was added bromodecane (0.24 g, 1.1 mmol). The mixture was stirred at 70° C. for 7 h. Diethylether ($Et_2O$) was added to the mixture followed by adding water (20 ml). The organic layer was washed twice with water and dried over anhydrous sodium sulfate. The excess solvent was removed under reduced pressure. Purification by flash chromatography (Hexane/EtOAc, 95:05) yielded the desired compound Ato-C10 (0.45 g, 81% yield) One skilled in the art is able to modify these methods to produce other mito-ATO compounds contemplated herein Methods of Use Cancer Treatment The compounds and compositions of the present disclosure may be used for methods of treating cancer, including methods of overcoming resistance to chemotherapies, for example, overcoming resistance to oncogene-targeted therapies or checkpoint inhibitors. The compounds and compositions comprising mito-ATO act as potent OXPHOS inhibitors, which can be used alone or in combination with other anti-cancer therapies, including chemotherapeutic agents, to treat cancer, including pancreatic cancer, in a subject in need thereof.

In one embodiment, the disclosure provides methods of treating cancer, including treatment of pancreatic cancer, melanoma, breast cancer, colon cancer, lung cancer, brain cancer (e.g., glioblastoma) among others.

In one embodiment, the disclosure provides methods of treating cancer, including treatment of cancers associated with increases levels of OXPHOS. In one embodiment, the $TPP^+$-conjugated mitochondria-targeted mito-ATOs selectively localize within the more negative mitochondria of cancer cells and are potent and selective inhibitors of OXPHOS in cancer cells, including, but not limited to melanoma, brain, breast, colon, lung, and pancreas cancer cells. As demonstrated in the examples, mito-ATO compounds potently inhibits OXPHOS and tumor cell proliferation in pancreatic cancer. As demonstrated in the examples, mito-ATO compounds potently inhibits tumor cell proliferation in brain cancer.

In one embodiment, the mito-ATO compounds of the present invention provide effective methods of treating cancer. In one embodiment, the mito-ATO compounds potently inhibit and reduce tumor formation. In some embodiments, the cancer is a primary tumor. In some embodiments, the cancer is a metastatic cancer. In one embodiment, the mito-ATO compounds or compositions described herein reduce or inhibit metastasis. In another embodiment, the mito-ATO compounds are able to treat or inhibit anti-cancer resistant (e.g., chemotherapeutic) or drug resistant cancer, for example, drug resistant melanoma. In another embodiment, the mito-ATO compounds are able to treat or inhibit pancreatic cancer. In another embodiment, the mito-ATO compounds are able to treat or inhibit brain cancer.

In some embodiments, the mito$_{PEG}$-ATO have are more potent than mito-ATO compounds in reducing or inhibiting cancer cell growth, for example, brain cancer cell growth.

By "cancer' or "tumor" we mean any abnormal proliferation of tissues, including solid and non-solid tumors. For instance, the composition and methods of the present invention can be utilized to treat cancers that manifest solid tumors such as skin cancer including melanoma, pancreatic cancer, breast cancer, colon cancer, lung cancer, prostate cancer, thyroid cancer, ovarian cancer, bladder cancer, and the like. The composition and methods of the present disclosure can also be utilized to treat non-solid tumor cancers such as non-Hodgkin's lymphoma, leukemia and the like.

The term "metastasis," "metastatic tumor" or "secondary tumor" refers to cancer cells that have spread to a secondary site, e.g., outside of the primary tumor tissue. Secondary sites include, but are not limited to, the lymphatic system, skin, distant organs (e.g., liver, stomach, pancreas, brain, etc.) and the like. In some embodiments, the mito-ATO compounds provide methods of treating a primary or secondary tumor.

In one embodiment, the disclosure provides a method of treating cancer in a subject having cancer comprising: administering the mito-ATO compound described herein in a therapeutically effective amount to treat the cancer.

In a preferred embodiment, the cancer is pancreatic cancer.

In another preferred embodiment, the cancer is brain cancer. Suitable types of brain cancer are known in the art and include cancers that metastasize to the brain, and glioblastomas.

In some embodiments, the cancer therapy involves inhibition of cyt bc1 complex of cancer cells. In some embodiments, the cancer therapy involves accumulation of mito-ATO into cancer cell mitochondria. In some embodiments, the mito-ATO compounds inhibit the complex III activity. In some embodiments, the mito-ATO compounds inhibit the complex I activity.

In some embodiments, the mito-ATO or compositions thereof can be used in combination with another mitochondrial complex I inhibitor. Suitable complex I inhibitors are known in the art and include, but are not limited to, rotenone, piericidin, among others.

In some embodiments, the mito-ATO or composition thereof can be used in combination with another mitochondrial complex III inhibitor. Suitable complex III inhibitors are known in the art and include, but are not limited to, antimycin A, atovaquone, myxothiazol, stigmatellin, azoxystrobin, and propylhexedine, phenylethyl isothiocyanate, among others.

The present disclosure also provides methods of reducing or inhibiting cancer cell growth in a subject having cancer, the method comprising administering the mito-ATO compound or compositions described herein in a therapeutically effective amount to reduce or inhibit cancer cell growth.

In another embodiment, the disclosure provides a method of inhibiting, reducing or delaying resistance of a cancer to an anti-cancer drug in a subject, the method comprising: administering the mito-ATO compound or compositions described herein in a therapeutically effective amount to inhibit, reduce or delay resistance of the cancer to the anti-cancer drug.

In some embodiments, the mito-ATO compound is administered co-currently with the anti-cancer drug. In other embodiments, the mito-ATO compound or composition is administered after beginning treatment with the anti-cancer drug. In other embodiments, the mito-ATO compound or composition is administered before, during or both before and during treatment with an anti-cancer drug.

By "subject" we mean mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, fish and the like. The term "subject" does not denote a particular age or sex. In a preferred embodiment, the subject is a human.

By "treating" we mean the management and care of a subject for the purpose of combating the disease, condition, or disorder. Treating includes the administration of a compound or composition described herein to reduce, inhibit, ameliorate and/or improve the onset of the symptoms or complications, alleviating the symptoms or complications, or reducing or eliminating the disease, condition, or disorder. For example, treating cancer in a subject includes the reducing, repressing, delaying or inhibiting cancer growth, reduction of tumor volume, and/or inhibiting, repressing, delaying or reducing metastasis of the tumor. Treating cancer in a subject also includes the reduction of the number of tumor cells within the subject. The term "treatment" can be characterized by at least one of the following: (a) the reducing, slowing or inhibiting the growth of cancer and cancer cells, including slowing or inhibiting the growth of metastatic cancer cells; (b) reducing or inhibiting the further growth of tumors; (c) reducing or inhibiting the metastasis of cancer cells within a subject; and (d) reducing or ameliorating at least one symptom of cancer. In some embodiments, the optimum effective amount can be readily determined by one skilled in the art using routine experimentation.

By "ameliorate", "amelioration", "improvement" or the like we mean a detectable improvement or a detectable change consistent with improvement that occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range about between any two of these values. Such improvement or change may be observed in treated subjects as compared to subjects not treated with the mito-ATO compounds, where the untreated subjects have, or are subject to developing, the same or similar disease, condition, symptom or the like.

Amelioration of a disease, condition, symptom or assay parameter may be determined subjectively or objectively, e.g., self-assessment by a subject(s), by a clinician's assessment or by conducting an appropriate assay or measurement, including, e.g., a quality of life assessment, a slowed progression of a disease(s) or condition(s), a reduced severity of a disease(s) or condition(s), or a suitable assay(s) for the level or activity(ies) of a biomolecule(s), cell(s) or by detection of cell migration within a subject. Amelioration may be transient, prolonged or permanent or it may be variable at relevant times during or after the mito-ATO compound is administered to a subject or is used in an assay or other method described herein or a cited reference, e.g., within about 1 hour of the administration or use of the mito-ATO compounds to about 3, 6, 9 months or more after a subject(s) has received the mito-ATO compounds.

By "modulation" of, e.g., a symptom, level or biological activity of a molecule, replication of a pathogen, cellular response, cellular activity or the like means that the cell level or activity is detectably increased or decreased. Such increase or decrease may be observed in treated subjects as compared to subjects not treated with the mito-ATO compounds, where the untreated subjects have, or are subject to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or about within any range about between any two of these values. Modulation may be determined subjectively or objectively, e.g., by the subject's self-assessment, by a clinician's assessment or by conducting an appropriate assay or measurement, including, e.g., quality of life assessments or suitable assays for the level or activity of molecules, cells or cell migration within a subject. Modulation may be transient, prolonged or permanent or it may be variable at relevant times during or after the mito-ATO compound is administered to a subject or is used in an assay or other method described herein or a cited reference, e.g., within about 1 hour of the administration or use of the mito-ATO compounds to about 3, 6, 9 months or more after a subject(s) has received the mito-ATO compounds.

By "administering" we mean any means for introducing the mito-ATO compounds or compositions into the body, preferably into the systemic circulation or locally to the tumor. Examples of systemic administration include, but are not limited to, oral, buccal, sublingual, pulmonary, transdermal, transmucosal, as well as subcutaneous, intraperitoneal, intravenous, and intramuscular injection. A preferred method of administering the mito-ATO compounds or pharmaceutical compositions of the present invention for treatment of cancer is by oral administration.

The term "effective amount" or "therapeutically effective amount" refers to an amount sufficient to effect beneficial or desirable biological and/or clinical results. That result can be reducing or inhibiting the growth of cancer cells, including drug-resistant or therapy resistant cancer cells, reducing, inhibiting or slowing metastasis of the cancer cells or invasiveness of the cancer cells or metastasis, or reducing, alleviating, or inhibiting at least one symptoms of the cancer or metastasis thereof, or any other desired alteration of a biological system. An "effective treatment" refers to treatment producing a beneficial effect, e.g., amelioration of at least one symptom of a cancer. A beneficial effect can take the form of an improvement over baseline, i.e., an improvement over a measurement or observation made prior to initiation of therapy according to the method. A beneficial effect can also take the form of reducing or inhibiting further growth of cancer cells, reducing or inhibiting metastasis of the cancer cells or invasiveness of the cancer cells or metastasis or reducing, alleviating, or inhibiting at least one symptoms of the cancer or metastasis thereof. Such effective treatment may, e.g., reduce patient pain, reduce the size of the tumor or number of cancer cells, may reduce or prevent metastasis of a cancer cell, or may slow cancer or metastatic cell growth.

In one embodiment, the therapeutically effective amount ranges from between about 0.1-50 mg/kg. A therapeutically effective amount of the mito-ATO compounds vary according to factors such as the disease state, age, sex, and weight of the subject, and the ability of mito-ATO compounds to elicit a desired response in the subject. Dosage regimens may be adjusted to provide the optimum therapeutic response. A therapeutically effective amount is also one in which any toxic or detrimental effects of the mito-ATO compounds of the present invention are outweighed by the therapeutically beneficial effects.

As described in the Examples below (e.g., Example 1) the alkyl chain length between the ATO and the TPP molecules plays a crucial role in determining the molecular mechanism function of the mito-ATO compounds described herein. For example, in some embodiments, it is demonstrated that longer alkyl chains (n>10) dramatically alters the mitochondrial target and inhibitory mechanism—from both complex 1 and complex 3 to exclusively complex 1 (as demonstrated in FIGS. 1C, 2B, and 6). Consequently, as demonstrated in FIG. 5, when the alkyl chain length is elongated (n>10), the immune modulatory function is not retained in mito-ATO compounds. As such, the present invention reveals new and unexpected molecular properties depending on the alkyl side chain length in Mito-ATO compounds (e.g., shorter chain lengths have more potent functionality). Further, we show that the inhibitory potency of tumor cell proliferation and tumor growth may also be increased by PEGglation of the side chain (e.g., mito-PEG-ATO compounds).

Increased Anti-Tumor Immune Response and T-Cell Activation

The disclosure further provides methods of increasing the anti-tumor immune response in a cancer patient, the method comprising administering the mito-ATO compound or composition in a therapeutically effective amount to increase the anti-tumor immune response with the patient.

Tumor cells create a microenvironment in which they can evade the host immune system, allowing the tumor cells to propagate and spread. One mechanism by which this occurs is the cancer cells evade the immune system (e.g., are not detected and/or not targeted by immune cells). This may occur via different mechanisms. For example, it has been shown that some cancer patients exhibit $CD4^+/CD25^+$ T cells, a subset of T cells often called regulatory T cells, which are known to reduce the T-cell immune response to the target (e.g., tumor antigens on tumor cells). Regulatory T cells produce high levels of IL-10 and TGF-β, thereby suppressing the immune system and allowing for evasion by the tumor (Shimizu et al., 1999).

The present inventors have found that the mito-ATO is able to increase the anti-tumor immune response to the cancer by modulating the immune response, particularly being able to modulated the amount of T regulatory cells vs T effector cells. Specifically, as demonstrated in the Examples, the administration of mito-ATO or a compositions comprising mito-ATO described herein is able to deplete the T-regulatory cells within the patient and to increase the number of T effector cells with the patient. This in turn leads to an increased immune response against the tumor, increasing the ability of the immune system to reduce the tumor cells with the patient.

The disclosure further provides methods of increasing a T cell response in a cancer patient, the method comprising administering the mito-ATO compound or composition in a therapeutically effective amount to increase the T cell response in a subject. "T cell response" refers to the effector T cell response against a tumor or tumor antigen. Effector T cells include cytotoxic T cells (CD8+ T-cells) and helper T cells (CD4+) T cells.

In some embodiments, the mito-ATO is administered to patient in combination with or to a patient undergoing an anti-cancer therapy that targets the patient's immune system, for example, an immunotherapy. In some embodiments, the anti-cancer therapy is a complex I inhibitor or a complex III inhibitor.

The term "anti-cancer therapy," "cancer therapy," and "anti-cancer drug" are used interchangeably to refer to therapeutics that are used for the treatment of cancer, including chemotherapy, immunotherapy, among others. Suitable anti-cancer therapies are known in the art and depend on the type of cancer being treated. Suitable anti-cancer therapies are described herein and include, for example mitochondrial inhibitors, including complex I or complex III inhibitors, checkpoint inhibitors, and chemotherapeutics.

As used herein, the terms "co-administration", "co-administered" and "in combination with", referring to the mito-ATO compounds and, optionally, the one or more other therapeutic agents, is intended to mean, and does refer to and include the following:

- simultaneous administration of such combination of compounds, when such components are formulated together into a single dosage form which releases said components at substantially the same time following administration,
- substantially simultaneous administration of such combination of compounds, when such components are formulated apart from each other into separate dosage forms which are administered at substantially the same time, where after said components are released at substantially the same time,
- sequential administration of such combination of compounds, when such components are formulated apart from each other into separate dosage forms which are administered at consecutive times with a significant time interval between each administration.

Kits

In another embodiment, the present disclosure provides a kit comprising a pharmaceutical composition comprising the mito-ATO compounds and instructional material. By "instructional material" we mean a publication, a recording, a diagram, or any other medium of expression which is used to communicate the usefulness of the pharmaceutical composition of the invention for one of the purposes set forth herein in a human. The instructional material can also, for example, describe an appropriate dose of the pharmaceutical composition. The instructional material of the kit of the invention can, for example, be affixed to a container which contains a pharmaceutical composition of the invention or be shipped together with a container which contains the pharmaceutical composition. Alternatively, the instructional material can be shipped separately from the container with the intention that the instructional material and the pharmaceutical composition be used cooperatively by the recipient.

In some embodiments, the kit may further comprise one or more anti-cancer therapies to use in combination with the mito-ATO compounds.

EXAMPLES

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

Example 1

Potent Inhibition of Tumour Cell Proliferation and Immunoregulatory Function by Mitochondria-Targeted Atovaquone The FDA-approved prophylactic antimalarial drug atovaquone (ATO) recently was repurposed as an antitumor drug. Studies show that ATO exerts a profound antiproliferative effect in several cancer cells, including breast, ovarian, and glioma. Analogous to the mechanism of action proposed in parasites, ATO inhibits mitochondrial complex III and cell respiration. To enhance the chemotherapeutic efficacy and oxidative phosphorylation inhibition, we developed a mitochondria-targeted triphenylphosphonium-conjugated ATO with varying alkyl side chains ($Mito_4$-ATO, $Mito_{10}$-ATO, $Mito_{12}$-ATO, and $Mito_{16}$-ATO). Results show, for the first time, that triphenylphosphonium-conjugated ATO potently enhanced the antiproliferative effect of ATO in cancer cells and, depending upon the alkyl chain length, the molecular target of inhibition changes from mitochondrial complex III to complex I. $Mito_4$-ATO and $Mito_{10}$-ATO inhibit both pyruvate/malate-dependent complex I and duroquinol-dependent complex III-induced oxygen consumption whereas $Mito_{12}$-ATO and $Mito_{16}$-ATO inhibit only complex I-induced oxygen consumption. Mitochondrial target shifting may have immunoregulatory implications.

Introduction

Atovaquone (ATO), a hydroxy-1,4-naphthoquinone analog of ubiquinone (Q), also known as coenzyme Q10 (FIG. 1A), is an FDA-approved antimicrobial drug used to treat *pneumocystis* pneumonia and to prevent and treat malaria caused by the parasites *Pnemocystis jirovecii* and *Plasmodium falciparum*; and toxoplasmosis infections in immune-compromised HIV patients.[1,2] ATO exerts antiviral effects, inhibiting arboviruses.[3] ATO is the first clinically approved drug that targets *Plasmodium* cytochrome $bc_1$ complex in mitochondria.[4] Also, ATO acts as a competitive inhibitor of mitochondrial complex III by displacing ubiquinol at the active site of the cytochrome $bc_1$ complex, inhibiting mitochondrial respiration and mitochondrial membrane potential in parasites and killing them.[5]

Recently, ATO was repurposed to target mitochondrial complex III in breast cancer cells, and results show that ATO inhibits proliferation of breast cancer stem-like cells.[6] The trans form of ATO is significantly more potent than the cis form. A similar mechanism of action (mitochondrial complex III inhibition) was proposed in breast cancer cells,[6] although the affinity of ATO to mitochondrial cytochrome $bc_1$ complex in mammalian cells is much lower than in parasites.[7] Targeting of ATO to mitochondrial complex III in ovarian cancer cells as a potential antitumor therapeutic strategy was proposed.[8] More recent studies show that ATO or ATO and proguanil (i.e., Malarone) exhibit antitumor activity both in animal models and in patients with acute myelogenous leukaemia and acute lymphocytic leukaemia.[9] Inhibition of tumour growth by ATO was attributed to inhibition of phosphorylation of signal transducer and activator of transcription 3 (STAT3).[10] ATO has been shown to inhibit glioblastoma cell proliferation, and inhibition of STAT3 by ATO as a viable therapy for glioblastoma multiforme was proposed.[10] However, the ATO concentration in the brain was suggested to be too low to be chemotherapeutically effective.

Little or no information exists on TPP+ modified mitochondrial complex III inhibitors. Thus, we modified the structure of ATO, an established complex III inhibitor, and developed triphenylphosphonium ($TPP^+$)-conjugated ATO (FIG. 1A) and investigated their antiproliferative and oxidative phosphorylation (OXPHOS) inhibitory effects in cancer cells.

The potent inhibition of mitochondrial complex III may have implications in the maintenance of the immunosuppressive function of regulatory T ($T_{reg}$) cells.[15] Although several relatively nontoxic mitochondrial complex I inhibitors[16] exist (other than rotenone [Rot], which is toxic), antimycin A is one of the few complex III inhibitors presently available. Developing potent mitochondrial complex III inhibitors is timely because of their ability to suppress $T_{reg}$ cells and enhance the levels of effector T ($T_{eff}$) cells.[15]

In the present study, we show that mitochondria-targeted ATO (Mito-ATO) analogs (FIG. 1) are significantly more potent than ATO in inhibiting pancreatic cancer cell proliferation. Our results also show, for the first time, that conjugating ATO to $TPP^+$ and increasing the aliphatic side chain length switches the molecular target in mitochondria from complex III/complex I to complex I for Mito-ATO analogs. As a result, $Mito_{12}$-ATO and $Mito_{16}$-ATO block mitochondrial respiration in pancreatic cancer cells by inhibiting only complex I and not complex III, whereas $Mito_4$-ATO and $Mito_{10}$-ATO inhibit oxygen consumption induced by both mitochondrial complex I and complex III. Potential implications of enhanced complex III inhibition induced by $Mito_4$-ATO and $Mito_{12}$-ATO in cancer immunosuppression are discussed.

Results

Figure 9:
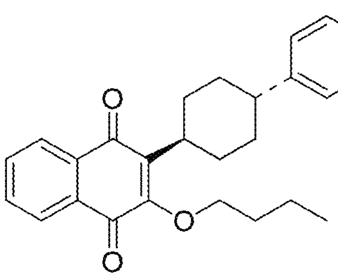
FIG. 9. Graph showing that both butyl-ATO and decyl-ATO devoid of $TPP^+$ were much less effective than their corresponding Mito-ATO analogs.
Figure 9:
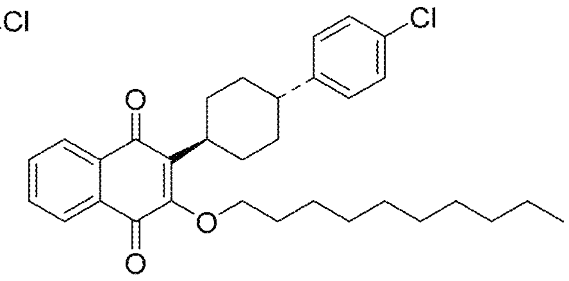
Figure 9:
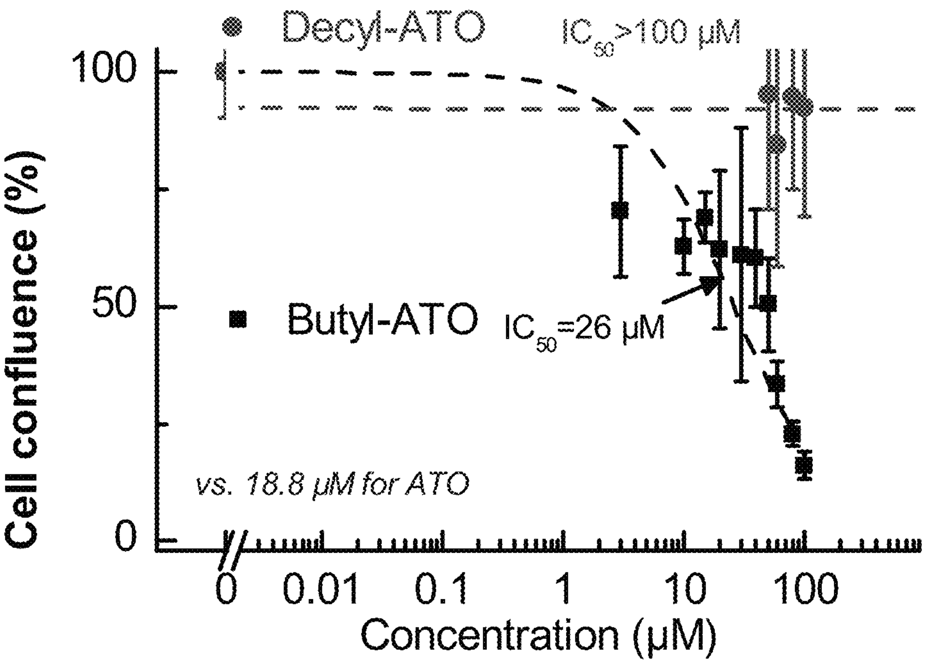

Mito-ATO Analogs are More Potent than ATO in Inhibiting MiaPaCa-2 Pancreatic Cancer Cell Proliferation Cell proliferation was monitored continuously in real time using an IncuCyte image analyser[11-13] and both ATO and Mito-ATO analogs (FIG. 1A). FIG. 1B shows the dose-dependent antiproliferative effects of ATO and $Mito_{10}$-ATO. $Mito_4$-ATO, $Mito_{12}$-ATO, and $Mito_{16}$-ATO also dose-dependently inhibited proliferation of MiaPaCa-2 pancreatic cancer cells. Mito-ATO analogs are more potent than ATO at inhibiting the proliferation of MiaPaCa-2 cells. FIG. 1C shows the cell confluence (indicated by a dotted line) as a function of Mito-ATO concentration, and the half maximal inhibitory concentration ($IC_{50}$) values of $Mito_4$-ATO, $Mito_{10}$-ATO, $Mito_{12}$-ATO, and $Mito_{16}$-ATO are 0.18 μM, 0.22 μM, 0.35 μM, and 3 μM, respectively. As compared with Mito-ATO analogs, ATO inhibited cell proliferation at much higher concentrations ($IC_{50}$=18 μM) (FIG. 1C). These results suggest that attaching an aliphatic chain containing a $TPP^+$ group to ATO greatly increases the antiproliferative potency. In control experiments, we used compounds (butyl-ATO and decyl-ATO) with an alkyl carbon-carbon side chain length similar to those of $Mito_4$-ATO and $Mito_{10}$-ATO but lacking the $TPP^+$. As shown in FIG. 9, both butyl-ATO and decyl-ATO devoid of $TPP^+$ were much less effective than their corresponding Mito-ATO analogs.

Figure 2:
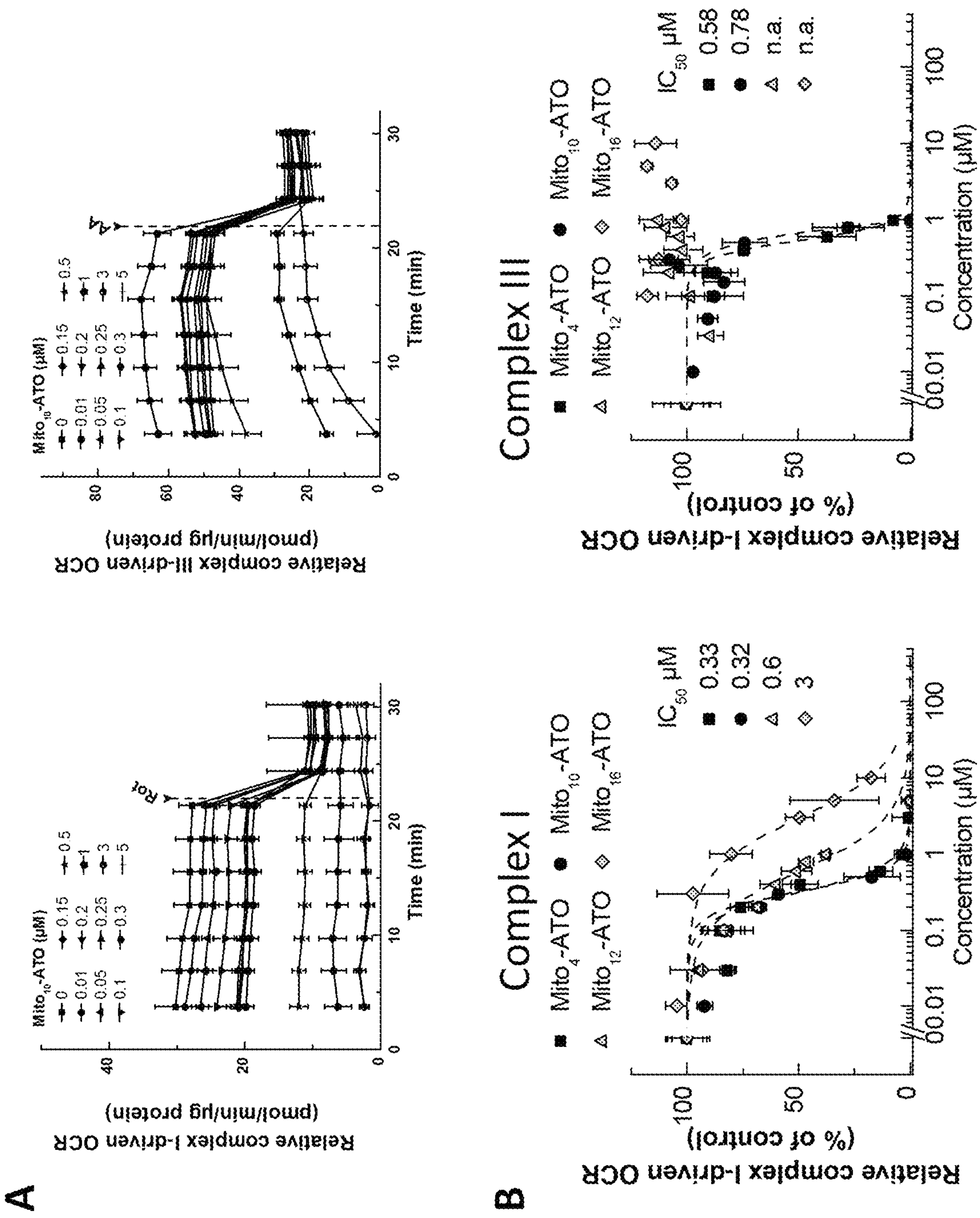
FIG. 2. Effects of Mito-ATO analogs on the oxygen consumption induced by mitochondrial complexes I and III. (A) Dose-dependent effect of $Mito_{10}$-ATO on complex I- and complex III-dependent oxygen consumption was measured in MiaPaCa-2 cells. MiaPaCa-2 cells were treated with Mito-ATO for 24 h. Relative complex I (1.5 mM malate, 10 mM pyruvate, 10 mM ADP)-driven OCR (left) and relative complex III (0.5 mM duroquinol, 10 mM ADP)-driven OCR (right) were monitored by XF-96 analyser. Either Rot (complex I inhibitor) or antimycin A (AA, complex III inhibitor) was acutely added and OCR assayed immediately. (B) The mitochondrial complex I (left) and III (right) driven OCR (calculated as Rot or AA inhibitable OCR) are plotted against the concentration of ATO and Mito-ATO analogs. Dashed lines represent the fitting curves used for determination of the $IC_{50}$ values. (n.a., not applicable).

Inhibitory Effects of Mito-ATO Analogs on Mitochondrial Complex Activities in MiaPaCa-2 Cells The mitochondrial complex activities were assessed by measuring the oxygen consumption rate (OCR) using the Seahorse technique.[6,11-4] MiaPaCa-2 cells were treated separately with Mito-ATO analogs at different concentrations for 24 h and OCR was measured. As shown in FIG. 2A, $Mito_{10}$-ATO effectively inhibits complex III-induced oxygen consumption and, more importantly, $Mito_{10}$-ATO caused a significantly greater inhibition of mitochondrial complex I-driven oxygen consumption. The $IC_{50}$ value for $Mito_{10}$-ATO to inhibit oxygen consumption by complex I is 0.32 μM, and the $IC_{50}$ value for $Mito_{10}$-ATO to inhibit oxygen consumption by complex III is 0.78 μM (FIG. 2B). $Mito_4$-ATO and $Mito_{10}$-ATO potently inhibit both mitochondrial complex I- and complex III-induced oxygen consumption. However, $Mito_{12}$-ATO and $Mito_{16}$-ATO did not inhibit complex III-induced oxygen consumption; they inhibited only the complex I-induced oxygen consumption (FIG. 2B). These results show that there is a shift in mitochondrial targeting of Mito-ATO analogs that is dependent on the alkyl side chain length attached to $TPP^+$.

Relative Uptake of $Mito_{10}$-ATO and ATO into MiaPaCa-2 and A549 Cells

Figure 10:
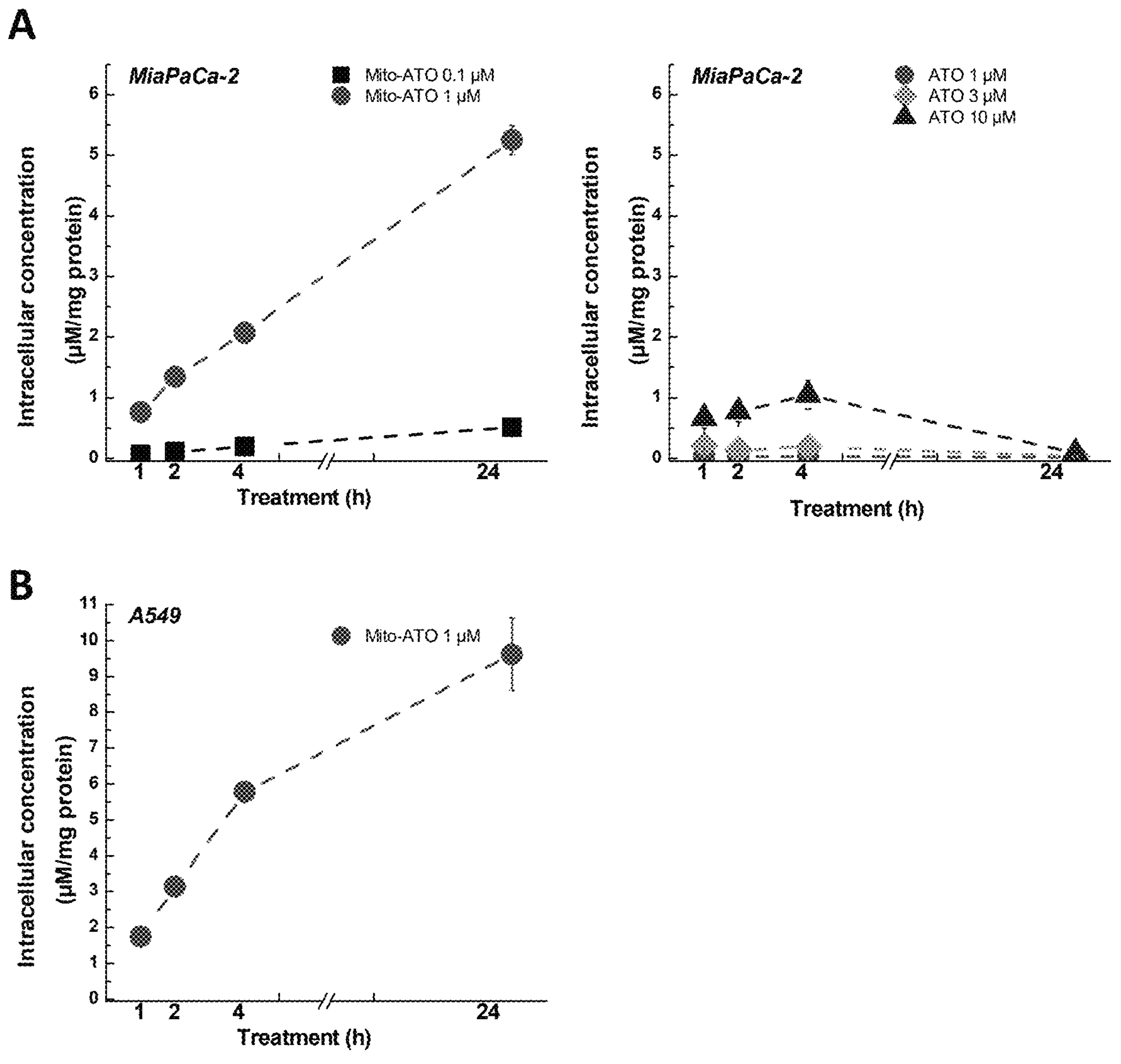
FIG. 10. Liquid chromatography with tandem mass spectrometry (LC-MS/MS) technique to investigate the relative uptake of $Mito_{10}$-ATO and ATO in (A) MiaPaCa-2 and (B) A549 cells.

Next, we used the liquid chromatography with tandem mass spectrometry (LC-MS/MS) technique to investigate the relative uptake of $Mito_{10}$-ATO and ATO in MiaPaCa-2 and A549 cells (FIG. 10). Cells were treated with $Mito_{10}$-ATO (0.1 μM and 1 μM) or ATO (1-10 μM) for 1, 2, 4, and 24 h. As shown in FIG. 10, there was an increase in cellular uptake of $Mito_{10}$-ATO that accumulated inside the cells with time. Under the same treatment period with even with higher concentrations (up to 10 μM), ATO uptake was considerably lower and did not accumulate in cancer cells over a 24 h period.

Figure 3:
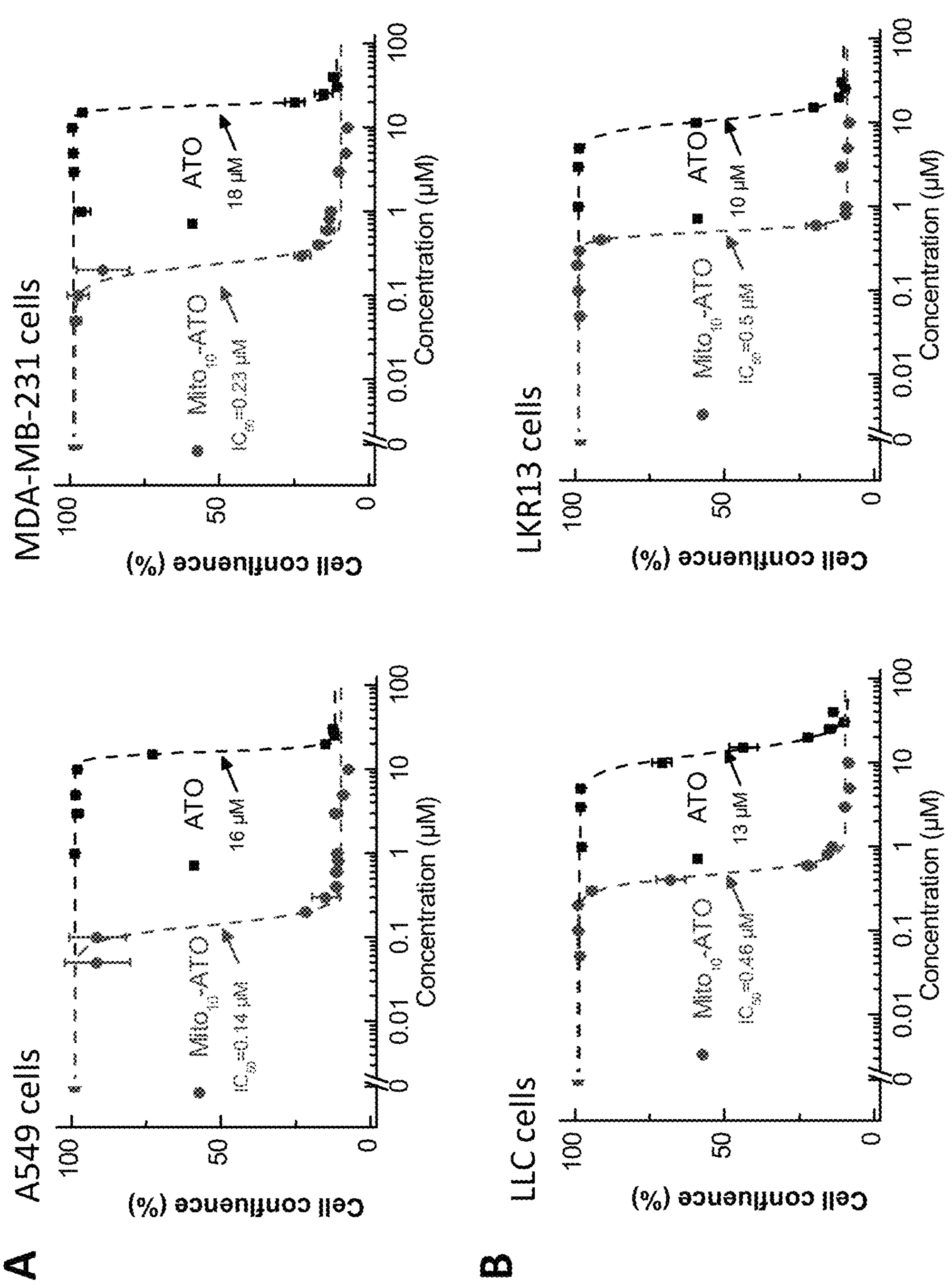
FIG. 3. Effects of ATO and Mito-ATO on proliferation in human cancer cells and mouse cancer cells. A549 human lung and MDA-MB-231 breast cancer cells (A) and LLC and LKR13 mouse lung cancer cells (B) were treated with ATO and $Mito_{10}$-ATO. Cell proliferation was monitored in real-time with the continuous presence of indicated treatments until the end of each experiment. The cell confluence (as control groups reach 98% confluency) is plotted against concentration. Dashed lines represent the fitting curves used to determine the $IC_{50}$ values as indicated.
Figure 4:
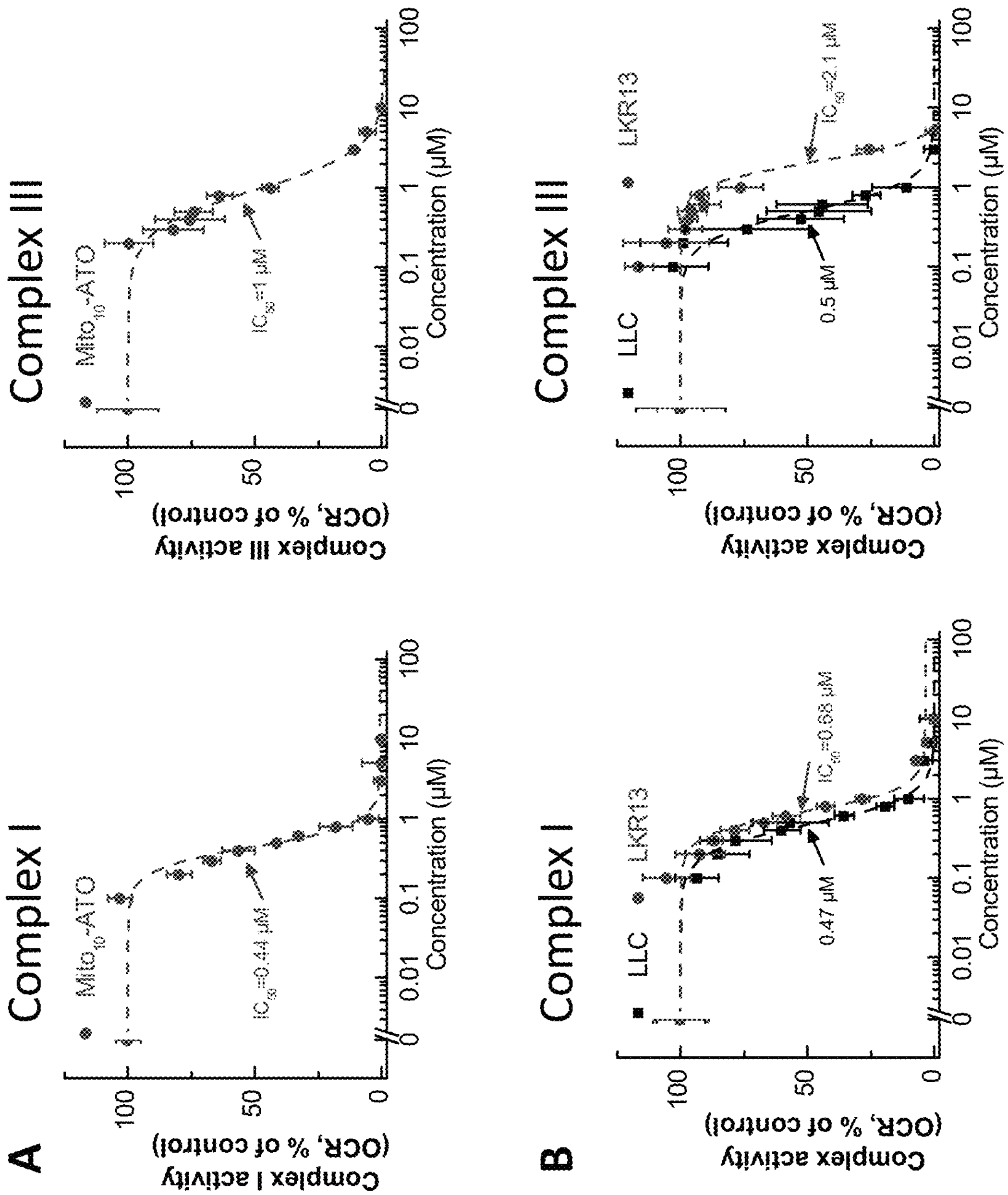
FIG. 4. Effects of $Mito_{10}$-ATO on the oxygen consumption induced by mitochondrial complexes I and III in human cancer cells and mouse cancer cells. A549 human lung cancer cells (A), and LLC and LKR13 mouse lung cancer cells (B) were treated with $Mito_{10}$-ATO. The mitochondrial complex I (left) and complex III (right)-driven OCR (calculated as Rot or AA inhibitable OCR) are plotted against concentration of $Mito_{10}$-ATO. Dashed lines represent the fitting curves used for determination of the $IC_{50}$ values.

Inhibitory Effects of $Mito_{10}$-ATO on Proliferation of Breast and Lung Cancer Cells Previous reports provide evidence for enhanced uptake of several mitochondria-targeted cationic agents into cancer cells as compared with non-transformed control cells.[11-14] We examined the effect of ATO and $Mito_{10}$-ATO on A549 human lung cancer cells and MDA-MB-231 human breast cancer cells (FIG. 3A) and on LLC and LKR13 mouse lung cancer cells (FIG. 3B). $Mito_{10}$-ATO was effective at halting cell proliferation in A549 and MDA-MB-231 human cancer cells and in LLC and LKR13 mouse lung cancer cells. As shown in FIG. 3, $Mito_{10}$-ATO also was more potent than ATO in inhibiting cancer cell proliferation. $Mito_{10}$-ATO inhibited both mitochondrial complex I- and III-induced oxygen consumption in these cells (FIG. 4). These results demonstrate that the enhanced antiproliferative potency of Mito-ATO analogs is not restricted to a single cancer cell type and is broadly applicable to several cancer cells.

Immunomodulatory Effects of $Mito_4$-ATO, $Mito_{10}$-ATO, and $Mito_{12}$-ATO

Figure 5:
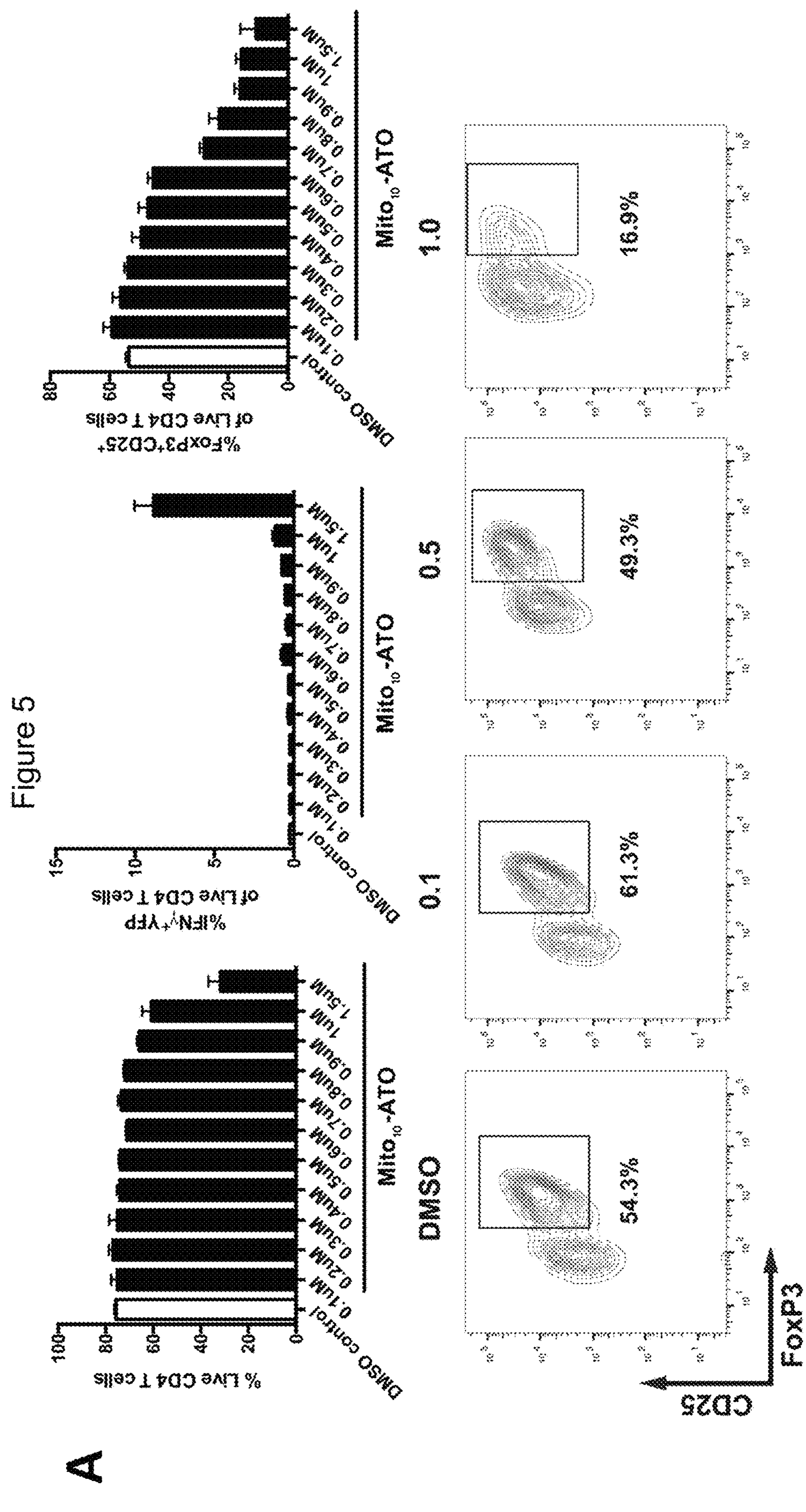
FIG. 5. In vitro differentiation of $CD4^+$ T regulatory cells under varying concentrations of Mito-ATOs and controls. After six days of culture, cells were stained for flow cytometry analysis. (left) Live/dead staining to assess the percentage of live CD4+ T cells within the lymphocyte gate. (middle) $T_{eff}$ cell function is shown as the frequency of IFNγ-GFP positive cells within the live $CD4^+$ T cells. (right) The percentage of $T_{reg}$ cells is shown as the frequency of $FoxP3^+CD25^+$ cells within the live $CD4^+$ T cells. (A, bottom) Effects of $Mito_{10}$-ATO on $T_{reg}$ ($FoxP3^+CD25^+$) cells within the $CD4^+$ T cell gate (contour plots generated from panel A, upper right). $Mito_4$-ATO (B) effectively suppressed $T_{reg}$ while $Mito_{12}$-ATO (C), Butyl-ATO (D), Decyl-ATO (D), and ATO (E) did not suppress $T_{reg}$ cells.
Figure 5:
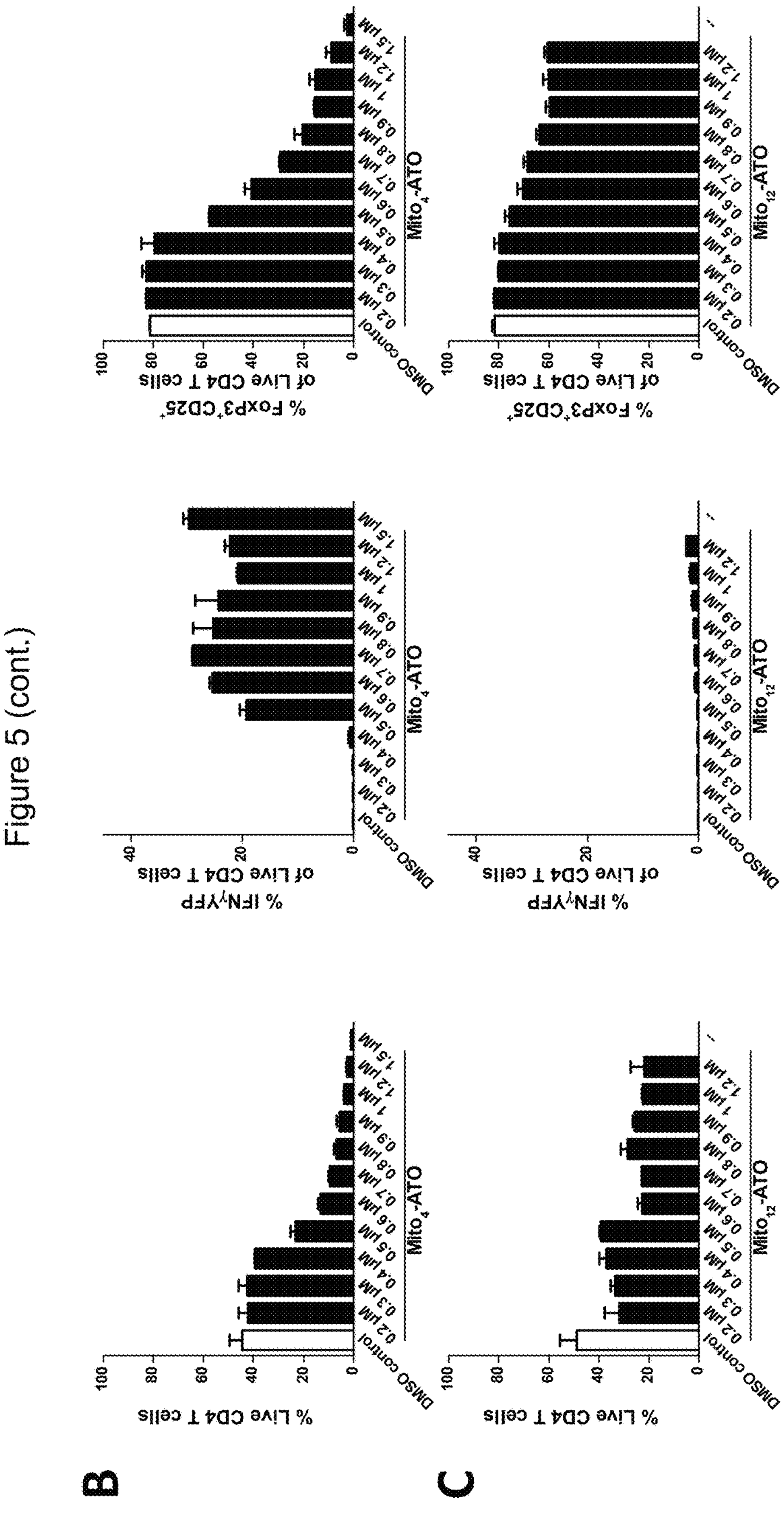
Figure 5:
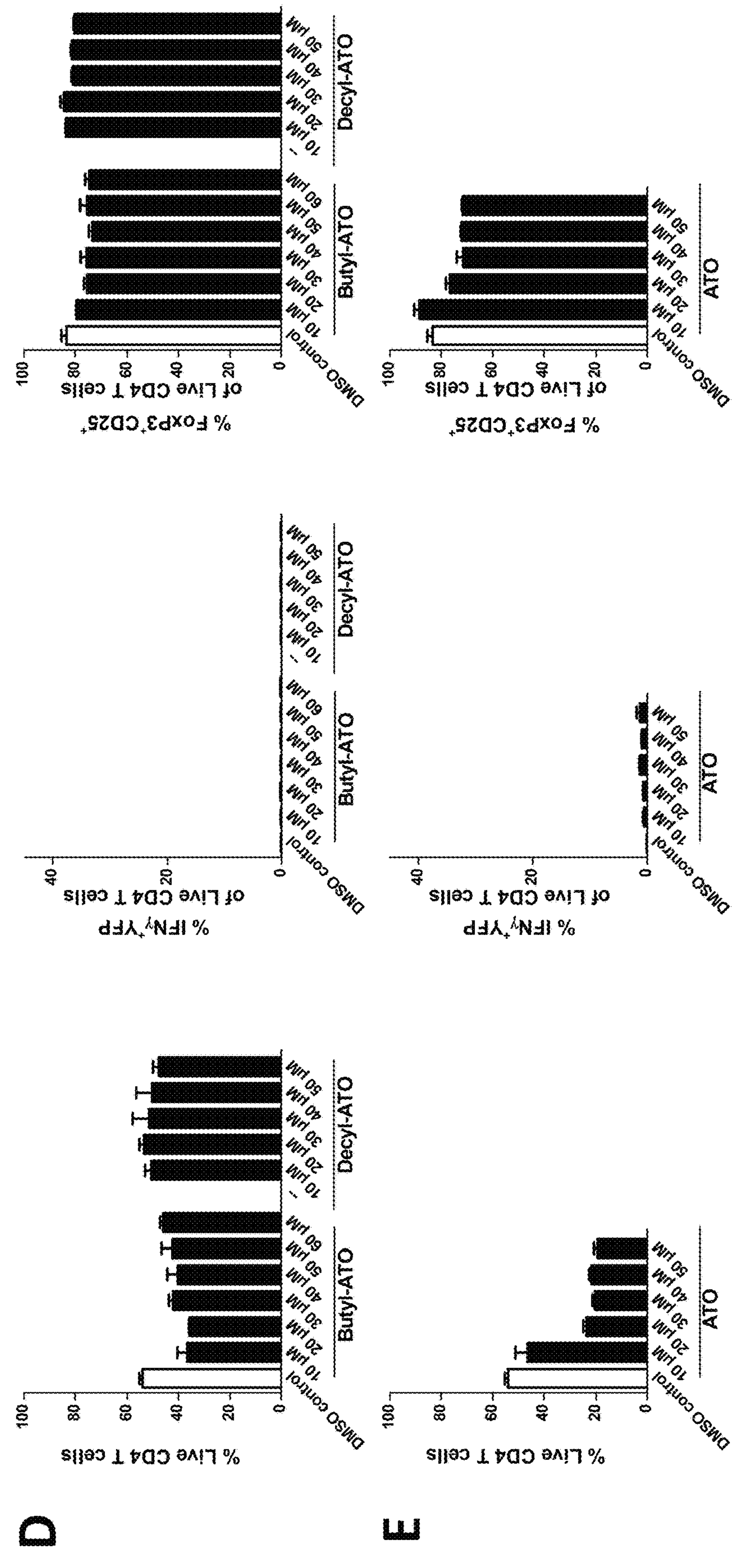

Recent reports indicate that selective targeting and inhibiting of mitochondrial complex III mitigate and reverse immunosuppression by $T_{reg}$ cells, promoting the function of $T_{eff}$ cells.[15,17] To investigate the effects of $Mito_4$-ATO, $Mito_{10}$-ATO, and $Mito_{12}$-ATO on $T_{eff}$ versus $T_{reg}$ cells, activated $CD4^+$ T cells were isolated from SMARTA triple reporter mice, activated, and cultured in vitro with TGFβ (5 ng/mL) and IL-2 (100 μg/mL), as described in the Materials and Methods section. The $CD4^+$ T cells were treated with ATO and Mito-ATO analogs at varying concentrations (FIG. 5). After six days, cells were stained to assess viability, phenotype, and function using the flow cytometry. Results demonstrate that Mito$_4$-ATO (FIG. 5B) and Mito$_{10}$-ATO (FIG. 5A) inhibited Foxp3$^+$ $T_{reg}$ differentiation and/or survival and promoted $T_{eff}$ cell IFNγ production in a dose-dependent manner. In contrast, Mito$_{12}$-ATO did not appreciably inhibit $T_{reg}$ differentiation (FIG. 5C). Mito$_4$-ATO and Mito$_{10}$-ATO potently inhibited mitochondrial complex I- and complex III-driven oxygen consumption. Mito$_{12}$-ATO strongly inhibited oxygen consumption by complex I but not complex III-driven oxygen consumption. Thus, it is plausible that that inhibition of $T_{reg}$ and stimulation of $T_{eff}$ response by Mito$_4$-ATO and Mito$_{10}$-ATO are mediated by their increased potency to target mitochondrial complex III. Furthermore, ATO, butyl-ATO, and decyl-ATO (up to 60 μM) did not inhibit $T_{reg}$ differentiation and/or survival (FIGS. 5D and E).

Discussion

The Relative Hydrophobicity of ATO, Mito-ATO, and Alkyl-ATO

Figure 14:
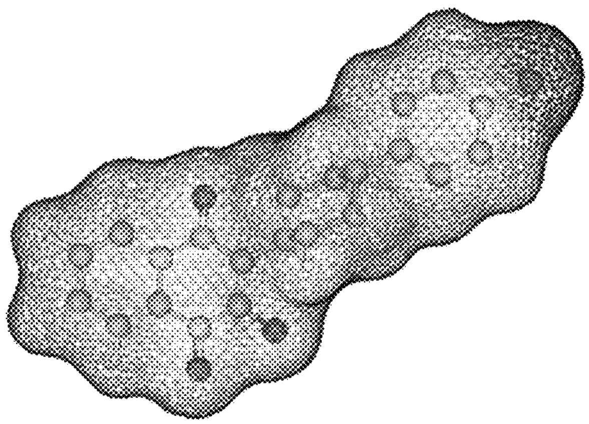
FIG. 14 demonstrates the relative hydrophobic regions in ATO and Mito-ATO analogs.
Figure 14:
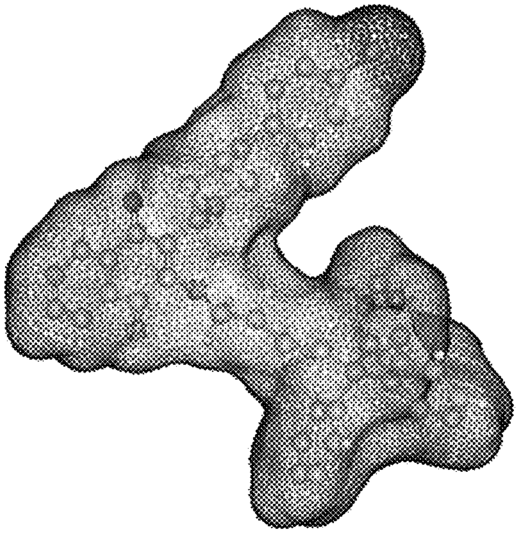
Figure 14:
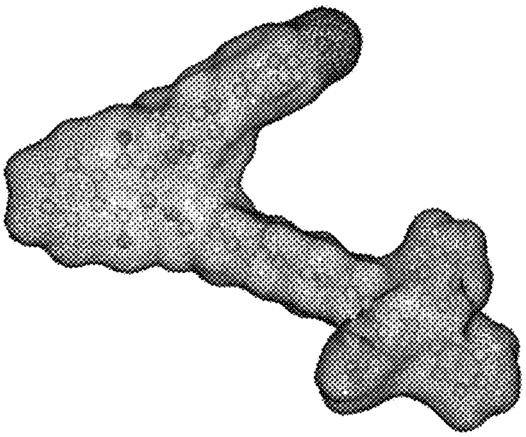
Figure 14:
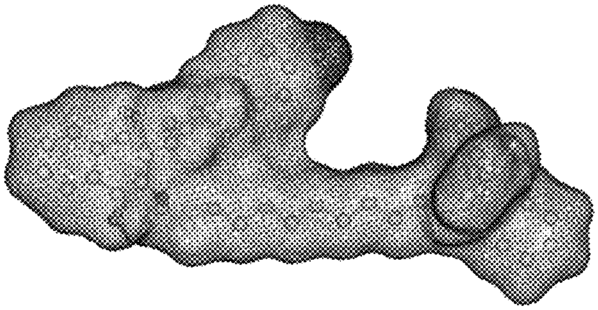
Figure 14:
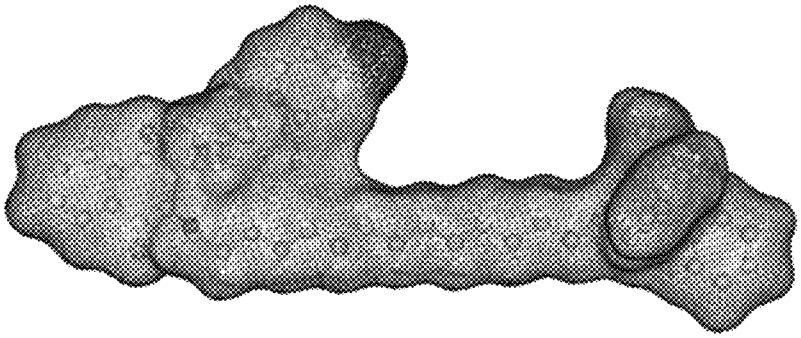
Figure 14:
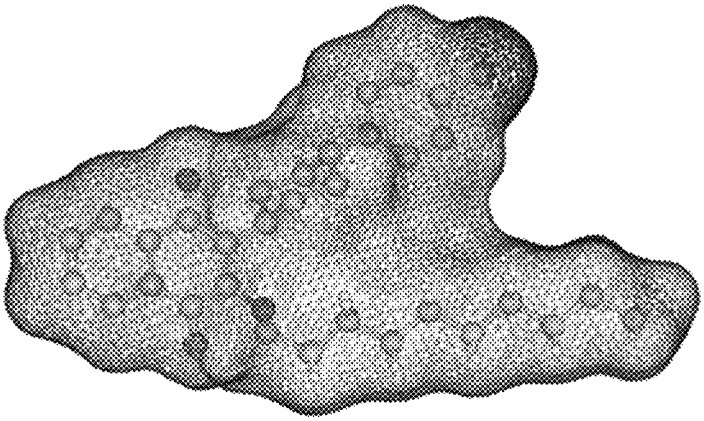
Figure 14:
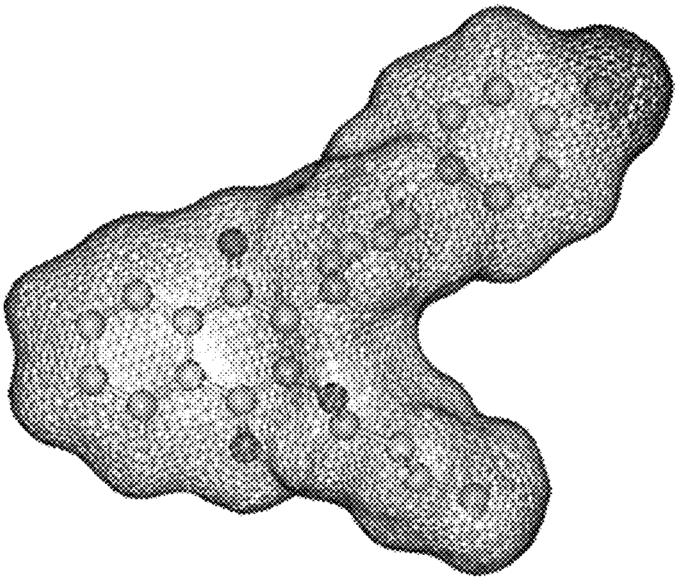

The lipophilicity of ATO was attributed to its stabilization in the hydrophobic pocket of the cytochrome bc$_1$ complex.[5] To assess the relative hydrophobicity of ATO and Mito-ATO analogs, we calculated the octanol/water partition coefficients (log P) using a QSAR analysis and rational drug design as a measure of molecular hydrophobicity (Table 1, FIG. 14). This method also uses a consensus model built using the ChemAxon software (San Diego, CA).[18,19] Table 1 and FIG. 14 list the log P values along with the calculated regions of the relative hydrophilic and hydrophobic regions. As shown in Table 1 and FIG. 14, there was a significant increase in the hydrophobicity of Mito-ATO (as compared with ATO) with the increasing alkyl side chain length (from C-4 to C-16).

TABLE 1

Calculated partition coefficients in ATO and Mito-ATO analogs.

| Molecules | Structure | Log P |
|---|---|---|
| ATO | 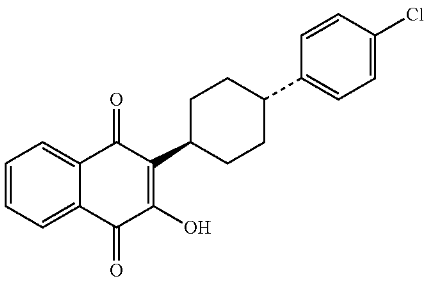 [SMILES: O=C1C(O)=C([C@H]2CC[C@H](c3ccc(Cl)cc3)CC2)C(=O)c2ccccc21] | 5.1 |
| Mito$_4$-ATO | 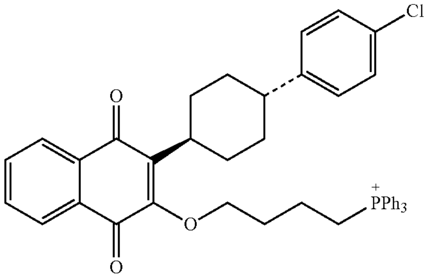 | 10.1 |
| Mito$_{10}$-ATO | 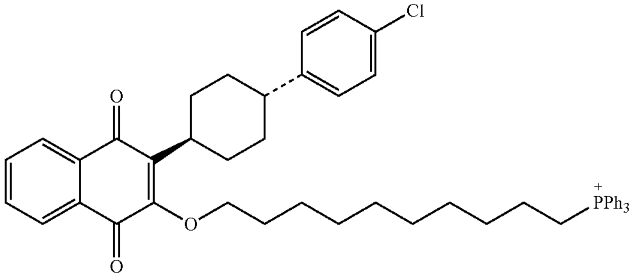 | 12.8 |
| Mito$_{12}$-ATO | 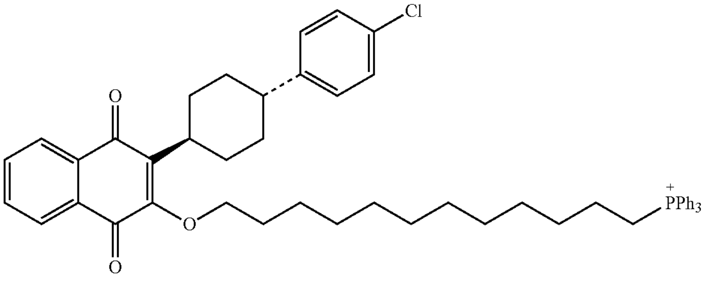 | 13.7 |

TABLE 1-continued

Calculated partition coefficients in ATO and Mito-ATO analogs.

| Molecules | Structure | Log P |
|---|---|---|
| $Mito_{16}$-ATO | 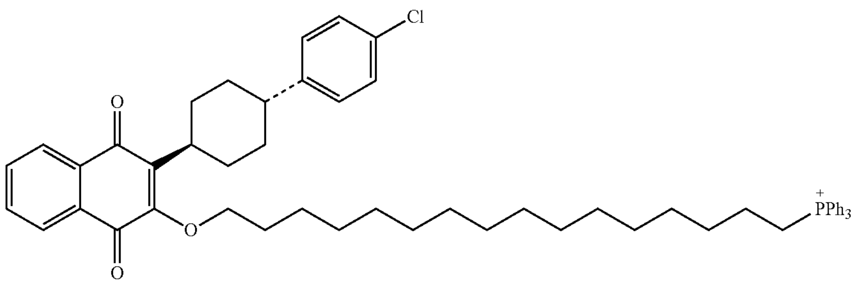 | 15.5 |
| Decyl-ATO | 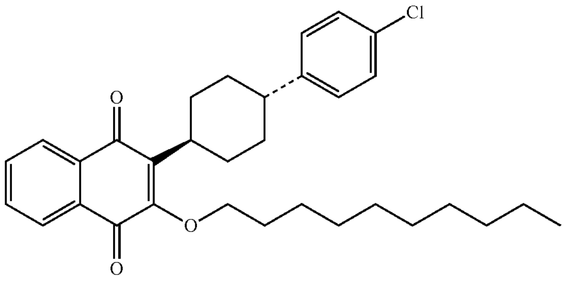 [SMILES: CCCCCCCCCCOC1=C([C@H]2CC[C@H](c3ccc(Cl)cc3)CC2)C(=O)c2ccccc2C1=O] | 9.1 |
| Butyl-ATO | 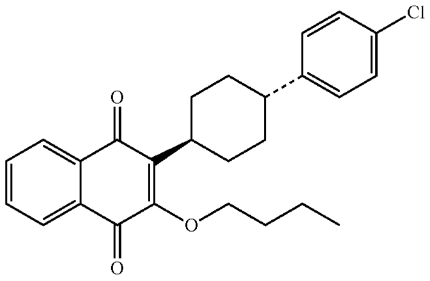 [SMILES: CCCCOC1=C([C@H]2CC[C@H](c3ccc(Cl)cc3)CC2)C(=O)c2ccccc2C1=O] | 6.4 |

Inhibition of Cytochrome $Bc_1$ by ATO: Stabilizing Molecular Interactions at the Active Site Previous studies showed that ATO binds to the mitochondrial cytochrome $bc_1$ complex (ubiquinol cytochrome c oxidoreductase or complex III) and inhibits its activity.[5,20] We report here that structural modification of ATO by attachment of $TPP^+$ to ATO (Mito-ATOs) greatly inhibits tumour cell proliferation. Both $Mito_4$-ATO and $Mito_{10}$-ATO potently inhibit oxygen consumption by complex I and complex III (FIG. 6A). Surprisingly, $Mito_{12}$-ATO (with a 12-carbon side chain) and $Mito_{16}$-ATO (with a 16-carbon side chain) only inhibited complex I but not complex III-driven oxygen consumption (FIG. 6B). Conceivably, the lack of effect of $Mito_{12}$-ATO and $Mito_{16}$-ATO on oxygen consumption by complex III suggests that $Mito_{12}$-ATO and $Mito_{16}$-ATO do not target the Qo site of the cytochrome bc1 complex.

ATO is structurally similar to Q and acts as a competitive inhibitor of Q. Modelling and energy minimization studies show that ATO docks into the Qo active site stabilized by hydrophobic and hydrogen bonding interactions with the Rieske protein and the cytochromes.[5,21] Q is reduced to ubiquinol (QH2) by complexes I and II and oxidized to Q at the catalytic site of complex III. Based on published reports on the molecular basis of the antimalarial action of ATO,[5] a similar mechanism is proposed for ATO inhibition of respiration of cancer cells. ATO acts as a competitive Qo site-specific inhibitor of cytochrome $bc_1$ complex oriented between the [2Fe-2S] cluster of the Rieske protein. ATO is stabilized in this pocket through the polarized hydrogen bonding interaction between the oxygen atom (O) of the ionized form and the protonated nitrogen atom of the His181 side chain of the Rieske protein.

The evidence for the binding of ATO to the Rieske iron-sulphur centre came from electron paramagnetic resonance (EPR) spectroscopy and circular dichroism spectroscopy studies of the purified cytochrome $bc_1$ complex from the yeast *Saccharomyces cerevisiae*.[4] The addition of ATO shifted the ascorbate-reduced Rieske centre signals (at gz and gx to a higher field and the gy component to a lower field). The extent of the magnetic field shifts in the EPR spectra of the reduced Rieske Fe—S centre indicates a change in the electronic environment of the 2Fe-2S cluster due to ATO binding.[4] The low-temperature EPR of the yeast system may be suitable for investigating the effect of alkyl side chain length in Mito-ATO (e.g., $Mito_4$-ATO, $Mito_{10}$-ATO, $Mito_{12}$-ATO, or $Mito_{16}$-ATO) and the Rieske iron-sulphur cluster.

It is plausible that, depending on the length of the aliphatic substituent attached to the $TPP^+$ group in Mito-ATO, some Mito-ATO analogs ($Mito_4$-ATO or $Mito_{10}$-ATO) may be stabilized at the cytochrome $bc_1$ pocket by several hydrophobic/aromatic interactions between the ATO moiety and the amino acid residues within the binding site. Mito-ATO is much more hydrophobic than ATO. It accumulates into cancer cell mitochondria more effectively than ATO and inhibits mitochondrial respiration and cancer cell proliferation more potently than ATO.

Figure 6:
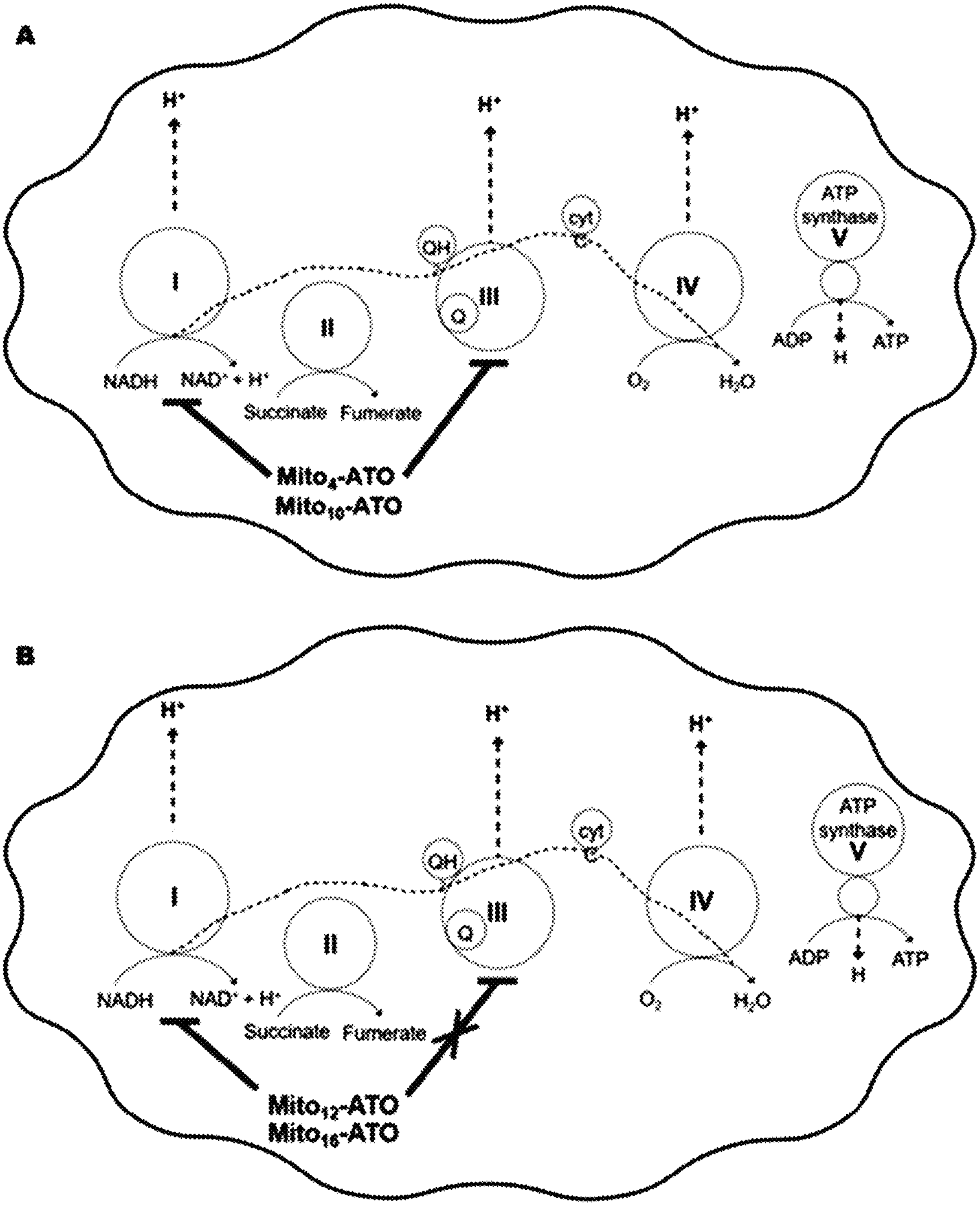
FIG. 6. Mitochondrial targeting of Mito-ATOs with varying side chain lengths. This figure illustrates (A) the dual mitochondrial targeting (complex I and complex III) of $Mito_4$-ATO and $Mito_{10}$-ATO and (B) a shift in mitochondrial targeting from complex III to complex I for $Mito_{12}$-ATO and $Mito_{16}$-ATO in MiaPaCa-2 cells.

Results using $Mito_{12}$-ATO indicate that it does not inhibit complex III-dependent oxygen consumption. However, $Mito_{12}$-ATO potently inhibits complex I-driven oxygen consumption (FIG. 6). This, combined with the finding that $Mito_{12}$-ATO does not inhibit $T_{reg}$ cells, implies that the alkyl side chain length in Mito-ATO plays an important role in mitochondrial targeting and immunoregulatory effects.[22]

Cancer Immunosuppression and Mito-ATO

The number of $T_{reg}$ cells is reportedly increased in the microenvironments of most cancers (e.g., pancreatic cancer, lung cancer).[23,24] There is negative correlation between $T_{reg}$ levels and survival in cancer patients.[25] $T_{reg}$ cells suppress antitumor immunity, thereby hampering immunotherapy.[26] Drug therapy targeting $T_{reg}$ cells is emerging as a promising antitumor approach.[27,28] Emerging research shows that mitochondrial respiratory chain activity, particularly mitochondrial complex III activity, is crucial for preserving the antitumor function of $T_{reg}$ cells.[29] Alternatively, $T_{reg}$ cells devoid of complex III had decreased immunoregulatory function.[15] It is conceivable that Mito-ATO analogs with the appropriate substituents and aliphatic side chain lengths will be able to inhibit $T_{reg}$ cell respiration and activate cancer immunotherapy.

Clearly, the discovery that increasing alkyl chain length in Mito-ATO, a new class of small-molecule OXPHOS inhibitors, changes the mitochondrial respiratory complex target is significant in corroborating the role of complex III-dependent metabolic alterations (i.e., accumulation of oncometabolite 2-hydroxyglutarate [2-HG] and succinate) in repressing alpha-ketoglutarate-dependent demethylases and DNA hypermethylation.[15] Previously, it was shown that loss or inhibition of mitochondrial complex III in cancer cells results in increased levels of 2-HG and succinate.[15,17] Antimycin A increased the levels of succinate and 2-HG in $T_{reg}$ cells.[15] Our Initial attempts to measure mitochondrial complex activities, using the Seahorse technique, in intact and permeabilized T cells were not successful. Several experimental conditions (e.g., cell concentration, permeabilizing conditions) need to be optimized before reliable oxygen consumption rate measurements can be made. To further corroborate the role of mitochondrial complex III, it would be of interest to compare the effects of ATO, $Mito_4$-ATO, $Mito_{10}$-ATO, $Mito_{12}$-ATO, and $Mito_{16}$-ATO on inducing the transcriptional programs responsible for metabolic alterations in cancer cells and immune cells.[15,17]

In this study, we showed that $TPP^+$-conjugated ATO analogs ($Mito_4$-ATO, $Mito_{10}$-ATO, $Mito_{12}$-ATO, and $Mito_{16}$-ATO) are considerably more potent than the parent drug, ATO, at inhibiting the proliferation of pancreatic and other cancer cell types. $Mito_4$-ATO and $Mito_{10}$-ATO but not $Mito_{12}$-ATO suppress $T_{reg}$ function. The molecular targets of Mito-ATO analogs in the mitochondrial respiratory chain are different depending on the alkyl side chain length. $Mito_4$-ATO and $Mito_{10}$-ATO inhibit mitochondrial oxygen consumption by complex I and complex III, whereas $Mito_{12}$-ATO and $Mito_{16}$-ATO inhibit only the complex I-induced oxygen consumption. Interestingly, the alkyl side chain length in Mito-ATOs influences their mitochondrial targeting and inhibition of oxygen consumption.

Materials and Methods for Example 1

General

All chemicals and organic solvents were commercially available and were used as supplied. The reactions were monitored by thin layer chromatography using silica gel Merck $^{60}$F254. Crude materials were purified by flash chromatography on Merck silica gel 60 (0.040-0.063 mm). $^{31}$P NMR, $^{1}$H NMR and $^{13}$C NMR spectra were recorded at 400 and 75 MHz spectrometers, respectively. $^{1}$H NMR spectra were recorded using a Bruker DPX AVANCE 400 spectrometer equipped with a quattro nucleus probe. Chemical shifts (δ) are reported in ppm and J values in Hertz.

Figure 8:
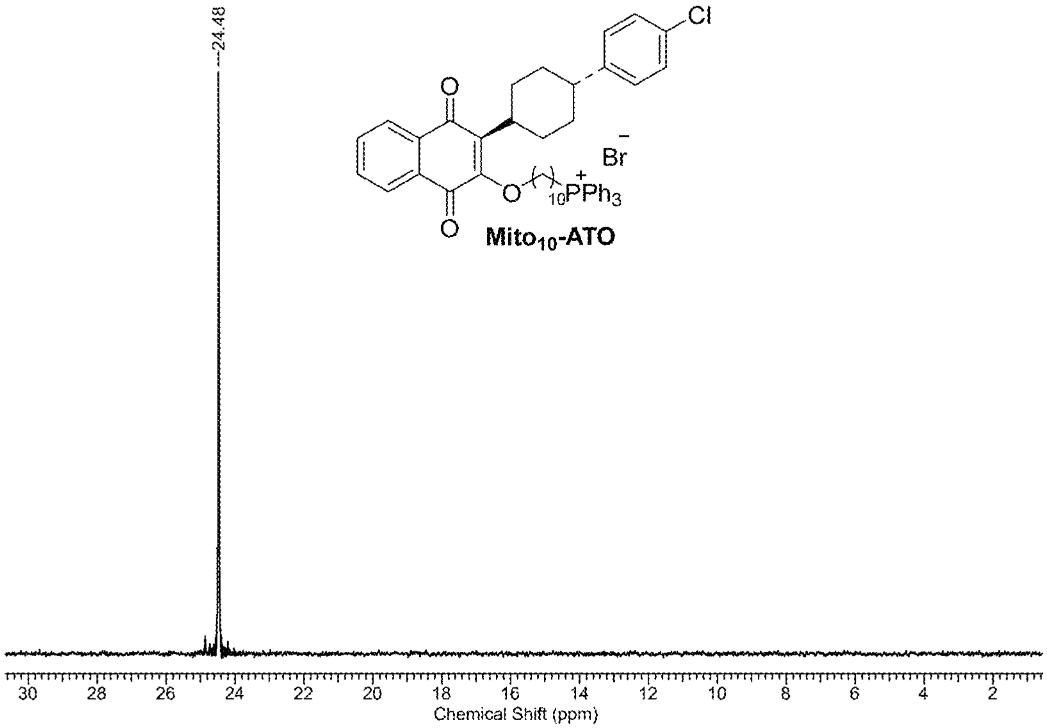
FIG. 8. NMR spectra and related parameters of the $Mito_n$-ATO disclosed herein.
Figure 8:
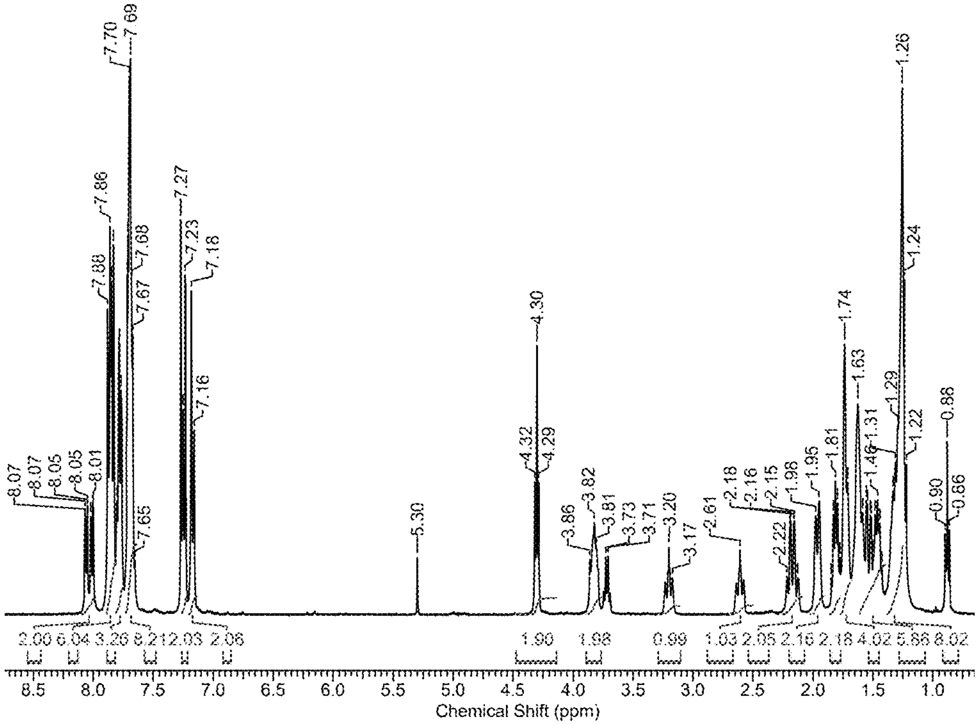
Figure 8:
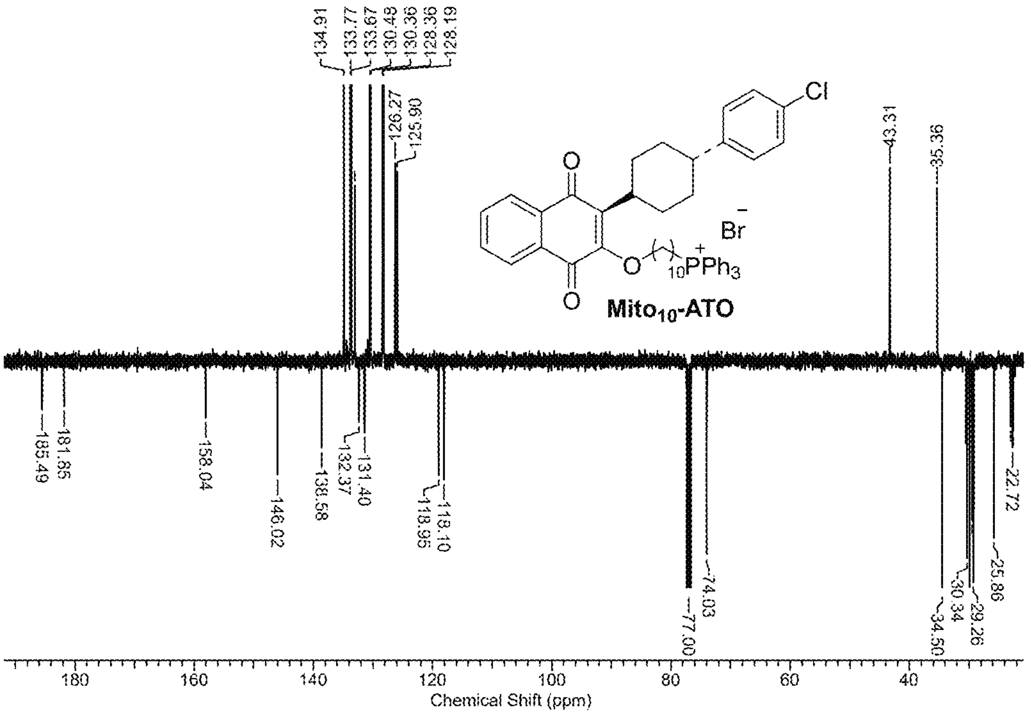
Figure 8:
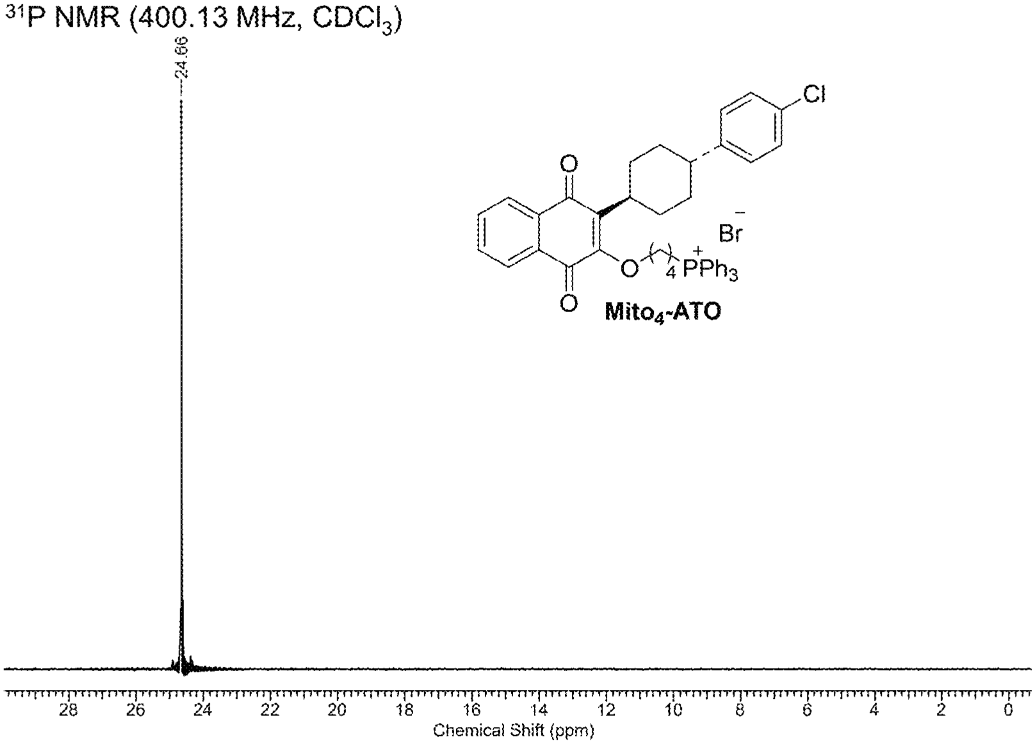
Figure 8:
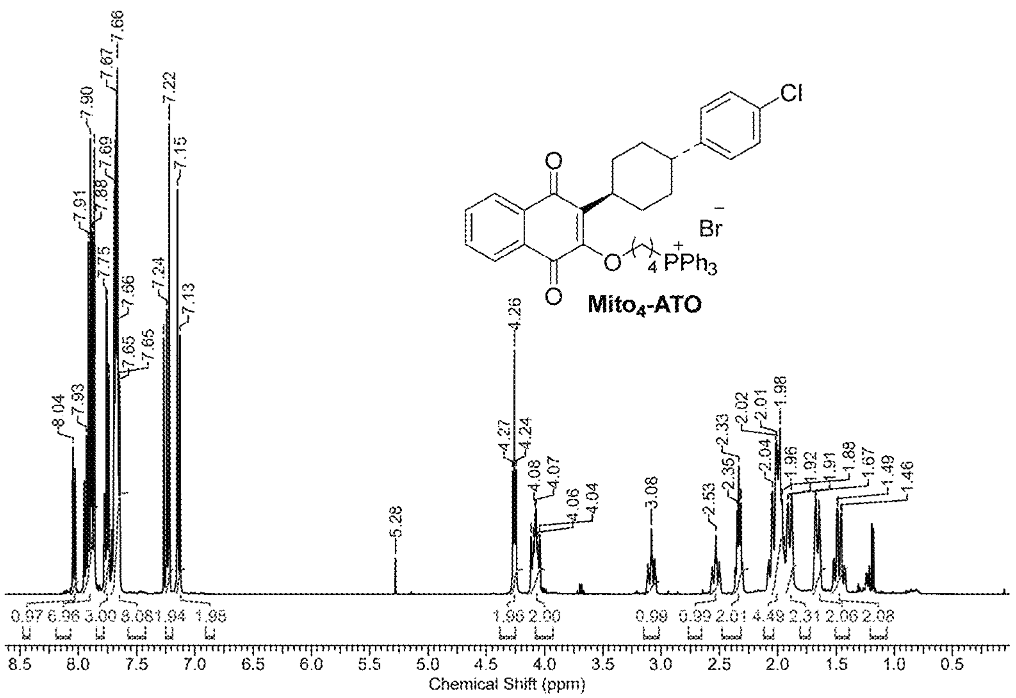
Figure 8:
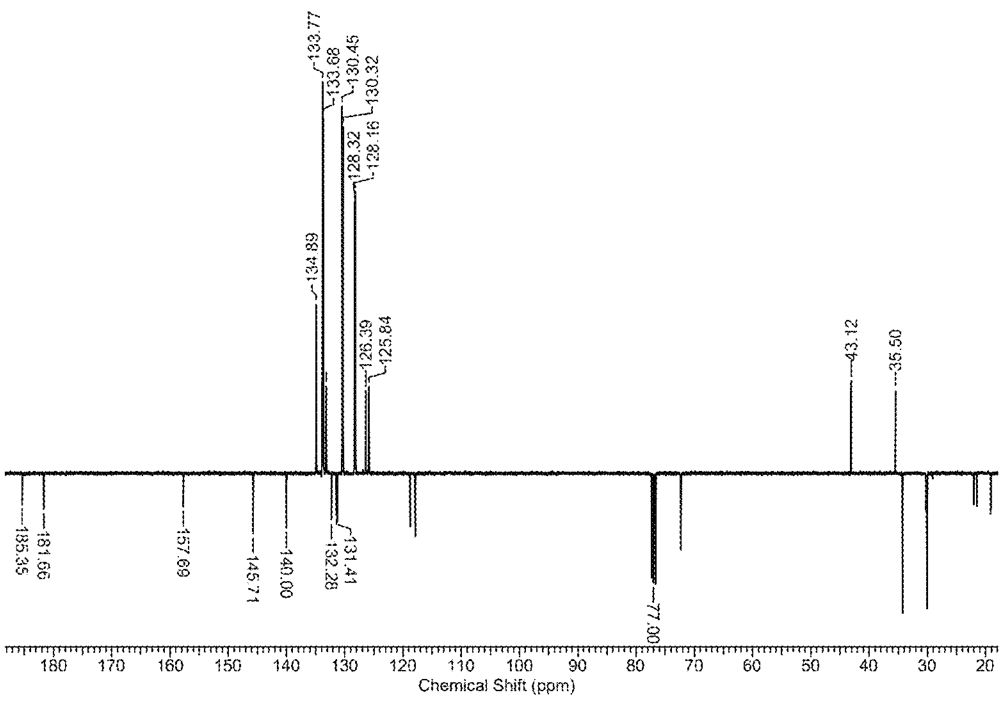
Figure 8:
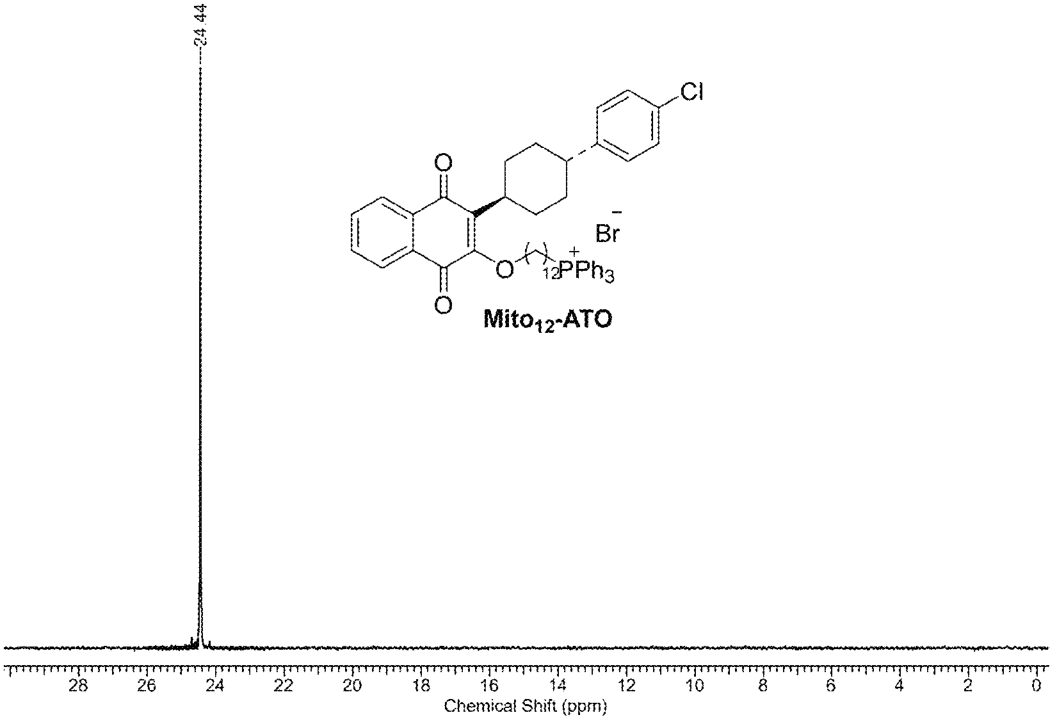
Figure 8:
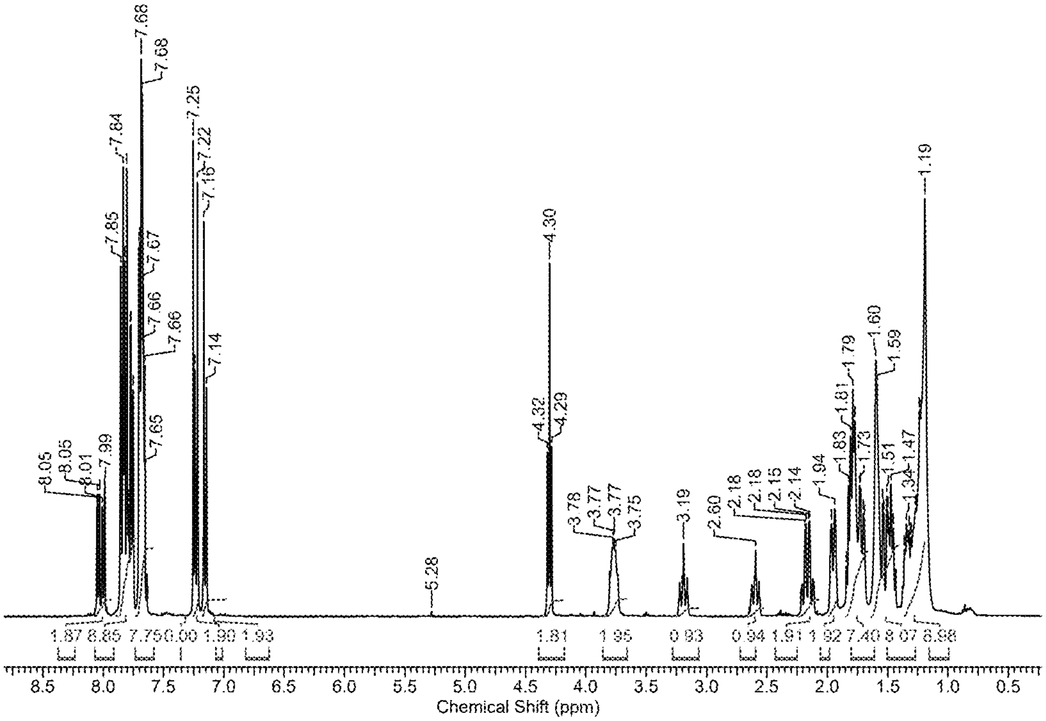
Figure 8:
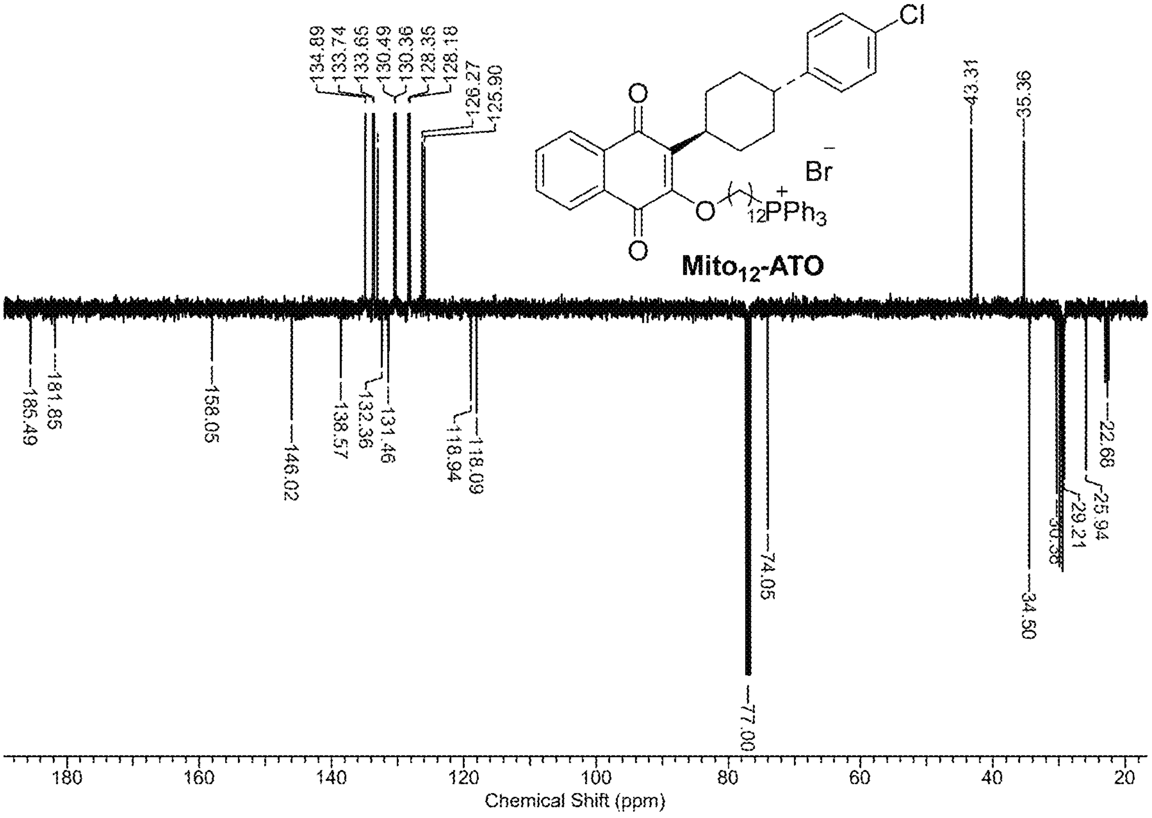
Figure 8:
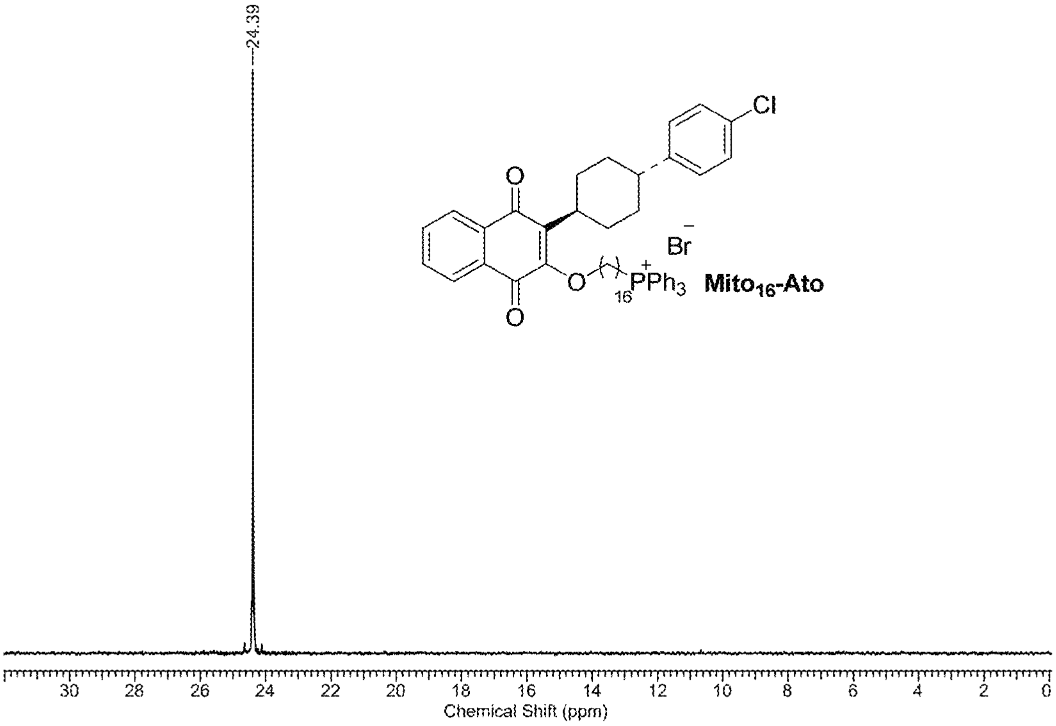
Figure 8:
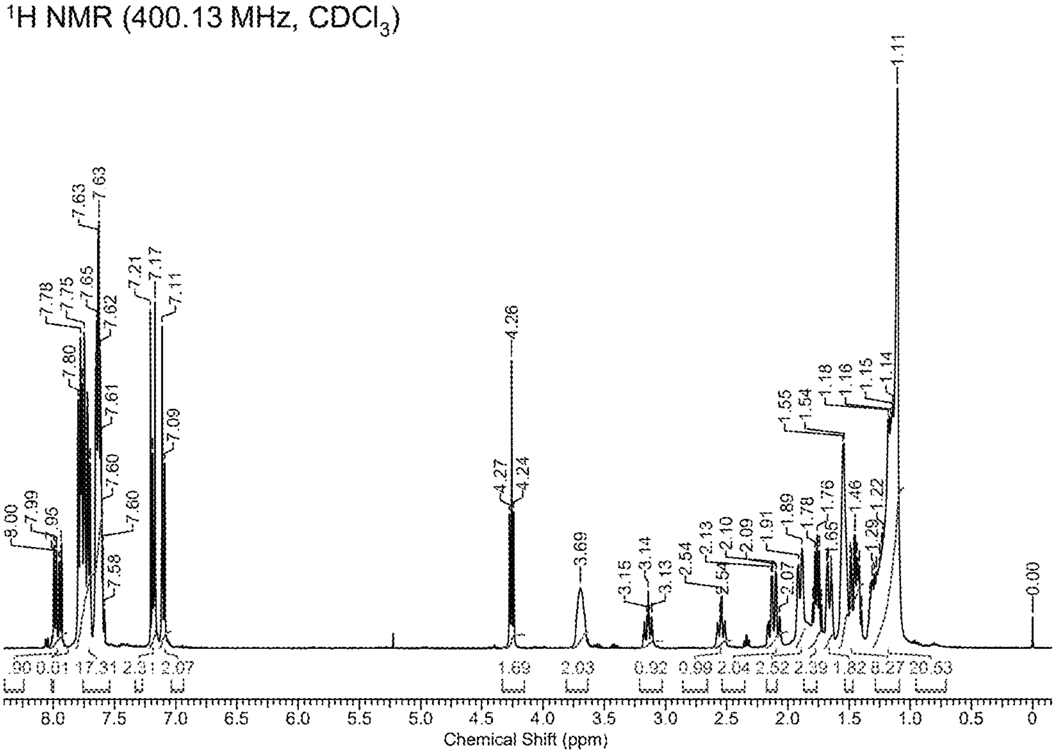
Figure 8:
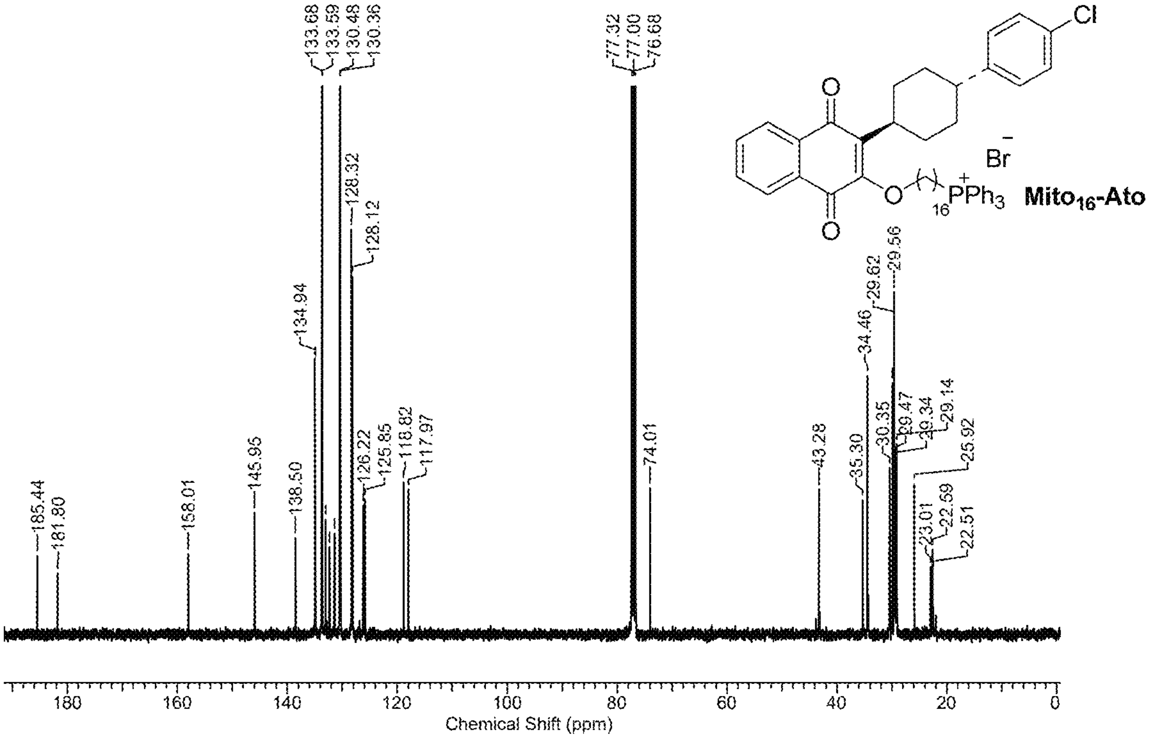
Figure 8:
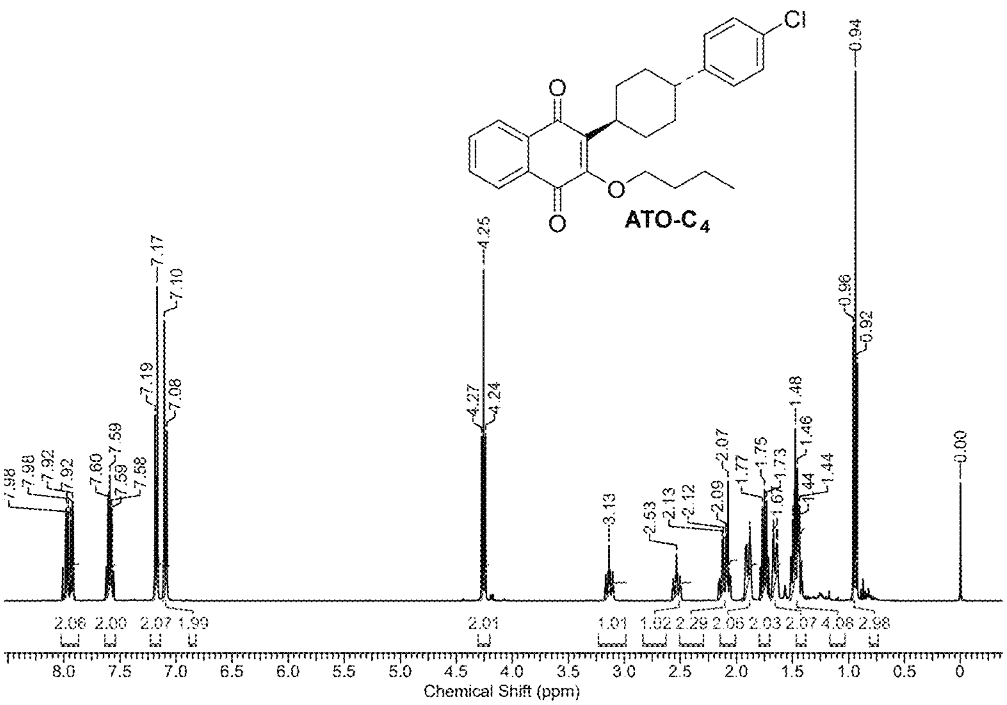
Figure 8:
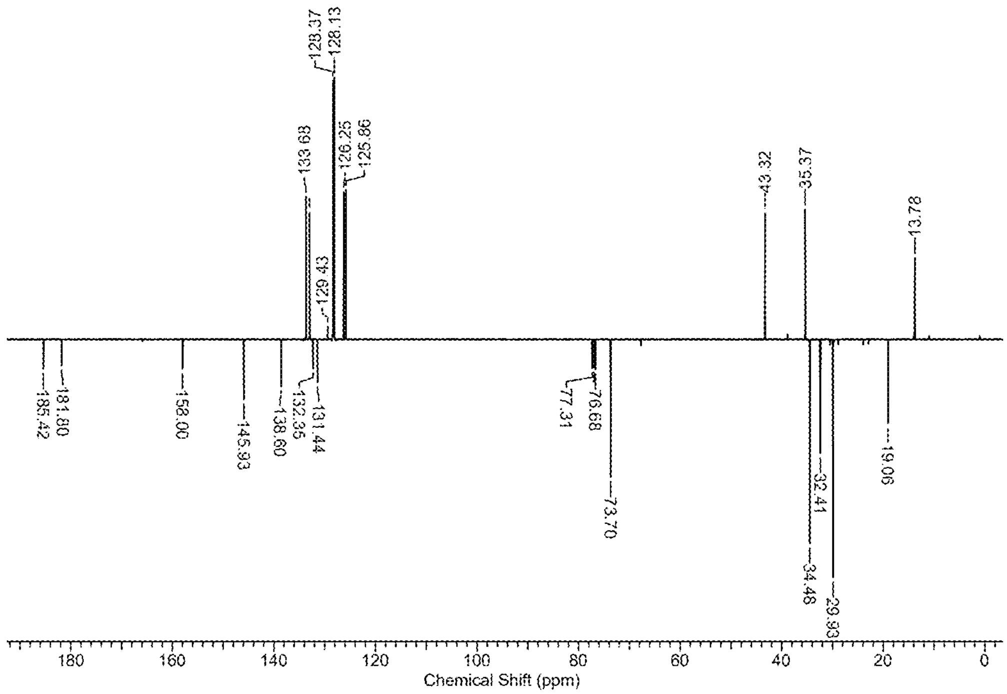
Figure 8:
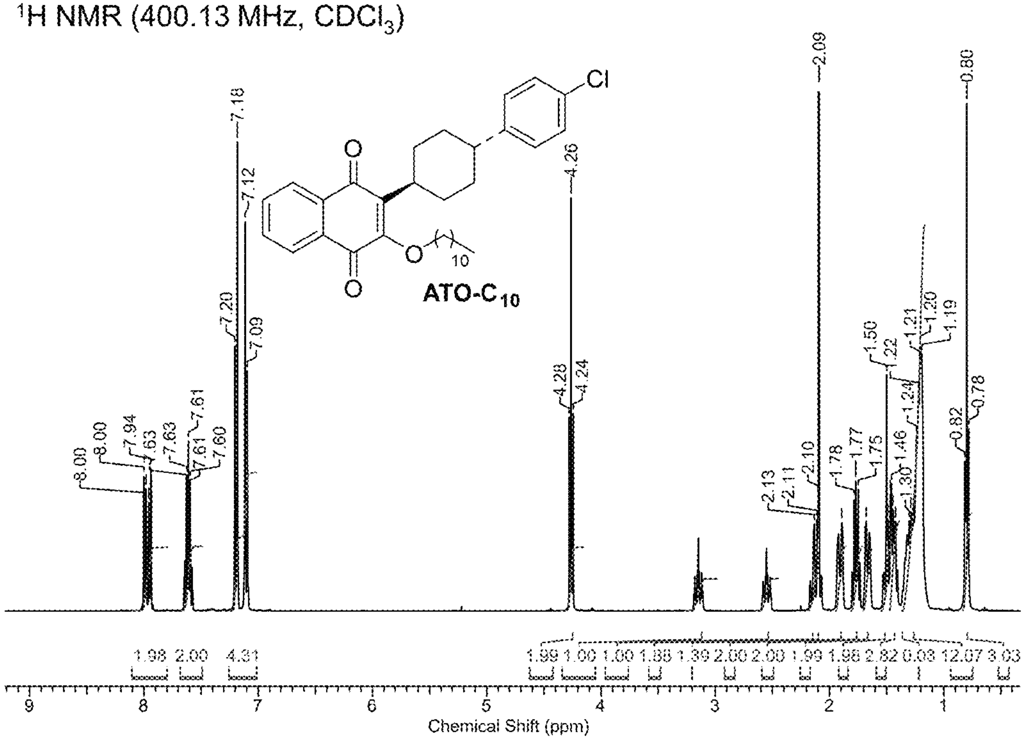
Figure 8:
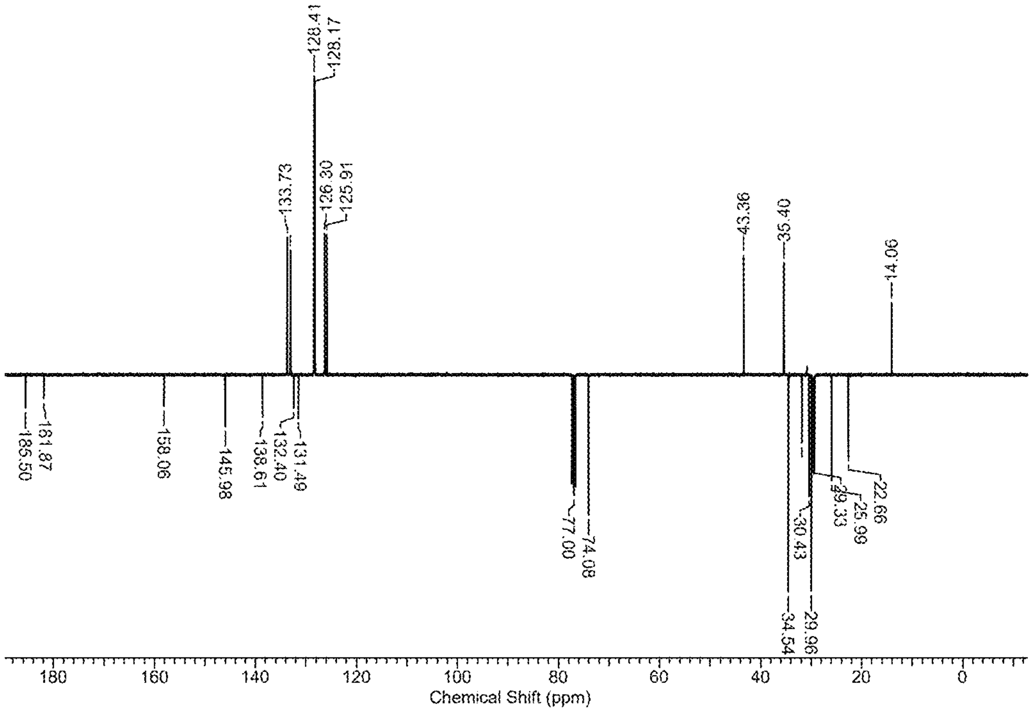

Syntheses and nuclear magnetic resonance (NMR) data of appropriate ATO controls lacking the $TPP^+$ group are given in FIGS. 7 and 8 in the Supplementary Materials.

Synthesis of Mito-ATO Analogs

The mitochondria-targeted analogs of ATO ($Mito_n$-ATO) were prepared by reacting the appropriates bromoalkyl-triphenylphosphonium bromides with ATO in the presence of potassium carbonate in dimethylformamide (DMF) (FIG. S1). In addition, the untargeted ATO derivatives (ATO-$C_n$) were prepared by adapting the procedure to the corresponding alkyl bromides (FIG. 7).

Synthesis of $Mito_4$-ATO $Mito_4$-ATO was prepared by reacting (4-bromobutyl)-triphenylphosphonium bromide with ATO in the presence of potassium carbonate in DMF (FIG. 1S). Briefly, (4-bromobutyl)-triphenylphosphonium bromide (0.39 g, 0.81 mmol) was added to a mixture of ATO (0.3 g, 0.82 mmol) and potassium carbonate (0.15 g, 0.82 mmol) in DMF. The mixture was stirred at 70° C. for 9 h. $CH_2Cl_2$ was then added to the mixture followed by the addition of water (20 mL). The organic layer was washed twice with water and dried over $Na_2SO_4$. The solvent was removed under reduced pressure. Diethyl ether was added to the mixture to precipitate out the compound that was purified by flash chromatography ($CH_2Cl_2$/EtOH, 9:1), yielding the product, $Mito_4$-ATO (0.47 g, 75% yield).

The HRMS calculated and found values are $C_{44}H_{41}ClO_3P^+$ [$M^+$]683.2476 and 683.2479. $^{31}$P NMR (400.13 MHz, $CDCl_3$) δ 24.66. $^{1}$H NMR (400.13 MHz, $CDCl_3$), δ 8.06-8.03 (1H, m), 7.95-7.93 (1H, m), 7.92-7.85 (6H, m), 7.79-7.72 (3H, m), 7.71-7.63 (8H, m), 7.25-7.21 (2H, m), 7.15-7.12 (2H, m), 4.26 (2H, t, J=5.6), 4.11-4.02 (2H, m), 3.13-3.03 (1H, m), 2.58-2.48 (1H, m), 2.37-2.28 (2H, m), 2.10-1.98 (4H, m), 1.92-1.88 (2H, m), 1.65 (2H, dd, J=12.7, 2.7), 1.54-1.39 (2H, m). $^{13}$C NMR (75 MHz, $CDCl_3$) δ 185.4, 181.7, 157.7, 145.7, 140.0, 134.9, 134.8, 133.8, 133.77, 133.68, 133.2, 132.3, 131.4, 131.3, 130.5, 130.3, 128.3, 128.2, 118.8, 117.9, 72.4, 43.1, 35.5, 34.3, 30.12 (d, 17.6), 30.1, 30.0, 22.2 (d, J=50.6), 19.1 (d, J=3.7). NMR spectra and related parameters are included in FIG. 8.

Synthesis of $Mito_{10}$-ATO $Mito_{10}$-ATO was prepared by reacting (10-bromodecyl)-triphenylphosphonium bromide with ATO in the presence of potassium carbonate in DMF (FIG. 7). Briefly, (10-bromodecyl)-triphenylphosphonium bromide (1.1 g, 1.9 mmol) was added to a mixture of ATO (0.73 g, 1.9 mmol) and potassium carbonate (0.3 g, 2.1 mmol) in DMF (4 mL). The mixture was stirred at 70° C. for 9 h. Methylene chloride ($CH_2Cl_2$) was added to the mixture, and then water (20 mL) was added. The organic layer was washed twice with water and dried over anhydrous sodium sulphate. The excess solvent was removed under reduced pressure. Diethyl ether was subsequently added to the mixture to precipitate the compound. Purification by flash chromatography, using a mixture of methylene chloride and ethanol (9:1), yielded the desired compound, $Mito_{10}$-ATO (1 g, 59% yield).

The high-resolution mass spectral (HRMS) calculated for Mito$_{10}$-ATO $C_{50}H_{53}ClO_3P^+$ $[M]^+$ 767.3415, found, 767.3420. $^{31}P$ NMR (400.13 MHz, $CDCl_3$) δ 24.48. $^1H$ NMR (400.13 MHz, $CDCl_3$), δ 8.08-7.98 (2H, m), 7.90-7.82 (6H, m), 7.81-7.75 (3H, m), 7.73-7.64 (8H, m), 7.25-7.23 (2H, m), 7.18-7.16 (2H, m), 4.30 (2H, t, J=6.6), 3.88-3.77 (2H, m), 3.25-3.15 (1H, m), 2.66-2.55 (1H, m), 2.24-2.11 (2H, m), 2.01-1.92 (2H, m), 1.86-1.77 (2H, m), 1.76-1.68 (4H, m), 1.60-1.40 (6H, m), 1.38-1.25 (8H, m). $^{13}C$ NMR (75 MHz, $CDCl_3$) δ 185.5, 181.9, 158.0, 146.0, 138.6, 134.9, 134.8, 133.8, 133.72, 133.67, 133.1, 132.4, 131.5, 131.4, 130.5, 130.4, 128.4, 128.2, 126.3, 125.9, 118.9, 118.1, 74.0, 43.3, 35.4, 34.5, 30.4 (d, J=14.0), 29.9, 29.5, 29.3, 29.2, 25.9, 22.8 (d, J=49.1), 22.7 (d, J=4.4). NMR spectra and related parameters are given in FIG. 8.

Synthesis of Mito$_{12}$-ATO

Mito$_{12}$-ATO was prepared by reacting (12-bromodecyl)-triphenylphosphonium bromide with ATO in the presence of potassium carbonate in DMF (FIG. 1S) as follows: (12-bromododecyl)-triphenylphosphonium bromide (0.6 g, 1.0 mmol) was added to a mixture of ATO (0.45 g, 1.2 mmol) and potassium carbonate (0.17 g, 1.2 mmol) in DMF. The mixture was stirred at 70° C. for 7 h. $CH_2Cl_2$ was added to the mixture followed by water (20 mL). The organic layer was washed twice with water and dried over $Na_2SO_4$. The solvent was removed under reduced pressure. Diethyl ether was then added to precipitate out the compound that was purified by flash chromatography ($CH_2Cl_2$/EtOH, 9:1) yielding the product, Mito$_{12}$-ATO (0.35 g, 35% yield).

HRMS calculated for Mito$_{12}$-ATO $C_{52}H_{57}ClO_3P^+$ $[M]^+$ 795.3728, found, 795.3729. $^{31}P$ NMR (400.13 MHz, $CDCl_3$) δ 24.44. $^1H$ NMR (400.13 MHz, $CDCl_3$), δ 8.07-7.97 (2H, m), 7.87-7.74 (9H, m), 7.72-7.63 (8H, m), 7.24-7.20 (2H, m), 7.18-7.13 (2H, m), 4.30 (2H, t, J=6.6), 3.82-3.72 (2H, m), 3.25-3.13 (1H, m), 2.65-2.55 (1H, m), 2.23-2.09 (2H, m), 1.99-1.92 (2H, m), 1.84-1.67 (7H, m), 1.63-1.42 (8H, m), 1.37-1.19 (9H, m). $^{13}C$ NMR (75 MHz, $CDCl_3$) δ 185.5, 181.9, 158.1, 146.0, 138.6, 134.92, 134.89, 133.7, 133.6, 133.1, 132.4, 131.5, 131.4, 130.5, 130.4, 128.4, 128.2, 126.3, 125.9, 118.9, 118.1, 74.1, 43.3, 35.4, 34.5, 30.5, 30.4, 30.3 (d, J=16.1), 29.9, 29.6, 29.5, 29.3, 29.24, 29.21, 25.9, 22.8 (d, J=49.2), 22.4 (d, J=4.4). The NMR spectra and related parameters are given in FIG. 8.

Synthesis of Mito$_{16}$-ATO

Mito$_{16}$-ATO was prepared by reacting (16-bromohexadecyl)-triphenylphosphonium bromide with ATO in the presence of potassium carbonate in DMF as follows: (16-bromohexadecyl)-triphenylphosphonium bromide (0.2 g, 0.34 mmol) was added to a mixture of ATO (0.13 g, 0.37 mmol) and potassium carbonate (0.05 g, 0.37 mmol) in DMF (2 mL). The mixture was stirred at 70° C. for 7 h. $CH_2Cl_2$ was added to the mixture as well as water (20 mL). The organic layer was washed twice with water and dried over $Na_2SO_4$. The solvent was removed under reduced pressure. Diethyl ether was the added to the mixture to precipitate out the compound that was purified by flash chromatography ($CH_2Cl_2$/EtOH, 9:1), yielding the product, Mito$_{16}$-ATO (0.16 g, 54% yield).

HRMS calculated for Mito$_{16}$-ATO $C_{56}H_{65}ClO_3P^+$ $[M]^+$ 851.4354, found, 851.4360. $^{31}P$ NMR (400.13 MHz, $CDCl_3$) δ 23.39. $^1H$ NMR (400.13 MHz, $CDCl_3$), δ 8.00-7.93 (2H, m), 7.81-7.59 (17H, m), 7.21-7.16 (2H, m), 7.11-7.09 (2H, m), 4.26 (2H, t, J=6.7), 3.75-3.63 (2H, m), 3.20-3.08 (11H, m), 2.60-2.48 (11H, m), 2.17-2.03 (2H, m), 1.94-1.85 (2H, m), 1.80-1.73 (2H, m), 1.70-1.63 (2H, m), 1.68-1.38 (8H, m), 1.33-1.06 (20H, m). $^{13}C$ NMR (75 MHz, $CDCl_3$) δ 185.54, 181.8, 158.0, 146.0, 138.5, 134.94, 134.91, 133.7, 133.6, 133.0, 132.3, 131.3, 131.4, 130.5, 130.4, 128.3, 128.1, 126.2, 125.9, 118.8, 118.0, 74.0, 43.3, 35.5, 34.5, 30.5, 30.4, 30.3, 29.9, 29.6, 29.59, 29.56, 29.52, 29.4, 29.3, 29.2, 29.1, 25.9, 22.8 (d, J=49.9), 22.6 (d, J=4.4). The NMR spectra and related parameters are given in FIG. 8.

Cell Culture

The following cell lines were obtained from the American Type Culture Collection (Manassas, VA), where they were regularly authenticated: MiaPaCa-2 (ATCC #CRL-1420, human pancreatic cancer), MDA-MB-231 (ATCC #HTB-26, human breast cancer), A549 (ATCC #CCL-185, human lung cancer), LLC (ATCC #CLR-1642, mouse lung cancer). LKR13 mouse lung cancer cells were a gift from Dr. Jonathan M. Kurie (MD Anderson Cancer Center, Houston, TX).[30] All cell lines were grown at 37° C. in 5% $CO_2$. MiaPaCa-2 and MDA-MB-231 cells were maintained in DMEM medium (Thermo Fisher Scientific, #11965) supplemented with 10% foetal bovine serum. A549, LLC, and LKR13 cells were maintained in RPMI 1640 medium (Thermo Fisher Scientific, #11875), supplemented with 10% foetal bovine serum. All cells were stored in liquid nitrogen and used within 20 passages after thawing.

Cell Proliferation Measurements

The IncuCyte Live-Cell Imaging system (IncuCyte Essen Bioscience Inc., Ann Arbor, MI) was used to monitor cell proliferation.[11-13] As shown in previous publications,[11,12] this imaging system is probe-free and noninvasive, and enables continuous monitoring of cell confluence over several days. The increase in the percentage of cell confluence was used as a surrogate marker of cell proliferation. In a 96-well plate, cells were plated at 1,000 cells per well in triplicates and left to adhere overnight. Cells were then treated with ATO, Mito-ATO analogs, and appropriate controls, and the cell confluency was recorded over several days in the IncuCyte S3 system.

Mitochondrial Function Measurements

Mitochondrial bioenergetic function was measured in real time using the Seahorse XF 96 Extracellular Flux Analyzer (Agilent, North Billerica, MA).[11-13,22] The OCR-based assessment of mitochondrial complex activities was carried out on acutely permeabilized cells in the presence of different mitochondrial substrates, i.e., pyruvate/malate, for complex I and duroquinol for complex III.[11,14,31,32] Rot, malonate, and antimycin A (Sigma-Aldrich, St. Louis, MO) were used as specific inhibitors of mitochondrial complexes I, II, and III, respectively. Briefly, cells that were intact after treatments were immediately permeabilized using the Seahorse XF Plasma Membrane Permeabilizer (Agilent). The mitochondrial complex I-driven OCR was assayed in mannitol and sucrose buffer[31] containing 10 mM pyruvate and 1.5 mM malate (substrates for complex I) and 10 mM malonate (which inhibits complex II activities). The mitochondrial complex III-driven OCR was assayed in mannitol and sucrose buffer containing 0.5 mM duroquinol (substrate for complex III) and 1 μM Rot and 10 mM malonate (which inhibit both complex I and II activities). The mitochondrial complex-dependent oxygen consumption (calculated as Rot- or antimycin A-inhibitable OCR equals basal OCR less OCR after Rot or antimycin A injection) was plotted against concentrations to determine the $IC_{50}$ values.

Immunosuppression Measurements

Mice. SMARTA triple reporter mice were generated in the following manner. First, IL-10 and IL-21 double-reporter mice[33] were generated by cross-breeding IL-21tRFP mice[34-35] with 10 BiT mice (kindly provided by Dr. Casey Weaver, University of Alabama at Birmingham). Double reporter mice were then crossed with GREAT (interferon-gamma reporter with endogenous polyA transcript) mice[36] from Jackson Laboratory (Stock No. 017581). These triple-reporter mice were then crossed with SMARTA mice[37] (kindly provided by Dr. Dorian McGavern, National Institutes of Health). Mice were bred and maintained in a closed breeding facility, and mouse handling conformed to the requirements of the Medical College of Wisconsin Institutional Animal Care and Use Committee guidelines. All experimental protocols were approved by the Medical College of Wisconsin Institutional Animal Care and Use Committee.

Cell culture. To differentiate $CD4^+$ T cells into a T regulatory cell phenotype, splenocytes from SMARTA triple-reporter mice were processed and the red blood cell lysed using an ACK (ammonium-chloride-potassium) lysis buffer. The cells were then activated with 1 μg/mL $GP_{61-10}$ peptide (GenScript, Piscataway, NJ) and 5 ng/mL TGF-β1 (Shenandoah Biotechnology, Inc., Warwick, PA). After one day of initial skewing, 100 μg/mL IL-2 along with ATO or Mito-ATO analogs of varying concentrations were added to the culture. Cells were cultured for six days and split once cells reached confluency; cells were replenished with IL-2 and compound accordingly. After six days in culture, cells were stained to assess the viability and phenotypic analysis via flow cytometry. LIVE/DEAD fixable violet or aqua dead cell stain (Invitrogen, Carlsbad, CA) was used to assess cell viability. The following antibodies were used for flow cytometry staining: PercP anti-mouse CD4 (clone: GK1.5; BioLegend, San Diego, CA), APC/Cy7 anti-mouse CD25 (clone: PC61; BioLegend), and PE anti-mouse FOXP3 (clone: FJK-16S; eBioscience, San Diego, CA). Flow cytometry data were acquired using a BD LSRII (BD Biosciences, CA) flow cytometer and analysed using FlowJo (Treestar, Inc., Ashland, OR).

Uptake of ATO and $Mito_{10}$-ATO into MiaPaCa-2 and A549 Cells

Intracellular levels of ATO and $Mito_{10}$-ATO analogs were quantitated by LC-MS/MS.[11,12] Cells ($1\times10^6$ per dish) were grown in 10-cm dishes and incubated with ATO and $Mito_{10}$-ATO for 24 h in full culture media. The compounds were extracted according to the published experimental protocol.[11,12] Briefly, cells were washed twice with ice-cold DPBS (Dulbecco's Phosphate Buffered Saline) and harvested. The cell pellet was immediately frozen in liquid nitrogen and stored at −80° C. For the extraction, the pellet was homogenized in 200 μl DPBS (2 μl were taken for protein assay) and extracted twice with a dichloromethane: methanol (2:1) mixture. The organic layers were combined and dried using a SpeedVac concentrator (Thermo Fisher Scientific, Waltham MA). The dry residue was dissolved in ice-cold methanol and taken for LC-MS/MS analysis. LC-MS/MS analyses were performed using a Kinetex Phenyl-Hexyl column (50 mm×2.1 mm, 1.7 μm; Phenomenex, Torrance, CA) equilibrated with a water:acetonitrile mixture (4:1) containing 0.1% formic acid. Compounds were eluted by increasing the content of acetonitrile from 20% to 100% over 4 min and detected using the MRM (multiple reaction monitoring) mode. Intracellular concentrations (μM/mg protein) of ATO and

REFERENCES FOR EXAMPLE 1

1 Fry, M. & Pudney, M. Site of action of the antimalarial hydroxynaphthoquinone, 2-[trans-4-(4'-chlorophenyl) cyclohexyl]-3-hydroxy-1,4-naphthoquinone (566C80). *Biochem. Pharmacol.* 43, 1545-1553, doi:10.1016/0006-2952(92)90213-3 (1992).

2 Araujo, F. G., Huskinson, J. & Remington, J. S. Remarkable in vitro and in vivo activities of the hydroxynaphthoquinone 566C80 against tachyzoites and tissue cysts of *Toxoplasma gondii. Antimicrob. Agents Chemother.* 35, 293-299, doi:10.1128/aac.35.2.293 (1991).

3 Cifuentes Kottkamp, A. et al. Atovaquone Inhibits Arbovirus Replication through the Depletion of Intracellular Nucleotides. *J. Virol.* 93, doi:10.1128/jvi.00389-19 (2019).

4 Kessl, J. J. et al. Molecular basis for atovaquone binding to the cytochrome bel complex. *J. Biol. Chem.* 278, 31312-31318, doi:10.1074/jbc.M304042200 (2003).

5 Birth, D., Kao, W.-C. & Hunte, C. Structural analysis of atovaquone-inhibited cytochrome bc1 complex reveals the molecular basis of antimalarial drug action. *Nat. Commun.* 5, 4029, doi:10.1038/ncomms5029 (2014).

6 Fiorillo, M. et al. Repurposing atovaquone: targeting mitochondrial complex III and OXPHOS to eradicate cancer stem cells. *Oncotarget* 7, 34084-34099, doi: 10.18632/oncotarget.9122 (2016).

7 Ashton, T. M. et al. The anti-malarial atovaquone increases radiosensitivity by alleviating tumour hypoxia. *Nat Commun* 7, 12308, doi:10.1038/ncomms12308 (2016).

8 Nayak, A. P., Kapur, A., Barroilhet, L. & Patankar, M. S. Oxidative Phosphorylation: A Target for Novel Therapeutic Strategies Against Ovarian Cancer. *Cancers* (*Basel*) 10, doi:10.3390/cancers10090337 (2018).

9 Xiang, M. et al. Gene expression-based discovery of atovaquone as a STAT3 inhibitor and anticancer agent. *Blood* 128, 1845-1853, doi:10.1182/blood-2015-07-660506 (2016).

10 Takabe, H. et al. A Repurposed Drug for Brain Cancer: Enhanced Atovaquone Amorphous Solid Dispersion by Combining a Spontaneously Emulsifying Component with a Polymer Carrier. *Pharmaceutics* 10, doi:10.3390/pharmaceutics10020060 (2018).

11 Cheng, G. et al. Mitochondria-Targeted Analogues of Metformin Exhibit Enhanced Antiproliferative and Radiosensitizing Effects in Pancreatic Cancer Cells. *Cancer Res.* 76, 3904-3915, doi:10.1158/0008-5472.Can-15-2534 (2016).

12 Cheng, G. et al. Mitochondria-targeted vitamin E analogs inhibit breast cancer cell energy metabolism and promote cell death. *BMC Cancer* 13, 285, doi:10.1186/1471-2407-13-285 (2013). $Mito_{10}$-ATO were calculated based on the standard curve (1 nM-100 M) and the protein concentrations of the collected samples.

13 Boyle, K. A. et al. Mitochondria-targeted drugs stimulate mitophagy and abrogate colon cancer cell proliferation. *J. Biol. Chem.* 293, 14891-14904, doi:10.1074/jbc.RA117.001469 (2018).

14 Cheng, G. et al. Targeting lonidamine to mitochondria mitigates lung tumorigenesis and brain metastasis. *Nat. Commun.* 10, 2205, doi:10.1038/s41467-019-10042-1 (2019).

15 Weinberg, S. E. et al. Mitochondrial complex III is essential for suppressive function of regulatory T cells. *Nature* 565, 495-499, doi:10.1038/s41586-018-0846-z (2019).

16 Zielonka, J. et al. Mitochondria-targeted triphenylphosphonium-based compounds: Syntheses, mechanisms of action, and therapeutic and diagnostic applications. *Chem. Rev.* 117, 10043-10120, doi:10.1021/acs.chemrev.7b00042 (2017).

17 Das, M., Alzaid, F. & Bayry, J. Regulatory T Cells under the Mercy of Mitochondria. *Cell Metab* 29, 243-245, doi:10.1016/j.cmet.2019.01.012 (2019).

18 Viswanadhan, V. N., Ghose, A. K., Revankar, G. R. & Robins, R. K. Atomic physicochemical parameters for three dimensional structure directed quantitative structure-activity relationships. 4. Additional parameters for hydrophobic and dispersive interactions and their application for an automated superposition of certain naturally occurring nucleoside antibiotics. *Journal of Chemical Information and Computer Sciences* 29, 163-172, doi: 10.1021/ci00063a006 (1989).
19 Klopman, G., Li, J.-Y., Wang, S. & Dimayuga, M. Computer Automated log P Calculations Based on an Extended Group Contribution Approach. *Journal of Chemical Information and Computer Sciences* 34, 752-781, doi:10.1021/ci00020a009 (1994).
20 Barton, V., Fisher, N., Biagini, G. A., Ward, S. A. & O'Neill, P. M. Inhibiting *Plasmodium* cytochrome bc1: a complex issue. *Curr. Opin. Chem. Biol.* 14, 440-446, doi:10.1016/j.cbpa.2010.05.005 (2010).
21 Sodero, A. C. et al. Insights into cytochrome bc1 complex binding mode of antimalarial 2-hydroxy-1,4-naphthoquinones through molecular modelling. *Mem. Inst. Oswaldo Cruz* 112, 299-308, doi:10.1590/0074-02760160417 (2017).
22 Weinberg, S. E. & Chandel, N. S. Targeting mitochondria metabolism for cancer therapy. *Nat. Chem. Biol.* 11, 9-15, doi:10.1038/nchembio.1712 (2015).
23 Ino, Y. et al. Immune cell infiltration as an indicator of the immune microenvironment of pancreatic cancer. *Br. J. Cancer* 108, 914-923, doi:10.1038/bjc.2013.32 (2013).
24 Wang, Y. A. et al. Effects of tumor metabolic microenvironment on regulatory T cells. *Mol Cancer* 17, 168, doi:10.1186/s12943-018-0913-y (2018).
25 Zhou, Y. et al. Prognostic value of tumor-infiltrating Foxp3+ regulatory T cells in patients with breast cancer: a meta-analysis. *J Cancer* 8, 4098-4105, doi:10.7150/jca.21030 (2017).
26 Chaudhary, B. & Elkord, E. Regulatory T Cells in the Tumor Microenvironment and Cancer Progression: Role and Therapeutic Targeting. *Vaccines* (*Basel*) 4, doi: 10.3390/vaccines4030028 (2016).
27 Ohue, Y. & Nishikawa, H. Regulatory T (Treg) cells in cancer: Can Treg cells be a new therapeutic target? *Cancer Sci.* 110, 2080-2089, doi:10.1111/cas.14069 (2019).
28 Shitara, K. & Nishikawa, H. Regulatory T cells: a potential target in cancer immunotherapy. *Ann. N. Y. Acad. Sci.* 1417, 104-115, doi:10.1111/nyas.13625 (2018).
29 Anso, E. et al. The mitochondrial respiratory chain is essential for haematopoietic stem cell function. *Nat. Cell Biol.* 19, 614-625, doi:10.1038/ncb3529 (2017).
30 Zhong, L. et al. Identification of secreted proteins that mediate cell-cell interactions in an in vitro model of the lung cancer microenvironment. *Cancer Res.* 68, 7237-7245, doi:10.1158/0008-5472.Can-08-1529 (2008).
31 Salabei, J. K., Gibb, A. A. & Hill, B. G. Comprehensive measurement of respiratory activity in permeabilized cells using extracellular flux analysis. *Nat Protoc* 9, 421438, doi:10.1038/nprot.2014.018 (2014).
32 Wheaton, W. W. et al. Metformin inhibits mitochondrial complex I of cancer cells to reduce tumorigenesis. *Elife* 3, e02242, doi:10.7554/eLife.02242 (2014).
33 Xin, G. et al. Single-cell RNA sequencing unveils an IL-10-producing helper subset that sustains humoral immunity during persistent infection. *Nat Commun* 9, 5037, doi:10.1038/s41467-018-07492-4 (2018).
34 Xin, G. et al. A Critical Role of IL-21-Induced BATF in Sustaining CD8-T-Cell-Mediated Chronic Viral Control. *Cell Rep* 13, 1118-1124, doi:10.1016/j.celrep.2015.09.069 (2015).
35 Weinstein, J. S. et al. TFH cells progressively differentiate to regulate the germinal center response. *Nat. Immunol.* 17, 1197-1205, doi:10.1038/ni.3554 (2016).
36 Reinhardt, R. L., Liang, H.-E. & Locksley, R. M. Cytokine-secreting follicular T cells shape the antibody repertoire. *Nat. Immunol.* 10, 385-393, doi:10.1038/ni.1715 (2009).
37 Oxenius, A., Bachmann, M. F., Zinkernagel, R. M. & Hengartner, H. Virus-specific MHC-class II-restricted TCR-transgenic mice: effects on humoral and cellular immune responses after viral infection. *Eur. J. Immunol.* 28, 390-400, doi:10.1002/(sici)1521-4141(199801)28:01<390::Aid-immu390>3.0.Co; 2-o (1998).

Example 2

Additional Mito-ATO Compounds of the Present Disclosure.

The $Mito_{PEG}$-ATO compounds of the present invention can be synthesized according to the following reactions:

Scheme. Reagents and conditions: i, triphenylphosphine, neat, 90° C.; ii, Atovaquone, $K_2CO_3$, DMF, 70° C., 12 h.

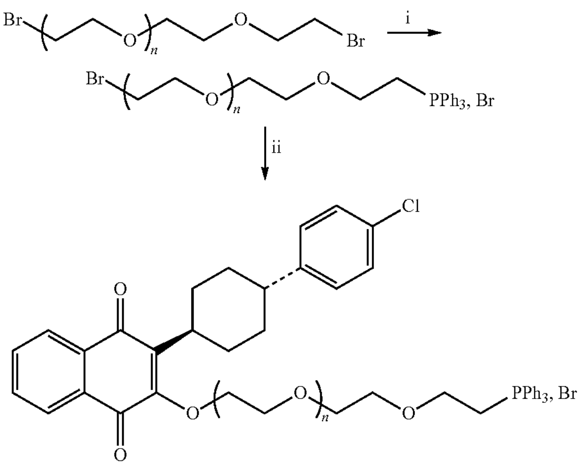

$Mito_{PEG}$-Ato

The $Mito_{Me}$-ATO compounds of the present invention can be synthesized according to the following reactions:

Scheme. Reagents and conditions: i, tris-(4-methylphenyl)-phosphine, neat, 90° C.; ii, Atovaquone, $K_2CO_3$, DMF, 70° C., 12 h.

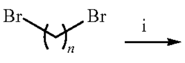

-continued

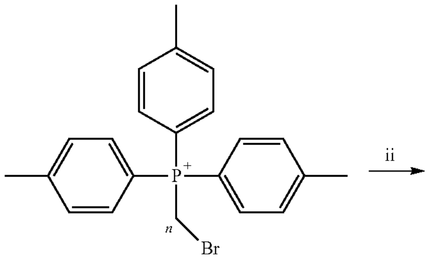

Mito$_{Me}$-Br

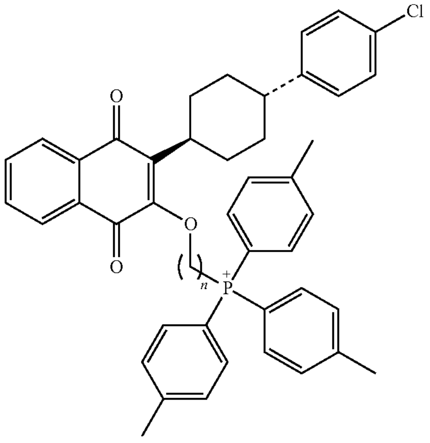

Mito$_{Me}$-Ato

The Mito$_{OMe}$-ATO compounds of the present invention can be synthesized according to the following reactions:

Scheme. Reagents and conditions: i, tris-(4-methylphenyl)-phosphine, neat, 90° C.; ii, Atovaquone, $K_2CO_3$, DMF, 70° C., 12 h.

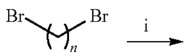

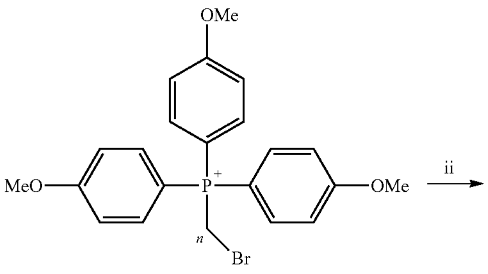

Mito$_{OMe}$-Br

-continued

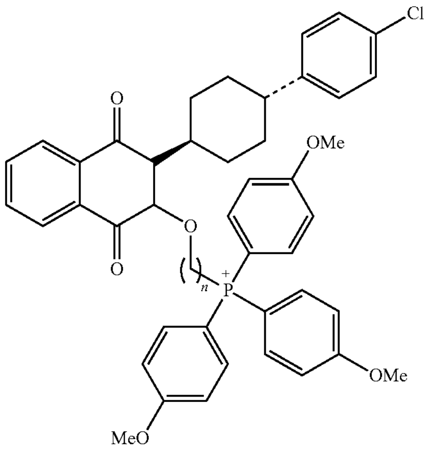

Mito$_{OMe}$-Ato

The Mito$_{Cl}$-ATO compounds of the present invention can be synthesized according to the following reactions:

Scheme. Reagents and conditions: i, Dibromalcane, $K_2CO_3$, DMF, rt. ii, tris-(4-clhorophenyl)-phosphine, toluene, toluene, reflux, 2 days.

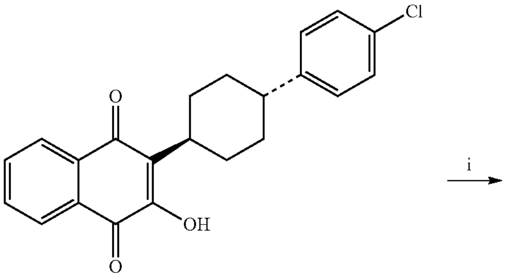

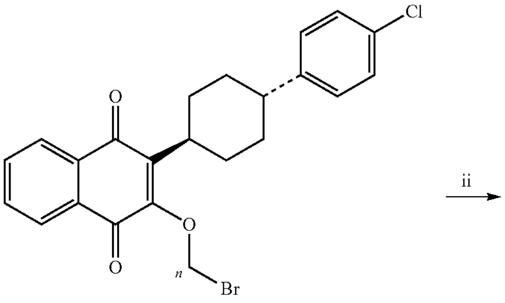

-continued

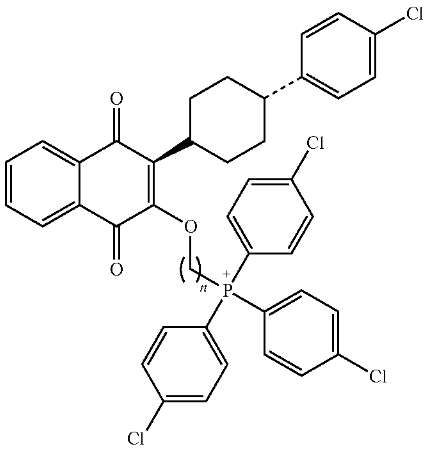

Mito$_{Cl}$-Ato

The Mito$_{CF3}$-ATO compounds of the present invention can be synthesized according to the following reactions:

Scheme. Reagents and conditions: i, Dibromoalcane, $K_2CO_3$, DMF, rt. ii, tris-[4-(trifluoromethyl)phenyl]-phosphine, toluene, reflux, 3 days.

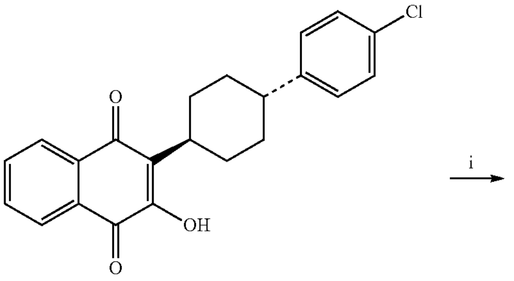

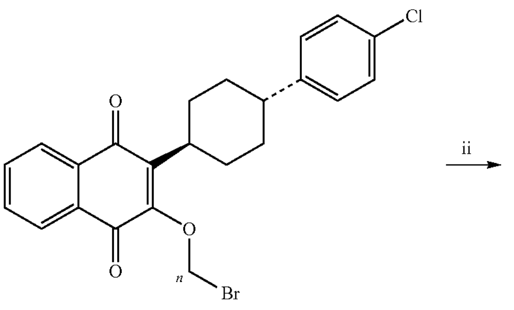

-continued

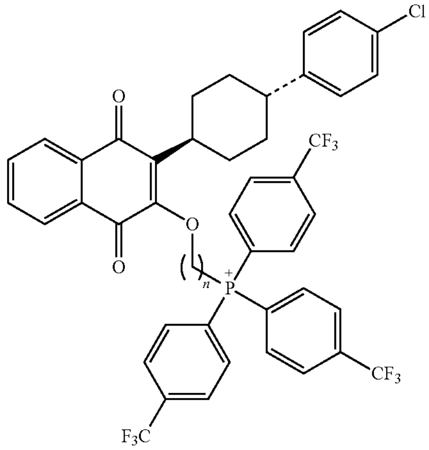

Mito$_{CF3}$-Ato

The Mito$_{Cy}$-ATO compound of the present invention can be synthesized according to the following reactions:

Scheme. Reagents and conditions: i, Atovaquone, $K_2CO_3$, DMF, 70° C., 12 h.

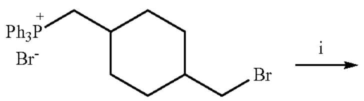

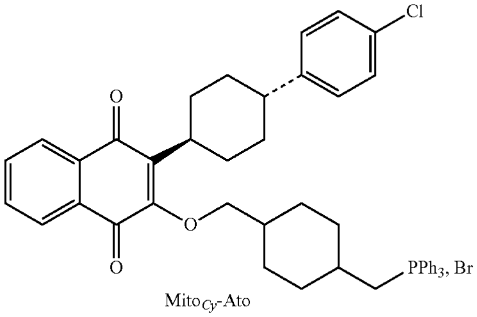

Mito$_{Cy}$-Ato

The Mito$_{Phen}$-ATO compound of the present invention can be synthesized according to the following reactions:

Scheme. Reagents and conditions: i, Atovaquone, $K_2CO_3$, DMF, 70° C., 12 h.

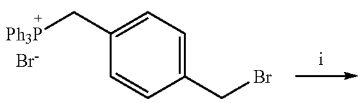

-continued

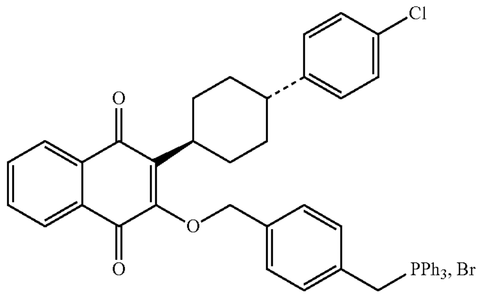

$Mito_{Phen}$-Ato

The $Mito_{Ato2}$-ATO compounds of the present invention can be synthesized according to the following reactions:

Scheme. Reagents and conditions: i, triphenylphosphine, neat, 90° C.; ii, Atovaquone, $K_2CO_3$, DMF, 70° C., 12 h

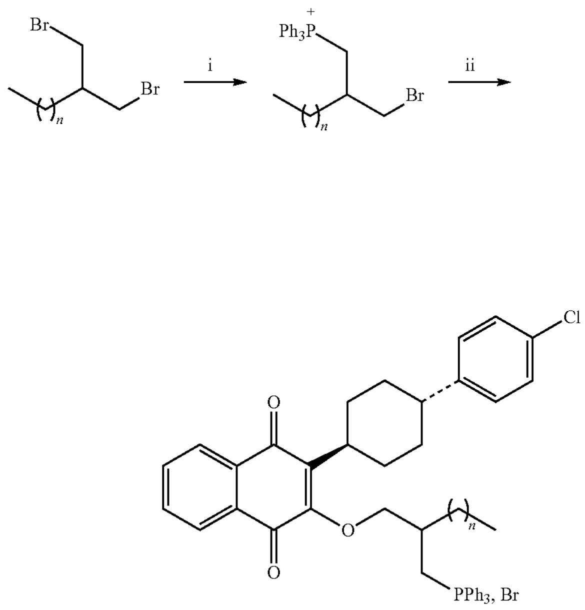

$Mito_n$-Ato2

The $Alky_{10}$-ATO compound of the present invention can be synthesized according to the following reactions Scheme. Reagents and conditions: i, Atovaquone, $K_2CO_3$, DMF, 70° C., 12 h.

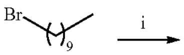

-continued

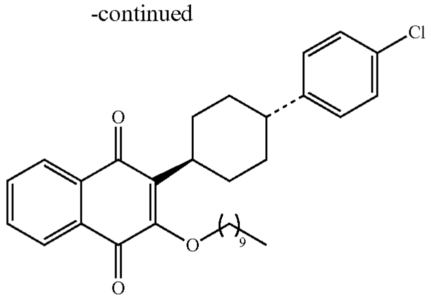

Alkyl-Ato

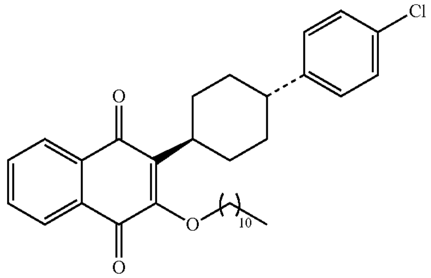

$Alkyl_{10}$-Ato

Example 3

Effects of ATO and Mito-PEG-ATO on Cell Proliferation in Brain Cancer Cells.

Figure 11:
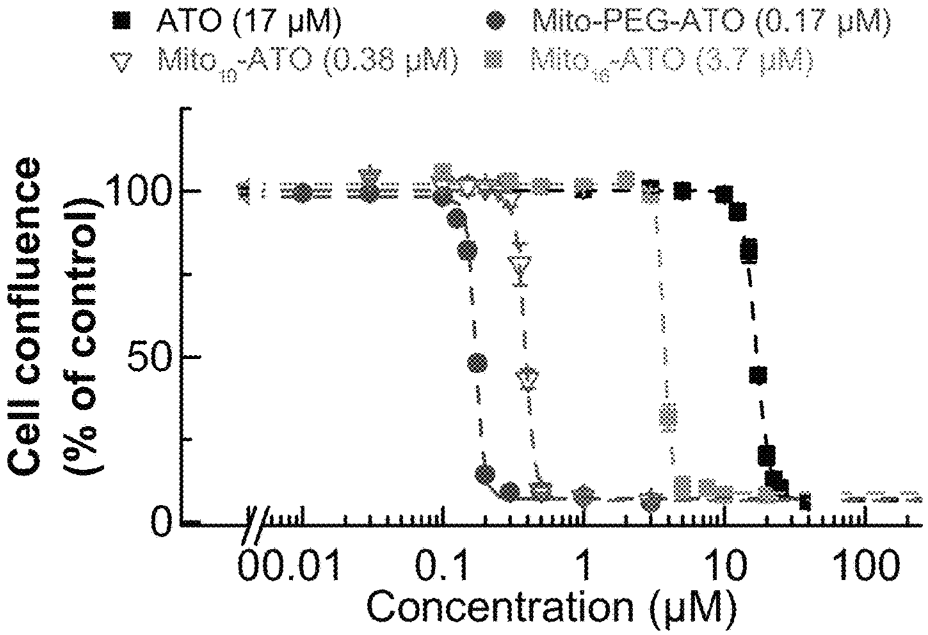
FIG. 11. Mito-PEG-ATO effects on cell proliferation in brain cancer cells, U87MG. Mito-PEG-ATO reduces cancer cell growth at lower concentrations than mito-ATO.
Figure 11:
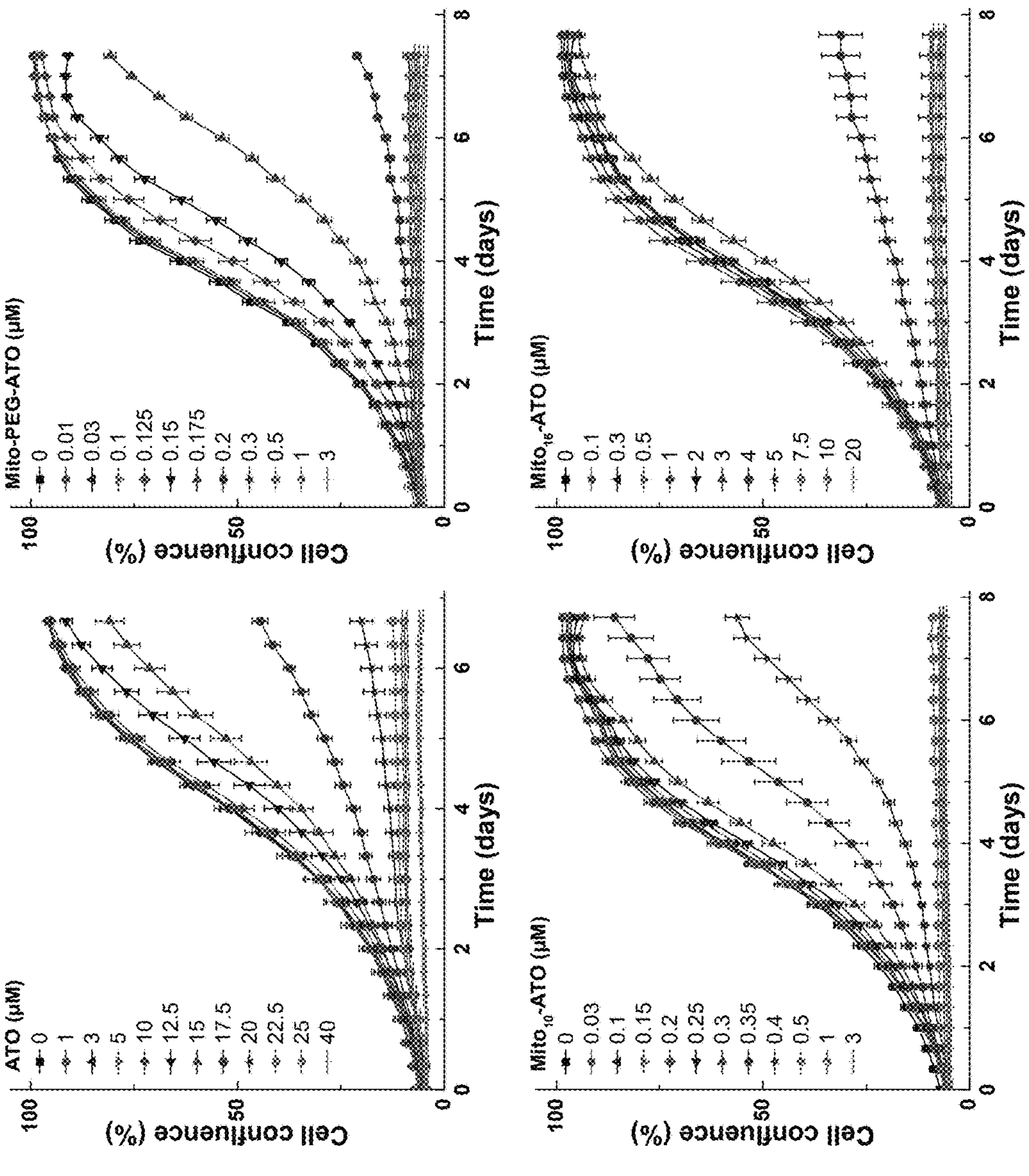
Figure 11:
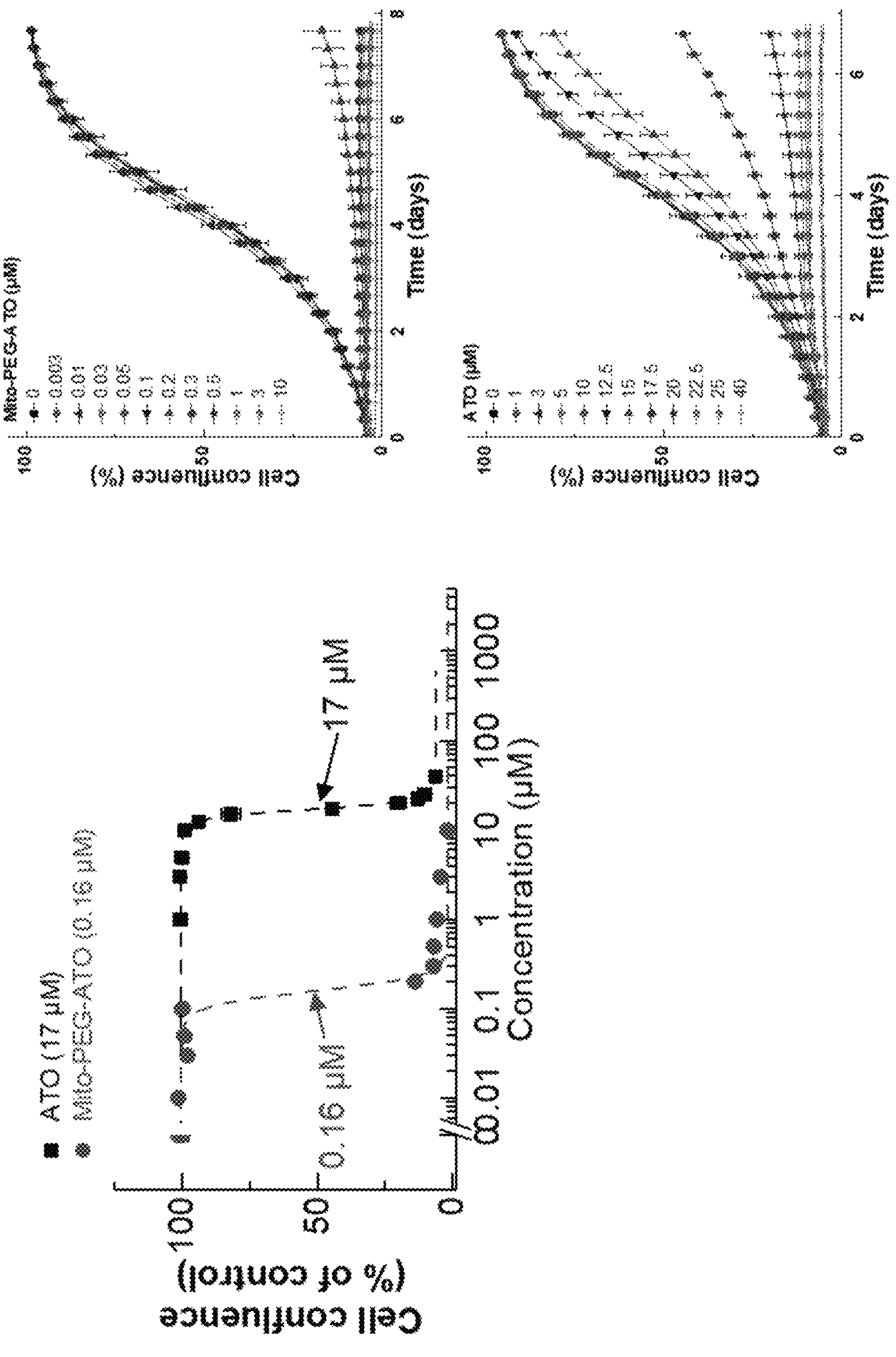
Figure 12:
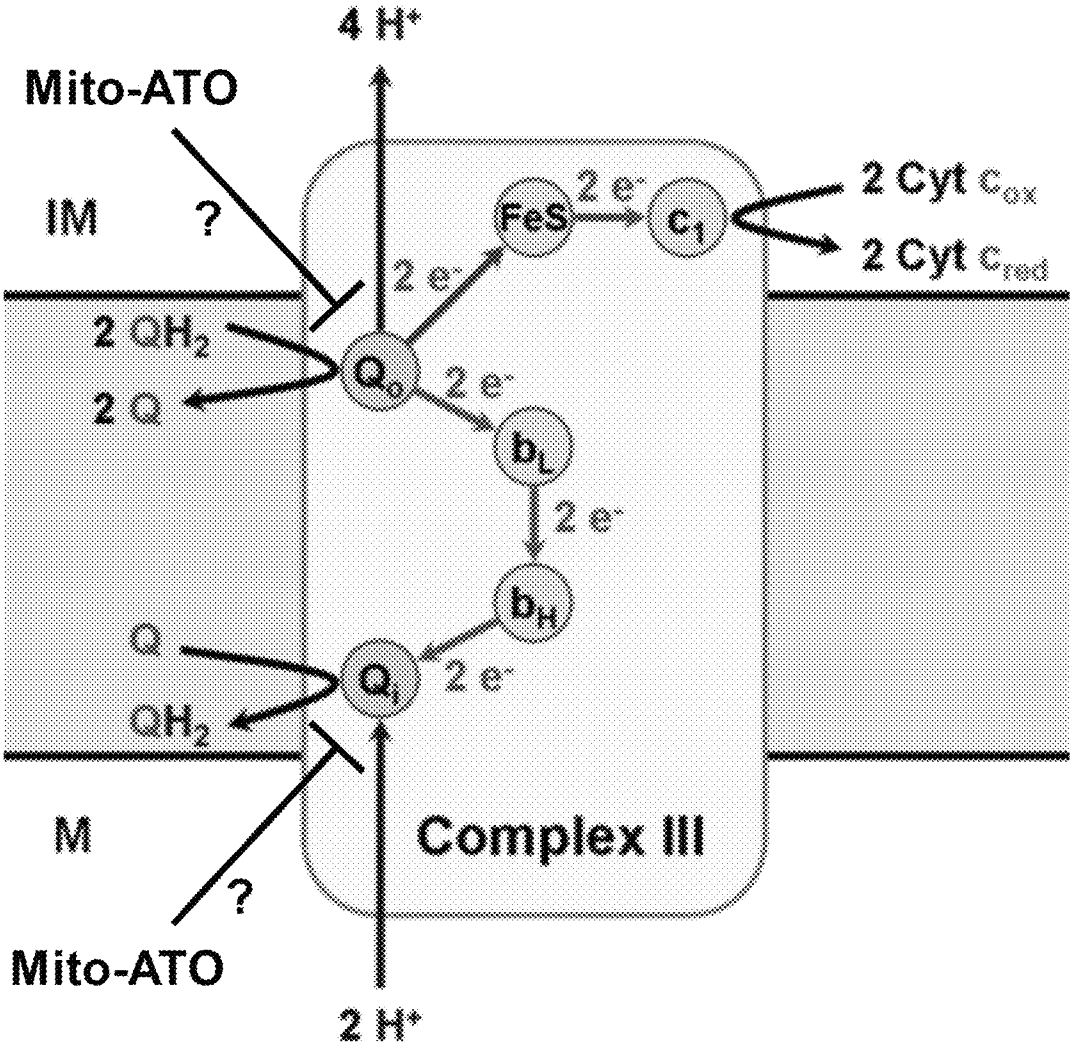
FIG. 12 is a schematic representation of mito-ATO binding to $Q_0$ and $Q_1$ site of the cyt bc1 complex, and inhibiting complex III.

FIG. 11 shows mito-ATO being used effectively on brain cancer cells. It also shows the use of a PEGylated mito-ato (mito-PEG-ATO) is more potent than standard $mito_{10}$-ATO.

Example 4

Effects of Intratumoral Injection of Mito-ATO on Tumor Size.

Figure 13:
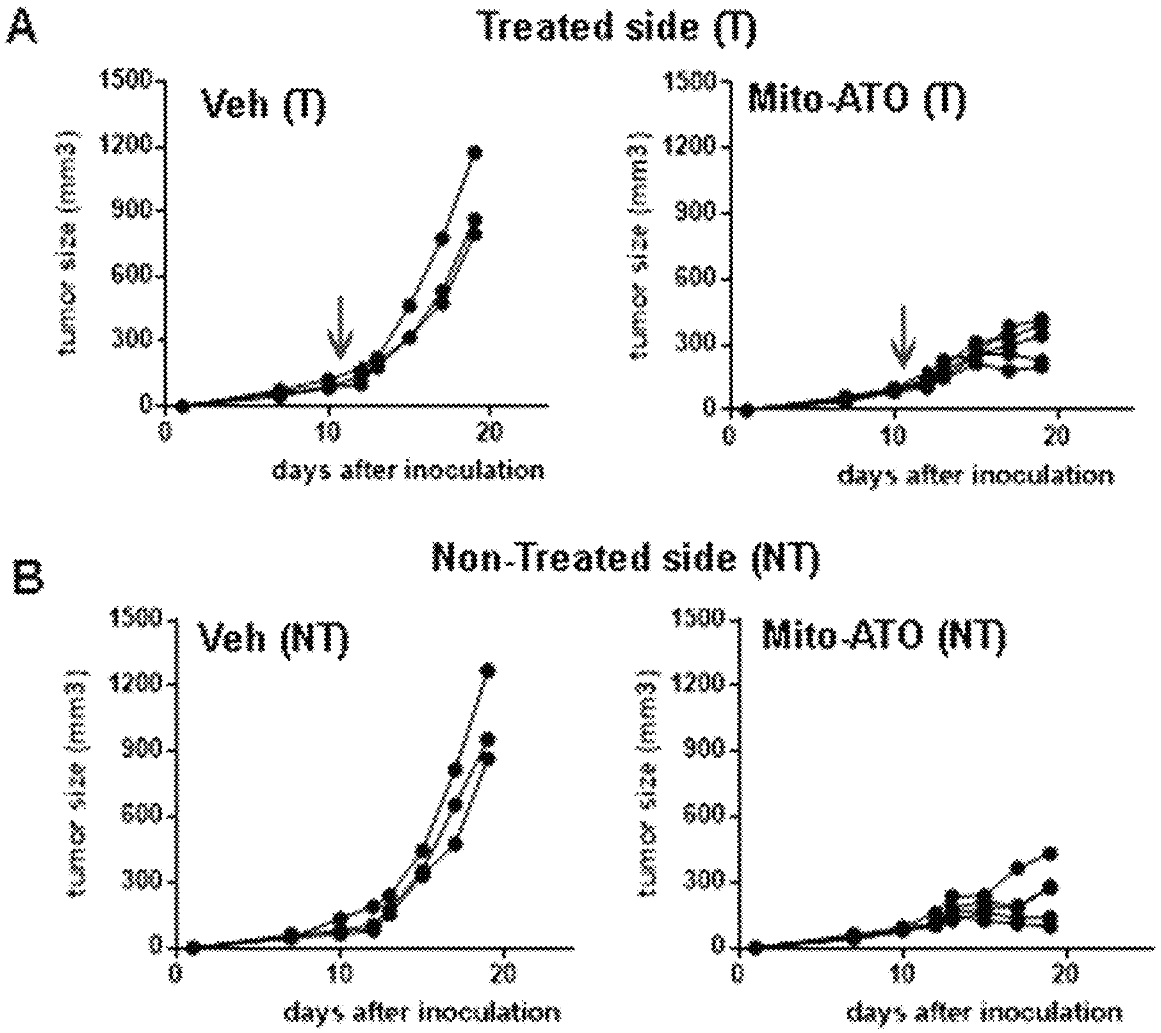
FIG. 13 demonstrates the systemic immune response induced by Mito-ATO. Panel A shows the inhibitory effect of Mito-ATO on tumor growth at the injection site. Panel B shows the tumor growth at the non-treated site which is also inhibited, revealing the potential systemic antitumor immune response induced by Mito-ATO.

The inventors tested the effect of Mito-ATO on systemic antitumor immune response in an immunocompetent mouse lung cancer model (FIG. 13). Treatment started (red arrow, FIG. 13) 14 days after tumor inoculation when the tumors reached 180-200 mm3. Mice then received daily injections of intratumoral vehicle or Mito-ATO over six days. Panel A shows tumor growth at the injection site. Tumor curves presented in panel B show tumor growth at the non-injection site, which reflects the systemic antitumor effect of the mitochondrial drug, Mito-ATO (FIG. 13). These studies reveal the systemic antitumor immune response induced by Mito-ATO.

Example 5

Potential Synergistic Effect of ATO and Mito-ATO.

Because of different molecular targeting, it is conceivable that ATO and mito-ATO will be synergistic in their antiproliferative effects. Several mitochondria-targeted cationic drugs cross the blood-brain barrier, and although ATO is very effective in inhibiting glioblastoma cells, it does not accumulate to high enough levels in the brain. Clearly, exacerbating the effects of ATO by combining it with mito-ATO could be of great therapeutic importance.

We claim:

1. A mito-ATO compound of formula (I)

(I)

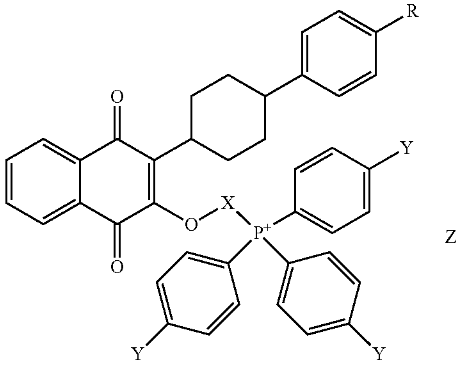

wherein

X is selected from an unsubstituted $C_1$-$C_{20}$ alkyl, substituted $C_1$-$C_{20}$ alkyl, $C_2$-$C_{20}$ alkenyl, phenyl, phenyl substituted $C_1$-$C_{20}$ alkyl, cycloalkyl substituted $C_1$-$C_{20}$ alkyl, an aminoacid, and polyethylene glycol (PEG);

each Y is independently selected from —H, —$CF_3$, methyl (Me), Cl, OMe, $C(O)CH_3$, $NO_2$, $N(Me)_2$;

R is selected from H, F, Cl, Br, and I; and $Z^-$ is selected from halogen, 2,2,2-trifluoroacetic acid (TFA), $HO^-$, $RCOO^-$, and acetic acid.

2. The mito-ATO compound of claim 1, wherein X is an unsubstituted $C_1$-$C_{20}$ alkyl, each Y is H, R is Cl, and $Z^-$ is Br.

3. The mito-ATO compound of claim 1, wherein the compound is:

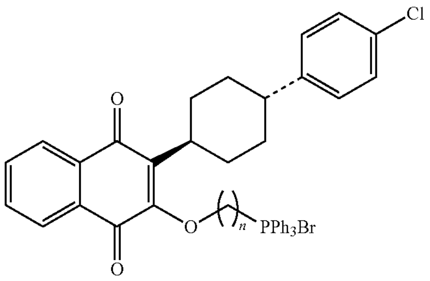

wherein n is an integer between 1 and 20.

4. The mito-ATO compound of claim 1, wherein the compound is:

(i)

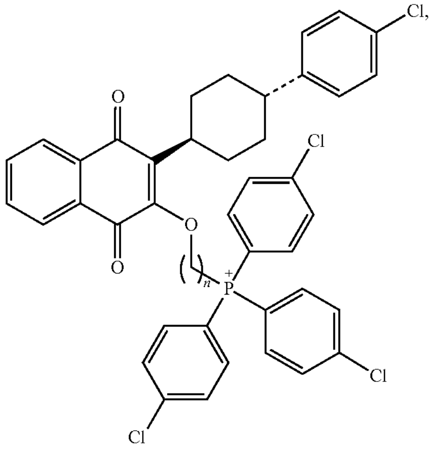

$Mito_{Cl}$-Ato (ii)

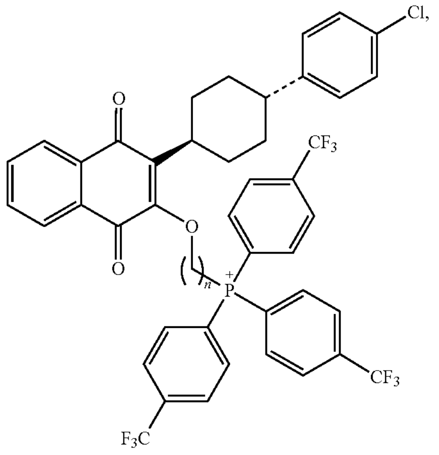

$Mito_{CF3}$-Ato (iii)

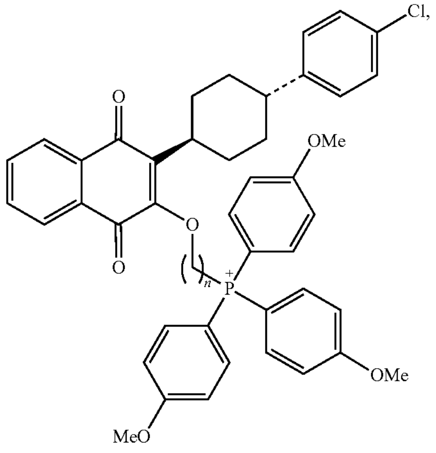

or $Mito_{OMe}$-Ato

-continued (iv)

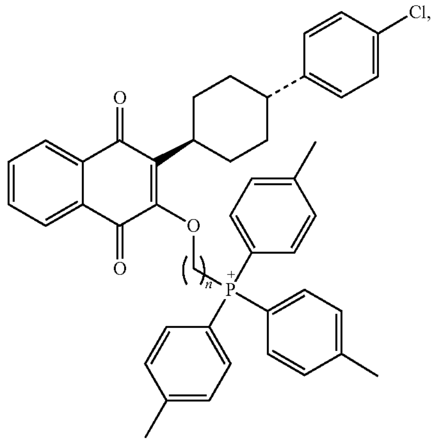

$Mito_{Me}$-Ato wherein n is an integer between 1 and 20.

5. The mito-ATO compound of claim 1, wherein the compound is:

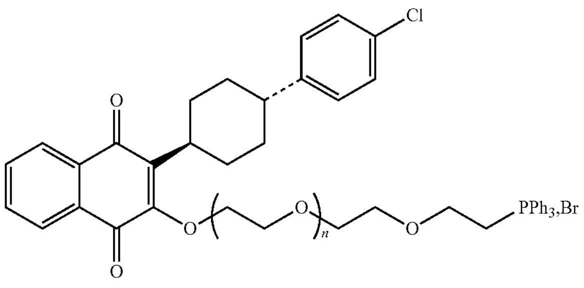

$Mito_{PEG}$-Ato wherein n is an integer between 1 and 20.

6. The mito-ATO compound of claim 1, wherein X is a substituted $C_1$-$C_{20}$ alkyl, each Y is H, R is Cl, and $Z^-$ is Br.

7. The mito-ATO compound of claim 6, wherein the compound is:

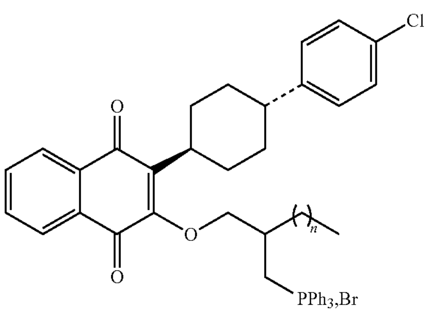

$Mito_n$-Ato wherein n is an integer between 1 and 20.

8. A mito-ATO compound of formula (II)

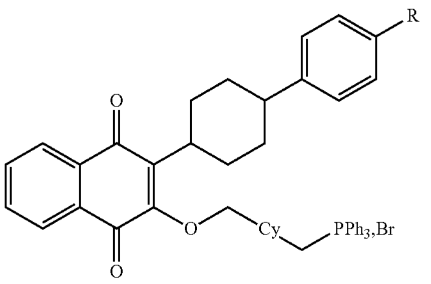

wherein Cy is a cyclic compound selected from cycloalkyl and aryl, and R is Cl.

9. The mito-ATO compound of claim 8, wherein the compound is:

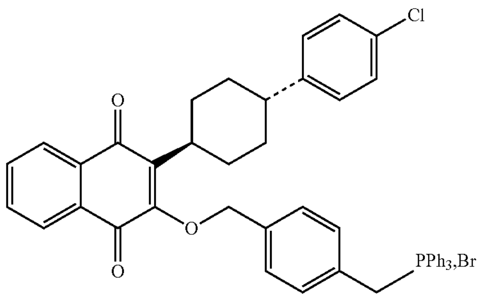

10. The mito-ATO compound of claim 8, wherein the compound is:

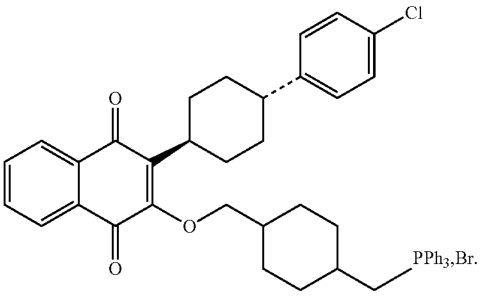

11. The mito-ATO compound of claim 1, wherein n is an integer from 1-10.

12. A composition comprising the mito-ATO compound of claim 1 and a pharmaceutically acceptable carrier.

13. A method of reducing or inhibiting cancer cell growth in a subject having cancer, the method comprising:

administering the mito-ATO compound of claim 1 in a therapeutically effective amount to reduce or inhibit cancer cell growth.

14. The method of claim 13, wherein the cancer is pancreatic cancer or brain cancer.

15. The method of reducing or inhibiting cancer cell growth in a subject having cancer, the method comprising:

administering the mito-ATO compound of claim 1, and administering atovaquone (ATO), wherein the mito-ATO and ATO in combination are administered in a therapeutically effective amount to reduce or inhibit cancer cell growth.

16. The method of claim 13, wherein the method further comprises administering an anti-cancer therapy.

17. The method of claim 16, wherein the anti-cancer therapy is selected from the group consisting of radiation, chemotherapy, and a combination thereof.

18. A method of increasing an effector T cell response to an anti-cancer therapy in a cancer patient, the method comprising administering the mito-ATO compound of claim 1 in a therapeutically effective amount to increase the effector T cell response to the anti-cancer therapy.

19. The method of claim 18, wherein the T-cell response is a CD4 T-cell, IFNγ T-cell, or FoxP3+CD25+ T-cell response.

20. The method of claim 18, wherein the method further comprises administering an anti-cancer therapy.

21. The method of claim 20, wherein the anti-cancer therapy is selected from the group consisting of radiation, chemotherapy, and a combination thereof.

22. A kit comprising at least one mito-ATO compound of claim 1, a pharmaceutically acceptable carrier or diluent, and instructional material.

* * * * *